US012577289B2

(12) United States Patent
Kuhns et al.

(10) Patent No.: US 12,577,289 B2
(45) Date of Patent: Mar. 17, 2026

(54) SURROGATE CO-RECEPTORS FOR T CELLS AND METHODS OF USE

(71) Applicant: ARIZONA BOARD OF REGENTS ON BEHALF OF THE UNIVERSITY OF ARIZONA, Tucson, AZ (US)

(72) Inventors: Michael S. Kuhns, Tucson, AZ (US); Deepta Bhattacharya, Tucson, AZ (US); Heather Lynn Bronnimann, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 1214 days.

(21) Appl. No.: 17/479,898

(22) Filed: Sep. 20, 2021

(65) Prior Publication Data

US 2022/0002379 A1     Jan. 6, 2022

Related U.S. Application Data

(60) Continuation-in-part of application No. PCT/US2020/023942, filed on Mar. 20, 2020, and a continuation-in-part of application No. 17/345,425, filed on Jun. 11, 2021, now abandoned, which is a division of application No. 15/738,467, filed as application No. PCT/US2016/040177 on Jun. 29, 2016, now Pat. No. 11,059,880.

(60) Provisional application No. 62/821,222, filed on Mar. 20, 2019, provisional application No. 62/186,865, filed on Jun. 30, 2015.

(51) Int. Cl.

| | |
|---|---|
| *C07K 14/74* | (2006.01) |
| *A61K 40/11* | (2025.01) |
| *A61K 40/31* | (2025.01) |
| *A61K 40/32* | (2025.01) |
| *A61K 40/40* | (2025.01) |
| *C07K 14/705* | (2006.01) |
| *C07K 14/725* | (2006.01) |
| *C12N 5/0783* | (2010.01) |
| *C12N 9/12* | (2006.01) |

(52) U.S. Cl.
CPC ........ *C07K 14/70539* (2013.01); *A61K 40/11* (2025.01); *A61K 40/31* (2025.01); *A61K 40/32* (2025.01); *A61K 40/40* (2025.01); *C07K 14/705* (2013.01); *C07K 14/7051* (2013.01); *C12N 5/0636* (2013.01); *C12N 9/12* (2013.01); *C12Y 207/10002* (2013.01); *C07K 2319/02* (2013.01); *C07K 2319/03* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 6,056,952 | A | 5/2000 | Rosenberg |
| 6,268,411 | B1 | 7/2001 | Schneck et al. |
| 6,319,494 | B1 | 11/2001 | Capon et al. |
| 6,407,221 | B1 | 6/2002 | Capon et al. |
| 6,410,319 | B1 | 6/2002 | Raubitschek et al. |
| 7,741,465 | B1 | 6/2010 | Eshhar et al. |
| 7,871,817 | B2 | 1/2011 | Voss et al. |
| 8,450,112 | B2 | 5/2013 | Li et al. |
| 8,524,234 | B2 | 9/2013 | Getts et al. |
| 8,906,383 | B2 | 12/2014 | Peakman et al. |
| 2004/0258697 | A1 | 12/2004 | Brumeanu et al. |
| 2013/0287748 | A1 | 10/2013 | June et al. |
| 2014/0219975 | A1 | 8/2014 | June et al. |
| 2017/0166622 | A1 | 6/2017 | Baeuerle |
| 2018/0179260 | A1 | 6/2018 | Kuhns et al. |
| 2019/0345485 | A1 | 11/2019 | Kisielow |

FOREIGN PATENT DOCUMENTS

| | | |
|---|---|---|
| CA | 2104957 A1 | 9/1992 |
| CA | 2209300 A1 | 6/2011 |
| EP | 0574512 B1 | 12/1993 |
| EP | 1292621 B1 | 3/2003 |
| EP | 1379670 B1 | 1/2004 |
| EP | 2659893 A2 | 11/2013 |
| WO | WO2005054292 A1 | 6/2005 |
| WO | WO2011101681 A2 | 8/2011 |

(Continued)

OTHER PUBLICATIONS

Zanetti. Tapping CD4 T Cells for Cancer Immunotherapy: The Choice of Personalized Genomics. J Immunol Mar. 1, 2015, 194 (5) 2049-2056.

Perez, S. et al. Selective immunotargeting of diabetogenic CD4 T cells by genetically redirected T cells-Immunology 2014, 143, 609-617.

Eshhar, Zelig, Adoptive cell therapy of autoimmune diseases employing genetically T regulatory cells with redirected antibody specificity, International Conference on Emerging Cell Therapies, Oct. 1-3, 2012. J Cell Sci Ther 2012, 3:7 http://dx.doi.org/10.4172/2157-7013.S1.004.

Casares, S. et al. Engineering and characterization of a murine MHC class II-immunoglobulin chimera expressing an Immunodominant CD4 T viral epitope, Protein Eng. Nov. 1997; 10(11):1295-301.

(Continued)

*Primary Examiner* — Zachary S Skelding
(74) *Attorney, Agent, or Firm* — NGUYEN TARBET IP LAW

(57) ABSTRACT

Surrogate co-receptors for T cells, including T cells expressing chimeric receptors comprising major histocompatibility molecules grafted onto T cell receptor molecules. The surrogate co-receptors feature a portion of CD8, wherein the Ig domains of CD8 are replaced with Ig domains that confer novel specificities (e.g. antibody Fv fragments specific for a target of interest.) The surrogate co-receptors may be used to help enhance CRM$^{pMHC}$-CD3 signaling as part of a 5-module receptor system. The present invention also describes Lck fusions.

20 Claims, 3 Drawing Sheets

Specification includes a Sequence Listing.

(56) References Cited

FOREIGN PATENT DOCUMENTS

| WO | WO2014117121 A1 | 7/2014 | | |
| WO | WO2016070061 A1 | 5/2016 | | |
| WO | WO-2018075807 A1 * | 4/2018 | .............. | A61P 35/02 |
| WO | WO2020191328 A1 | 9/2020 | | |

OTHER PUBLICATIONS

Mottez, E. et al. Cells expressing a major histocompatibility complex class I molecule with a single covalently bound peptide are highly immunogenic. J. Exp. Med. vol. 181 Feb. 1995 493-502.

Willemsen, RA. et al., T Cell Retargeting with MHC Class I-Restricted Antibodies: The CD28 Costimulatory Domain Enhances Antigen-Specific Cytotoxicity and Cytokine Production1. J Immunol. Jun. 15, 2005;174(12):7853-8.

Dotti , Gianpietro, The Other Face of Chimeric Antigen Receptors, www.moleculartherapy.org vol. 22 No. 5 May 2014.

Bridgeman, John S. et al. The Optimal Antigen Response of Chimeric Antigen Receptors Harboring the CD3z Transmembrane Domain Is Dependent upon Incorporation of the Receptor into the Endogenous TCR/CD3 Complex. The Journal of Immunology, May 17, 2010.

Brien et al. "Key role of T cell defects in age-related vulnerability to West Nile virusT cell defects and age-related vulnerability to WNV." The Journal of experimental medicine 206.12 (2009): 2735-2745.

Casares, et al., Insights into the Pathogenesis of Type 1 Diabetes a Hint for Novel Immunospecific Therapies S, Current Molecular Medicine, vol. 1, No. 3, Jul. 1, 2001, pp. 357-378(22).

Casares, S. et al., Modulation of CD4 T cell function by soluble MHC II-peptide chimeras, Journal International Reviews of Immunology, vol. 20, 2001—Issue 5, pp. 547-573.

Davis MM, Bjorkman PJ. T-cell antigen receptor genes and T-cell recognition. Nature. 1988;334(6181):395-402. Epub Aug. 4, 1988. doi: 10.1038/334395a0. PubMed PMID: 3043226.

Fantini et al. In vitro generation of CD4+ CD25+ regulatory cells from murine naive T cells. Nature protocols. 2007;2(7):1789-94. doi: 10.1038/nprot.2007.258. PubMed PMID: 17641646.

Dotti et al. Current status of genetic modification of T cells for cancer treatment—Cytotherapy, 2005; 7(3):262-72.

Hammad et al. Dendritic cells and epithelial cells: linking innate and adaptive immunity in asthma. Nat Rev Immunol. 2008;8(3):193-204. doi: 10.1038/nri2275. PubMed PMID: 18301423.

Hammad et al. Inflammatory dendritic cells—not basophils—are necessary and sufficient for induction of Th2 immunity to inhaled house dust mite allergen. J Exp Med. 2010;207(10):2097-111. doi: 10.1084/jem.20101563. PubMed PMID: 20819925; PMCID: 2947072.

Harris et al. Prediction of murine MHC class I epitopes in a major house dust mite allergen and induction of T1-type CD8+ T cell responses. Int Immunol. 1997;9(2):273-80. PubMed PMID: 9040009.

Kuhns et al. "Piecing together the family portrait of TCR-CD 3 complexes." Immunological reviews 250.1 (2012):120-143.

Kuhns et al. Deconstructing the Form and Function of the TCR/CD3 Complex. Immunity. 2006;24(2):133-9. PubMed PMID: 16473826.

Kuhns et al. "TCR signaling emerges from the sum of many parts." Frontiers in immunology 3 (2012): 159.

Lambrecht et al. "The immunology of asthma." Nature immunology 16.1 (2015): 45-56.

Mathis et al. "Levees of immunological tolerance." Nature immunology 11.1 (2010): 3-6.

Maus et al. Antibody-modified T cells: CARs take the front seat for hematologic malignancies. Blood. 2014;123(17):2625-35. doi: 10.1182/blood-2013-11-492231. PubMed PMID: 24578504; PMCID: 3999751.

Meyers et al. "TIM-4 is the ligand for TIM-1, and the TIM-1-TIM-4 interaction regulates T cell proliferation." Nature Immunology 6.5 (2005): 455-464.

Moon et al. "Naive CD4+ T cell frequency varies for different epitopes and predicts repertoire diversity and response magnitude." Immunity 27.2 (2007): 203-213.

Savoldo et al. "Chimeric antigen receptors (CARs) from bench-to-bedside." Immunology letters 155.1-2 (2013):40-42.

Uttenthal et al. Challenges in T cell receptor gene therapy. The journal of gene medicine 14.6 (2012): 386-399.

Vercelli, Donata. "Discovering susceptibility genes for asthma and allergy." Nature reviews immunology 8.3 (2008): 169-182.

Willart et al. "Interleukin-1α0 controls allergic sensitization to inhaled house dust mite via the epithelial release of GM-CSF and IL-33." Journal of Experimental Medicine 209.8 (2012): 1505-1517.

Willemsen, RA et al. A phage display selected Fab fragment with MHC class I-restricted specificity for MAGE-A1 allows for retargeting of primary human T lymphocytes, Gene Therapy 8, 1601-1608 (2001).

Wu, Hsin-Jung, et al. "Gut-residing segmented filamentous bacteria drive autoimmune arthritis via T helper 17 cells." Immunity 32.6 (2010): 815-827.

Qian, Z et al. Engineered T regulatory Cells Co-expressing MHC Class II:peptide Complexes Are Efficient Inhibitors of Autoimmune T Cell Function and Prevent the Development of Autoimmune Arthritis. J. Immunol. Author manuscript. Jun. 1, 2014, vol. 190; pp. 1-23; abstract; p. 3, fifth paragraph-p. 4, first paragraph; p. 6, fourth paragraph; doi:1 OA049/jimmunol. 1300024.

Thiel, Markus, et al. "Efficiency of T-cell costimulation by CD80 and CD86 cross-linking correlates with calcium entry." Immunology 129.1 (2010): 28-40.

Bueno, Clara, et al. "T cell signalling induced by bacterial superantigens." Superantigens and Superallergens 93 (2007): 161-180.

Podojil et al. "Molecular mechanisms of T-cell receptor and costimulatory molecule ligation/blockade in autoimmune disease therapy." Immunological reviews 229.1 (2009): 337-355.

Jackson et al. "Targeting CD8+ T-cell tolerance for cancer immunotherapy." Immunotherapy 6.7 (2014): 833-852.

Zanetti, Maurizio. "Tapping CD4 T cells for cancer immunotherapy: the choice of personalized genomics." The Journal of Immunology 194.5 (2015): 2049-2056.

Brogdon, Jennifer, et al. "A site for CD4 binding in the β1 domain of the MHC class II protein HLA-DR1." The Journal of Immunology 161.10 (1998): 5472-5480.

Bäckström, B. Thomas, et al. "A motif within the T cell receptor α chain constant region connecting peptide domain controls antigen responsiveness." Immunity 5.5 (1996): 437-447.

Trowsdale, John, and Julian C. Knight. "Major histocompatibility complex genomics and human disease." Annual review of genomics and human genetics 14 (2013): 301-323.

Le Franc et al. ("The T cell receptor Facts Book," pp. ix, 3-397 (2001)) . (Year: 2001).

Li et al. "Structural and biophysical insights into the role of CD4 and CD8 in T cell activation." Frontiers in immunology 4 (2013): 206.

Liu et al., "Major histocompatibility complex: Interaction with peptides." eLS. John Wiley & Sons, Ltd: Chichester. (2011) pp. 1-12. (Year: 2011).

Macian, Fernando. "NFAT proteins: key regulators of T-cell development and function." Nature Reviews Immunology 5.6 (2005): 472-484.

Painter et al.. "Conformational variation in structures of classical and non-classical MHCII proteins and functional Implications." Immunological reviews 250.1 (2012): 144-157.

Xu et al. "A membrane-proximal tetracysteine motif contributes to assembly of CD30δε and CD3γε dimers with the T cell receptor." Journal of Biological Chemistry 281.48 (2006): 36977-36984.

Yin et al. "Crystal structure of a complete ternary complex of T-cell receptor, peptide-MHC, and CD4." Proceedings of the National Academy of Sciences 109.14 (2012): 5405-5410.

Wucherpfennig, Kai W., et al. "Structural biology of the T-cell receptor: insights into receptor assembly, ligand recognition, and initiation of signaling." Cold Spring Harbor perspectives in biology 2.4 (2010): a005140.

Devine, Lesley, et al. "Mapping the binding site on CD8β for MHC class I reveals mutants with enhanced binding." The Journal of Immunology 177.6 (2006): 3930-3938.

(56) References Cited

OTHER PUBLICATIONS

Choi et al. "Chimeric protein of CD8a extracellular domain and CD4 transmembrane and cytoplasmic domain binds more efficiently to p56lck than CD8a." Korean Journal of Biological Sciences 3.3 (1999): 331-336.

Sharpe et al. Genetically modified T cells in cancer therapy: opportunities and challenges. Dis Model Mech. Apr. 2015; 8(4): 337-350.

* cited by examiner

*FIG. 2*
*FIG. 3*
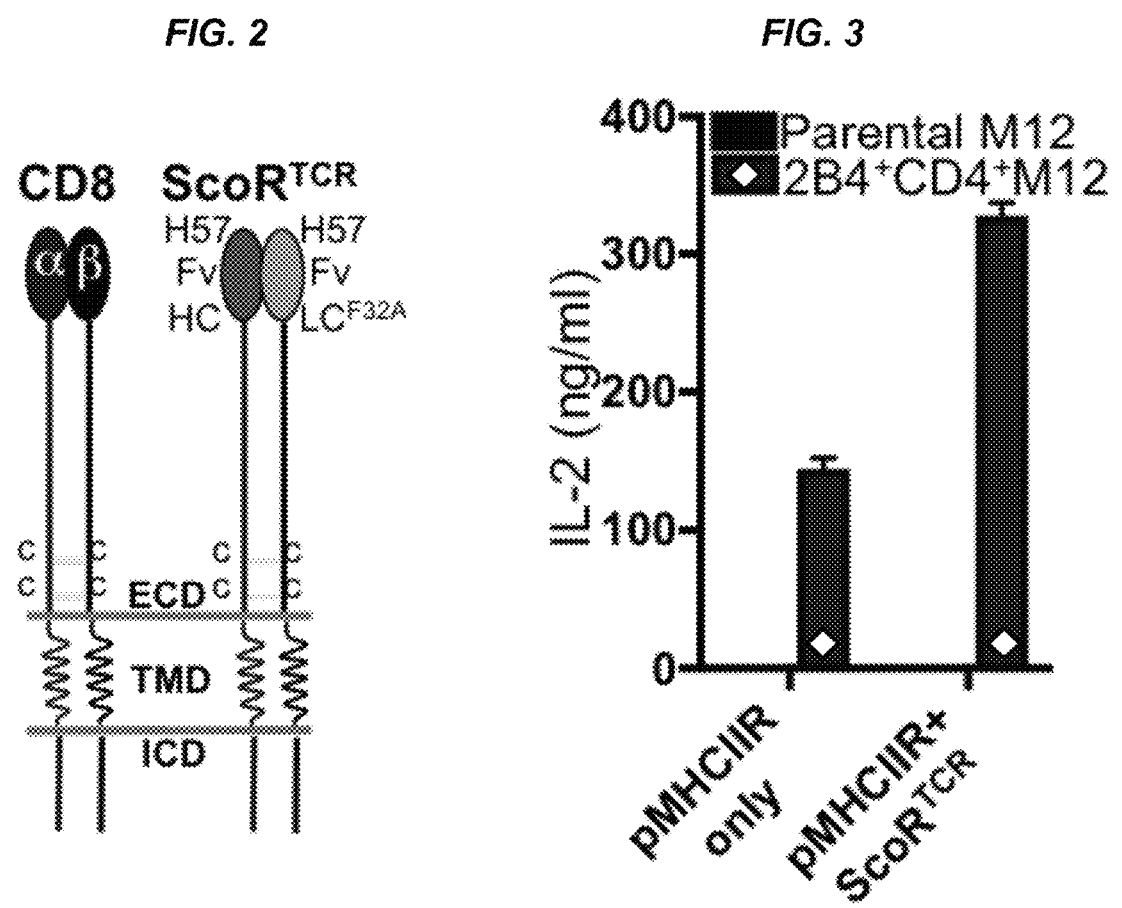
*FIG. 4*
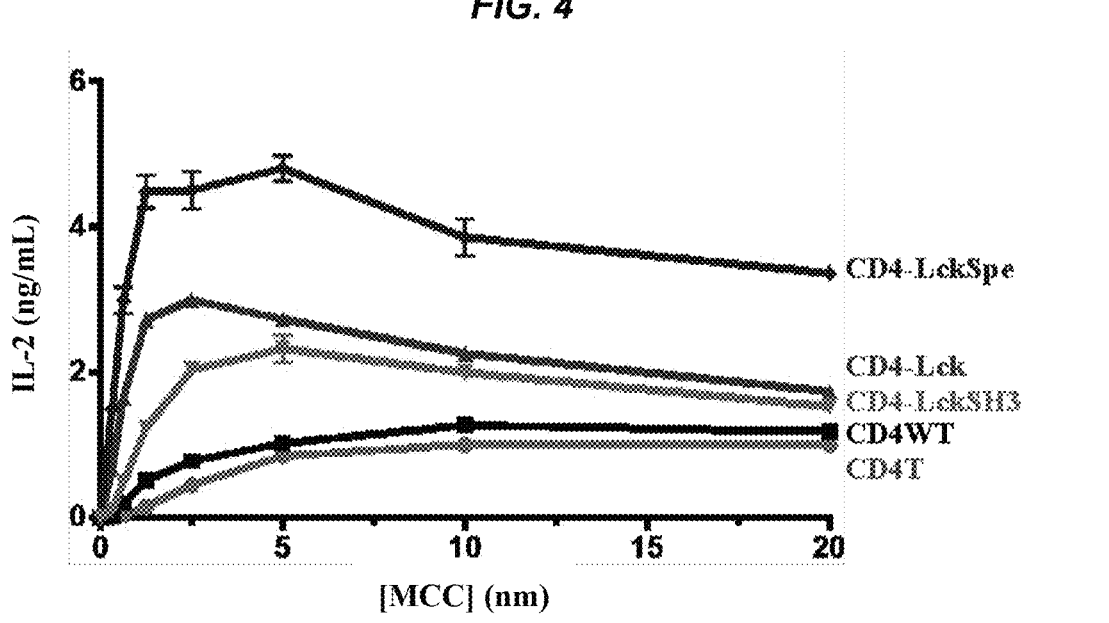

Legend:
- ■ MCC:I-E$^k$ (agonist)
- ▨ T102S:I-E$^k$ (weak agonist)
- ▨ T102G:I-E$^k$ (antagonist)
- ▨ Hb:I-E$^k$ (null)
- ▨ MCC4A:I-E$^k$ (shaved peptide)

Legend:
- ■ Specific Target
- ▨ Control Target

SURROGATE CO-RECEPTORS FOR T CELLS AND METHODS OF USE

CROSS-REFERENCES TO RELATED APPLICATIONS

This application is a continuation-in-part and claims benefit of PCT Application No. PCT/US20/23942, filed Mar. 20, 2020, which claims benefit of U.S. Provisional Patent Application No. 62/821,222 filed Mar. 20, 2019, the specification(s) of which is/are incorporated herein in their entirety by reference.

This application is a continuation-in-part and claims benefit of U.S. patent application Ser. No. 17/345,425, filed Jun. 11, 2021, which is a Divisional application of Ser. No. 15/738,467, filed Dec. 20, 2017, now U.S. Pat. No. 11,059, 880, which is a 371 application of PCT Application No. PCT/US16/40177, filed Jun. 29, 2016, which claims benefit of U.S. Provisional Patent Application No. 62/186,865 filed Jun. 30, 2015, the specification(s) of which is/are incorporated herein in their entirety by reference.

STATEMENT REGARDING FEDERALLY SPONSORED RESEARCH OR DEVELOPMENT

This invention was made with government support under Grant No. R01 A1101053, awarded by National Institutes of Health. The government has certain rights in the invention.

REFERENCE TO A SEQUENCE LISTING

Applicant asserts that the information recorded in the form of an Annex C/ST.25 text file submitted under Rule 13ter.1(a), entitled UNIA_19_03_PCT_CIP_Sequence_Listing_ST25, is identical to that forming part of the international application as filed. The content of the sequence listing is incorporated herein by reference in its entirety.

FIELD OF THE INVENTION

The present invention relates to T cells and T cell receptors, more particularly to co-receptors for engineered T cells, such as T cells expressing components of a modular chimeric receptor system.

BACKGROUND OF THE INVENTION

T cells normally recognize and respond to peptide antigens embedded within major histocompatibility complex molecules (pMHCs) of antigen presenting cells (APCs) via their TCR-CD3 complex. This TCR-CD3 complex is composed of the TCR, which is the receptor module that binds the pMHC. and the CD3γε, CD3δε, and CD3ζζ signaling modules that connect the TCR to the intracellular signaling machinery. The intracellular domains of the CD3ζ subunits contain immunoreceptor tyrosine-based activation motifs (ITAMs) that are phosphorylated by the Src kinases, e.g., Lck, Fyn. CD3γ, CD3δ, and CD3ε each contain one ITAM while CD3ζ contains three ITAMs for a total of ten in a single complex. The 4-module TCR-CD3 complex does not have any intrinsic Src kinase activity. In fact, coreceptor modules (e.g., CD4, CD8) appear to sequester Lck away from the TCR-CD3 complex until both a coreceptor and a TCR bind a pMHC. The Lck associated with the coreceptor is then brought into close proximity to the CD3 ITAMs to phosphorylate tyrosines within these motifs and initiate signaling.

Ectopic T cell receptors (ectopic TCRs) have been introduced into T cells in an effort to reprogram or alter T cell specificity. However, in some cases, the introduction of ectopic TCRs has been found to lead to cross-pairing events with endogenous TCRs, resulting in novel TCRs with auto-immune specificities. This led to the use of chimeric antigen receptors (referred to herein as one-module CARs or $^{1M}$CARs), which are typically designed with (a) an extracellular domain consisting of a single-chain variable fragment (scFv) of a monoclonal antibody directed against a target antigen; (b) a transmembrane domain that does not mediate interactions with other protein subunits; and (c) an intracellular domain consisting of the CD3 intracellular signaling domain as well as signaling domains from a variety of other signaling molecules (e.g., CD28, CD27, ICOS, 4-1BB, OX40). However, $^{1M}$CARs bear little resemblance to naturally evolved receptors. Signal initiation most likely occurs via random receptor clustering and recruitment of kinases to their signaling motifs as $^{1M}$CARs lack the more complex mechanisms that natural receptors have evolved to initiate signaling. Indeed, $^{1M}$CARs are orders of magnitude less sensitive than their natural counterparts, treatment requires the infusion of supra-physiological numbers of $^{1M}$CAR-T cells, and cytokine release syndrome (CRS) is a common side effect. The success of $^{1M}$CAR-T cell therapy is largely limited to CD19$^+$ hematopoietic tumors.

BRIEF SUMMARY OF THE INVENTION

The present invention describes biomimetic five module chimeric receptors (hereinafter referred to as ($^{5M}$CARs), which feature a chimeric receptor module (CRM) which, in one example, comprises a portion of the TCR and a portion of a MHC molecule such as a Class I, Class II, or non-classical MHC (also referred to herein as "CRM$^{MHC}$"), etc., three CD3 signaling modules (e.g., CD3γε, CD3δε, and CD3ζζ, which connect the TCR to the intracellular signaling machinery), and one surrogate co-receptor module (e.g., the a surrogate co-receptor would mirror the function of CD4 and CD8). In some embodiments, the CRM comprises a portion of a peptide antigen presented in the MHC and is referred to as CRM$^{pMHC}$ (aka "pMHCR"). For reference, FIG. 1A shows an example of the natural signaling machinery. FIG. 1B shows a model of a CAR comprising a CRM$^{pMHC}$ and three CD3 molecules (CD8 is not shown). The CRMs (e.g., CRM$^{pMHC}$) are adapted to recognize and bind to appropriate (specific) TCRs.

The present invention features a surrogate co-receptor (SCoR). In some embodiments the SCoR comprises a first chain comprising a portion of a T-cell co-receptor linked to a C-terminal of a first binding portion. In some embodiments, the portion of the T-cell co-receptor comprises at least a portion of a CD8 chain, a portion of a CD4 chain or a combination thereof. In some embodiments, the first binding portion is an Ig domain against a particular target. In certain embodiments, the SCoR comprises a second chain comprising a portion of a T-cell co-receptor linked to a C-terminal of a second binding portion. In some embodiments, the portion of the T-cell co-receptor comprises at least a portion of a CD8 chain, a portion of a CD4 chain or a combination thereof. In some embodiments, the second binding portion is an Ig domain against a particular target. In some embodiments, the second chain of the SCoR is linked to the first chain of the SCoR via a disulfide bond between an extracellular domain (ECD) portion of the t-cell co-receptor of the first chain and an ECD portion of the T-cell co-receptor of the second chain.

More specifically, the present invention features surrogate co-receptors (SCoRs), which may be featured as part of a $^{5M}$CAR. In some embodiments, the SCoRs comprise a portion of CD8. For example, the SCoRs of the present invention may comprise an Fv antibody portion linked to a portion of CD8. The present invention is not limited to CD8 and also includes SCoRs comprising other co-receptor molecules such as a portion of CD4 linked to a single chain Fv fragment. The present invention is not limited to the aforementioned SCoR components.

The present invention also features co-receptor fusions, wherein the SCoR is fused directly or indirectly to a Src kinase such as Lck.

The present invention also features cells, expressing the co-receptors (SCoRs) herein. The present invention also features cells expressing $^{5M}$CARs that feature the co-receptors (SCoRs) herein. Cells expressing a $^{5M}$CAR (e.g., with a CRM) may herein be referred to as "redirected cells." Redirected cells, e.g., redirected T cells, expressing a CRM$^{pMHC}$ would mimic antigen presenting cells (APCs). In some cases, binding of a TCR of a target T cell to the CRM$^{pMHC}$ of the redirected cell may then result in destruction of the target T cell by the redirected T cell; thus, in this case, the redirected cells may function as "anti-T cell" T cells. The present invention is not limited to redirected cells functioning to destroy a target. For example, in some embodiments, the redirected cell is adapted to help reprogram a target cell, e.g., the redirected cell may deliver instructions to the target cell.

The present invention features surrogate co-receptors (SCoRs). In some embodiments, the surrogate co-receptor (SCoR) comprises a CD8α chain and a CD8β chain. The CD8α chain comprises a first binding portion and a CD8α portion, wherein the first binding portion is an immunoglobulin (Ig) domain (e.g., an antibody fragment for a particular target antigen or the ligand binding region of a cell surface receptor such as CD80) and the CD8α portion is at least a portion of CD8α. The CD8β chain comprises a second chain comprising a second binding portion and a CD8β portion, wherein the second binding portion is an Ig domain (e.g., an antibody fragment for a particular target antigen or the receptor binding region of CD80) and the CD8β portion is at least a portion of CD8β.

In some embodiments, the antibody fragments are antibody Fv fragments. For example, the combination of the heavy and light chains of the Fv antibody fragments creates specificity for an epitope of an antibody. It is to be understood that the present invention is not limited to Ig domains from an antibody, and that the invention can include Fv from any antibody specific for any antigen. In some embodiments, the CD8 portions are linked C-terminal to the binding portions. In some embodiments, the CD8 portions are indirectly linked to the binding portions. In some embodiments, the CD8 portions are directly linked to the binding portions.

In some embodiments, the antibody fragments are wild type fragments. In some embodiments, the antibody fragments are from a particular standard antibody. In some embodiments, the antibody fragments have at least one mutation compared to their wild type sequences (or standard antibody sequences). In some embodiments, the antibody fragments with at least one mutation have a lower binding affinity than their wild type counterparts. In some embodiments, the antibody fragments have a germline sequence. The antibody fragments may be derived from a tuning process to modify or select particular binding kinetics via mutagenesis.

The present invention features surrogate co-receptor (SCoR) fusions (fusion molecules). In some embodiments, the fusion molecule comprises a SCoR of the present invention linked directly or indirectly to Lck. In some embodiments, the CD4 intracellular domain (ICD) (e.g., at least a portion of, or all) is used to replace at least a portion of the native CD8 ICD (e.g., CD8a ICD) in a 008-based SCoR. In some embodiments, at least a portion of the CD4 ICD and at least a portion of the transmembrane domain (TM) are used to replace at least a portion of the native 008 ICD and CD8 TM domain (respectively) in a CD8-based SCoR.

In some embodiments, the present invention features engineered cells expressing on their surface a SCoR of the present invention. In other embodiments, the present invention features engineered cells expressing on their surface a SCoR and a fusion molecule of the present invention.

The present invention also features engineered cells co-expressing on their surface: a chimeric receptor (CRM) comprising a major histocompatibility complex (MHC) portion derived from an MHC protein directly or indirectly fused to a T cell receptor (TCR) portion derived from a TCR protein, wherein the CRM contains a peptide antigen in the MHC (CRM$^{pMHC}$) that confers upon it specificity for a first epitope of a TCR; and a surrogate coreceptor according to the present invention, wherein the SCoR is specific for a second epitope of the TCR. In some embodiments, the engineered cells also express a fusion molecule of the present invention.

In some embodiments, the MHC portion of the CRM is N-terminal to the TCR portion of the CRM. In some embodiments, the MHC portion is indirectly fused to the TCR portion via a linker. In some embodiments, the TCR portion comprises at least a portion of a transmembrane domain of the TCR protein and the MHC portion comprises at least a portion of an extracellular domain of the MHC protein. In some embodiments, the TCR portion comprises at least a portion of a transmembrane domain and at least a portion of a cytoplasmic domain of a TCR protein, and the MHC portion comprises at least a portion of an extracellular domain of the MHC protein. In some embodiments, the CRM further comprises a peptide antigen integrated into the MHC portion, or directly or indirectly fused to the MHC portion. In some embodiments, the MHC protein comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a fragment thereof, or a combination thereof. In some embodiments, the MHC molecule comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a peptide that is at least 90% identical to HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, or H2-EK beta, a fragment thereof, or a combination thereof. In some embodiments, the TCR molecule comprises TRAC, TRBC1, TRBC2, TRDC, TRGC1, TRGC2, TCRA, TCB1, TCB2, TCC1, TCC2, TCC3, TCC4, a fragment thereof, or a combination thereof. In some embodiments, the TCR molecule comprises TRAC, TRBC1, TRBC2, TRDC, TRGC1, TRGC2, TCRA, TCB1, TCB2, TCC1, TCC2, TCC3, TCC4, a peptide that is at least 90% identical to TRAC, TRBC1, TRBC2, TRDC, TRGC1, TRGC2, TCRA, TCB1, TCB2, TCC1, TCC2, TCC3, or TCC4, a fragment thereof, or a combination thereof.

In some embodiments, the CRM can complex with a CD3 subunit. In some embodiments, the engineered cell further co-expresses a SCoR. In some embodiments, the engineered cell further co-expresses a second fusion molecule.

The present invention also features vectors encoding surrogate co-receptors according to the present invention. The present invention also features DNA sequences encoding surrogate co-receptors according to the present invention. The present invention also features protein sequences encoding surrogate co-receptors according to the present invention. The present invention also features vectors encoding fusion molecules according to the present invention. The present invention also features DNA sequences encoding fusion molecules according to the present invention. The present invention also features protein sequences encoding fusion molecules according to the present invention.

The present invention also features methods for eliminating or redirecting a target cell. In some embodiments, the method comprises introducing a genetically engineered cell according to the present invention, wherein the CRM of the genetically engineered cell is specific for a TCR of the target cell, wherein upon binding of the CRM of the genetically engineered cell to the TCR of the target cell, the genetically engineered cell (a) initiates a signaling cascade that eliminates the target cell, or (b) instructs the target cell to differentiate to a specific effector function.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

FIG. 2 shows an example of a surrogate co-receptor (SCoR) featuring a portion of CD8. More specifically, the SCoR comprises the Fv regions of the anti-mTCRβ mAb H57-597 (H57) fused to the stalks of CD8αβ. The CD8α Ig domain was replaced with the H57 heavy chain (HC), and the CD8β Ig domain was replaced with the light chain (LC).

FIG. 3 shows IL-2 expression in cells expressing a surrogate co-receptor with a F32A mutant on the H57 light chain (LC) ($SCoR^{TCR}$) with the MCC:I-E$^k$ pMHCIIR on $58α^-β^-$ cells. The pMHCIIR$^+$ $SCoR^{TCR+}$ cells made more IL-2 than pMHCIIR$^+$ cells when co-incubated with M12 B cells expressing the 2B4 TCR, CD4, and truncated CD3 subunits (CD3T) that lack ITAMs. The TCR-CD3 complexes cannot signal, and M12 cells do not make IL-2, therefore the pMHCIIR-CD3 complexes signal more with this $SCoR^{TCR}$ than without.

FIG. 4 shows IL-2 expression from $58α^-β^-$ cells ($58α^-β^-$ T cell hybridomas) expressing the 5c.c7 TCR and indicated CD4-Lck fusions after 16 hours of co-culture with peptide-pulsed APCs.

Figure 1A:
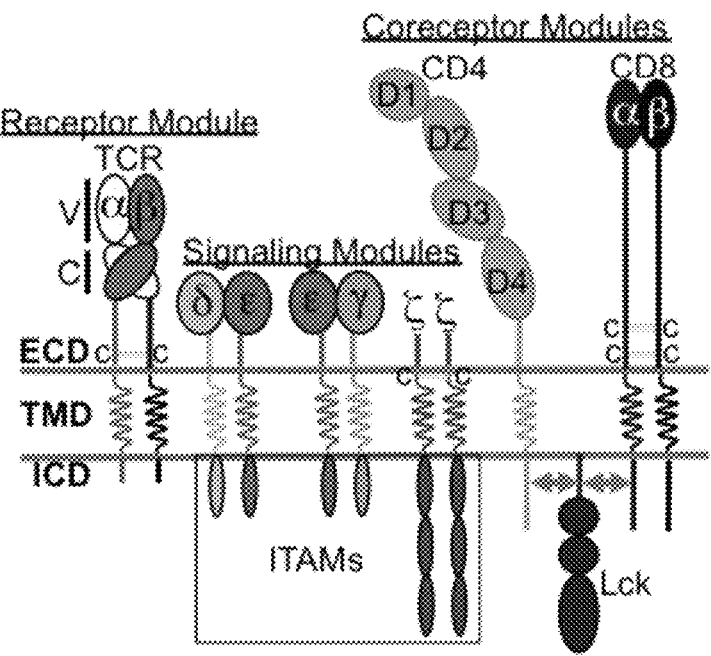
FIG. 1A shows an example of the natural signaling machinery.
Figure 1B:
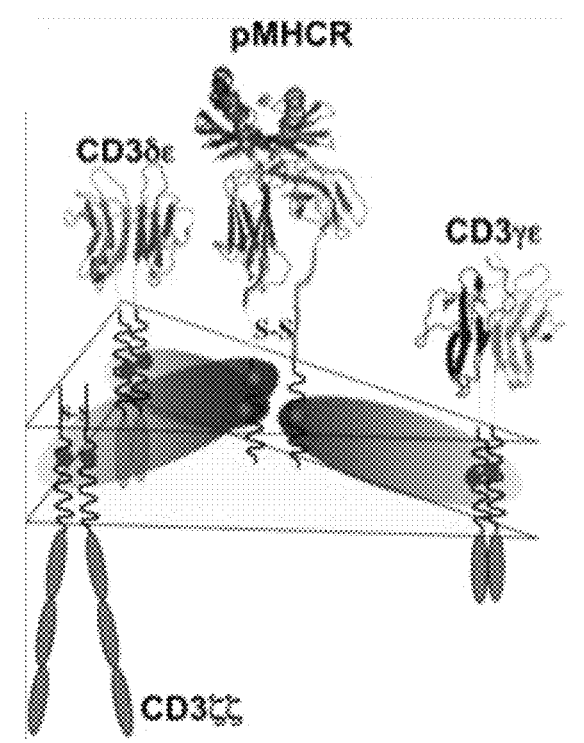
FIG. 1B shows an example of a CAR comprising a $CRM^{pMHC}$ (aka pMHCR) and three CD3 molecules (CD8 is not shown).
Figure 5:
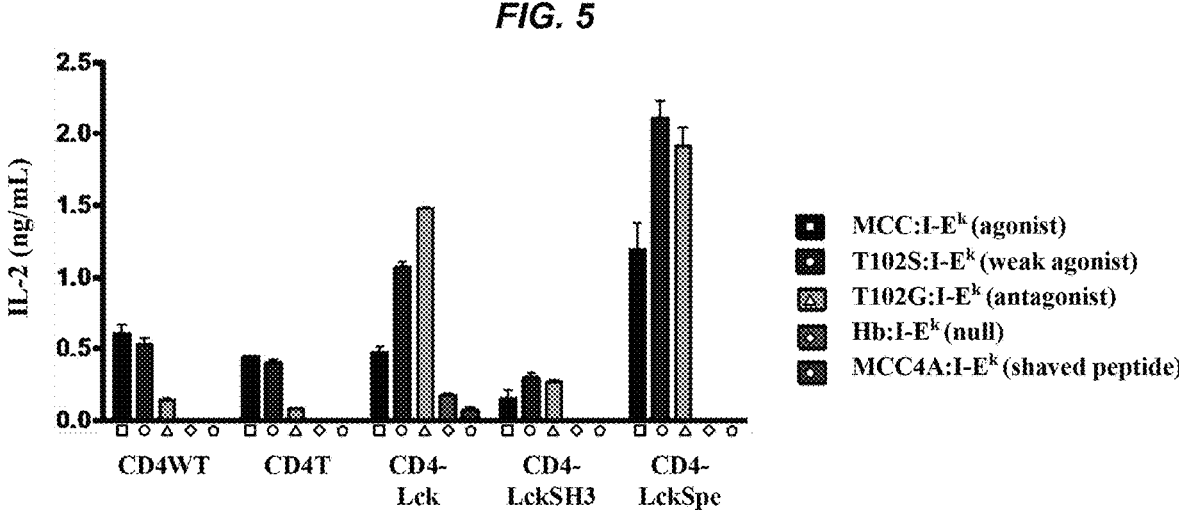

FIG. 5 shows IL-2 expression from $58α^-β^-$ cells ($58α^-β^-$ T cell hybridomas) expressing the 5c.c7 TCR and indicated CD4-Lck fusions after 16 hours of co-culture with APCs expressing high density single-species agonist, weak agonist, antagonist, shaved or null tethered pMHC.

Figure 6:
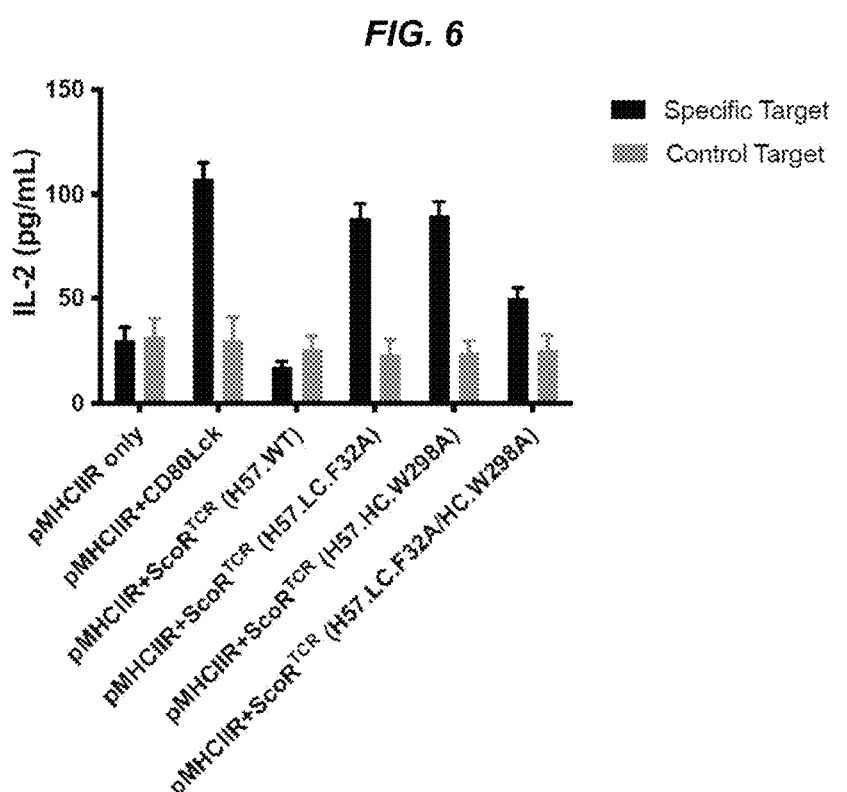

FIG. 6 shows IL-2 production by T-cell hybridomas (58a-b-) expressing a pMHCIIR (aka CRM) built with MCC:I-E$^k$ and the original CD80-Lck SCoR or with the new SCoR TCR built with either the original high affinity H57 WT, or mutants designed to lower the affinity of the H57 for the TCR. These mutants are the H57 light chain (LC) F32A or the H57 heavy chain (HC) W298A. The bars show the mean IL-2 produced by $2.5×10^4$ T-cell hybridomas (58a-b-)+1-SEM responding to M12 target cells expressing either the specific TCR or a negative control TCR for data from 3 independent experiments aggregated together. These data show that the WT high affinity H57 does not enhance IL-2 production driven by the pMHCIIR (CRM), while lowering the affinity by mutating the LC or HC does cause these SCoRs to increase pMHCIIR-driven IL-2 production.

DETAILED DESCRIPTION OF THE INVENTION

It is to be noted that $CRM^{MHC}$ and MHCR are interchangeable and both refer to a chimeric receptor that is comprised of a portion of the TCR and a portion of an MHC molecule. Additionally, $CRM^{pMHC}$ and pMHCR are also interchangeable, both referring to a $CRM^{MHC}$ with a portion of a peptide antigen presented within the context of the MHC portion.

Referring now to FIG. 1-6, the present invention features surrogate co-receptors (SCoRs), such as SCoRs comprising at least a portion of CD8. For example, the SCoRs of the present invention comprise an Fv antibody portion linked to a portion of CD8. The present invention is not limited to CD8 and also includes SCoRs comprising at least a portion of CD4, e.g., a single chain Fv antibody fragment linked to a portion of CD4. In a non-limiting embodiment, the light chain and/or heavy chain Fv regions are placed separately on the CD8 alpha or beta chains so that they form a heterodimer. In some embodiments, the SCoRs of the present invention may be featured as part of the $^{5M}$CARs.

The present invention also features co-receptor fusions, wherein a SCoR is fused to a Src kinase (such as Lck) or to portions of the CD4 intracellular domain that would increase association with Lck.

The present invention also features cells, such as T cells, expressing SCoRs of the present invention. The present invention also features cells, such as T cells, expressing $^{5M}$CARs featuring SCoRs of the present invention.

The present invention features a surrogate co-receptor (SCoR). In some embodiments the SCoR comprises a first chain comprising a portion of a T-cell co-receptor linked to a C-terminal of a first binding portion. In some embodiments, the portion of the T-cell co-receptor comprises at least a portion of a CD8 chain, a portion of a CD4 chain or a combination thereof. In some embodiments, the first binding portion is an Ig domain against a particular target. In certain embodiments, the SCoR comprises a second chain comprising a portion of a T-cell co-receptor linked to a C-terminal of a second binding portion. In some embodiments, the portion of the T-cell co-receptor comprises at least a portion of a CD8 chain, a portion of a CD4 chain or a combination thereof. In some embodiments, the second binding portion is an Ig domain against a particular target. In some embodiments, the second chain of the SCoR is linked to the first chain of the SCoR via a disulfide bond between an extracellular domain (ECD) portion of the t-cell co-receptor of the first chain and an ECD portion of the T-cell co-receptor of the second chain.

The present invention may also feature a surrogate co-receptor (SCoR) comprising a first chain and a second chain. In some embodiments, the first chain comprises a portion of a T-cell co-receptor linked to the C-terminal of a first binding portion. In some embodiments, the second chain comprises a portion of a T-cell co-receptor linked to the C-terminal of a second binding portion. In some embodiments, the portion of the T-cell co-receptors comprise at least a portion of a CD8 chain, a portion of a CD4 chain or a combination thereof. In some embodiments, the first binding portion is an Ig domain against a particular target. In other embodiments, the second binding portion is an Ig domain against a particular target.

The present invention also features a surrogate co-receptor (SCoR) comprising a portion of a T-cell co-receptor linked to the C-terminal of a binding portion. In some embodiments, the portion of the T-cell co-receptor comprises at least a portion of a CD4 chain. In other embodiments, the binding portion is an Ig domain against a particular target.

The present invention may further feature a surrogate co-receptor (SCoR) comprising an a chain and a β chain. In some embodiments, the α chain comprises a first binding portion and a CD8α portion, wherein the first binding portion is an Ig domain against a particular target and the first CD8α portion is at least a portion of a CD8α chain. In some embodiments, the β chain comprises a second binding portion and a CD8β portion, wherein the second binding portion comprises an Ig domain against a particular target and the CD8β portion is at least a portion of a CD8β chain. In some embodiments, the CD8 portions are linked C-terminal to the respective binding portions. In some embodiments, the β chain of the SCoR is linked to the α chain of the SCoR via a disulfide bond between an extracellular domain (ECD) portion of the t-cell co-receptor of the α chain and an ECD portion of the T-cell co-receptor of the β chain.

In some embodiments, the CD8 chain comprises a CD8α chain, a CD8β chain or a combination thereof. In some embodiments, the CD8 chain or the CD4 chain comprises a portion of an extracellular domain (ECD), a portion of a transmembrane domain (TMD), a portion of an intracellular domain (ICD), or a combination thereof. In some embodiments, the ECD of CD4 comprises a D1 domain, a D2 domain, a D3 domain, a D4 domain, or a combination thereof. In certain embodiments, the first binding portion replaces the D1 domain of the ECD of CD4. In some embodiments, the portion of the CD8 or the portion of the CD4 chain further comprise a Lck protein fused to or replacing an intracellular domain (ICD). In some embodiments, the portion of the CD8 or the portion of the CD4 are directly linked or indirectly linked to the respective binding portions.

In some embodiments, the Ig domains are from a CD80 ligand binding region, a CD86 ligand binding region, or a combination thereof. In other embodiments, the Ig domains are antibody fragments. In some embodiments, the antibody fragments are antibody Fv fragments. In some embodiments, the antibody Fv fragments are heavy chain domains, light chain domains or a combination thereof.

In some embodiments, the present invention features an engineered cell expressing on its surface at least one surrogate co-receptor as described herein. In other embodiments, the present invention features an engineered cell co-expressing on its surface at least one chimeric receptor (CRM) and at least one SCoR as described herein. In some embodiments, the CRM comprises a major histocompatibility complex (MHC) portion comprised of at least a portion of an extracellular domain of an MHC protein fused to the N-terminal of a T cell receptor (TCR) portion, comprised of at least a portion of a transmembrane domain and at least a portion of a cytoplasmic domain of a TCR protein.

I. $^{5M}$CARs with Chimeric MHC Receptors (CRMs)

As previously discussed, the surrogate co-receptors (SCoRs) of the present invention may be featured as part of $^{5M}$CARs (e.g., as part of $^{5M}$CARs with chimeric MHC receptors, e.g., CRMs, CRM$^{pMHC}$, etc.). The CRMs described herein comprise an MHC portion (e.g., class I, class II, non-classical, a combination thereof, etc.) and a TCR portion (e.g., αβ, γδ TCR, etc.). In some embodiments, the MHC portion and TCR portion are separated by a linker, e.g., peptide linker. In some embodiments, the CRM further comprises a peptide antigen (a CRM comprising a peptide antigen may herein be referred to as a pMHCR or CRM$^{pMHC}$). Note that MHC portions and/or TCR portions may be from any appropriate species including but not limited to human, monkey, mouse, rat, rabbit, or the like, e.g., any other appropriate mammalian species.

a. MHC Portion of CRMs

The MHC portion may comprise one or more MHC peptides (e.g., HLA-A, HLA-B, HLA-C, HLA-DPA1, HLA-DPB1, HLA-DQA1, HLA-DQB1, HLA-DRA, HLA-DRB1), one or more fragments thereof, or combinations thereof. For reference, non-limiting MHC sequences (human, mouse) are listed below in Table 1.1 and Table 1.2. Note that MHC genes are highly polymorphic, and thus the present invention is not limited to the sequences in Table 1.1 and Table 1.2. The present invention includes MHC polymorphisms and any other appropriate variant of MHC proteins.

TABLE 1.1

Examples of Human MHC Protein Sequences

| SEQ ID NO. | Description | Amino Acid Sequence |
|---|---|---|
| 1 | Uniprot P01891 HLA-A gene (MHC I) | MAVMAPRTLVLLLSGALALTQTWAGSHSMRYFYTSVSRPGRGEP RFIAVGYVDDTQFVRFDSDAASQRMEPRAPWIEQEGPEYWDRN TRNVKAQSQTDRVDLGTLRGYYNQSEAGSHTIQMMYGCDVGSD GRFLRGYRQDAYDGKDYIALKEDLRSWTAADMAAQTTKHKWEA AHVAEQWRAYLEGTCVEWLRRYLENGKETLQRTDAPKTHMTHH AVSDHEATLRCWALSFYPAEITLTWQRDGEDQTQDTELVETRPA GDGTFQKWVAVVVPSGQEQRYTCHVQHEGLPKPLTLRWEPSSQ PTIPIVGIIAGLVLFGAVITGAVVAAVMWRRKSSDRKGGSYSQAAS SDSAQGSDVSLTACKV |

TABLE 1.1-continued

Examples of Human MHC Protein Sequences

| SEQ ID NO. | Description | Amino Acid Sequence |
|---|---|---|
| 2 | Uniprot P18464<br>HLA-B gene<br>(MHC I) | MRVTAPRTVLLLLWGAVALTETWAGSHSMRYFYTAMSRPGRGEP<br>RFIAVGYVDDTQFVRFDSDAASPRTEPRAPWIEQEGPEYWDRNT<br>QIFKTNTQTYRENLRIALRYYNQSEAGSHTWQTMYGCDVGPDG<br>RLLRGHNQYAYDGKDYIALNEDLSSWTAADTAAQITQRKWEAAR<br>EAEQLRAYLEGLCVEWLRRHLENGKETLQRADPPKTHVTHHPVS<br>DHEATLRCWALGFYPAEITLTWQRDGEDQTQDTELVETRPAGDR<br>TFQKWAAVVVPSGEEQRYTCHVQHEGLPKPLTLRWEPSSQSTIP<br>IVGIVAGLAVLAVVVIGAVVATVMCRRKSSGGKGGSYSQAASSDS<br>AQGSDVSLTA |
| 3 | Uniprot Q29963<br>HLA-C gene<br>(MHC I) | MRVMAPRTLILLLSGALALTETWACSHSMRYFDTAVSRPGRGEP<br>RFISVGYVDDTQFVRFDSDAASPRGEPRAPWVEQEGPEYWDRE<br>TQKYKRQAQADRVNLRKLRGYYNQSEDGSHTLQWMYGCDLGP<br>DGRLLRGYDQSAYDGKDYIALNEDLRSWTAADTAAQITQRKWEA<br>AREAEQWRAYLEGTCVEWLRRYLENGKETLQRAEHPKTHVTHH<br>PVSDHEATLRCWALGFYPAEITLTWQRDGEDQTQDTELVETRPA<br>GDGTFQKWAAVVVPSGEEQRYTCHVQHEGLPEPLTLRWEPSSQ<br>PTIPIVGIVAGLAVLAVLAVLGAVMAVVMCRRKSSGGKGGSCSQA<br>ASSNSAQGSDESLIACKA |
| 4 | Uniprot P20036<br>HLA DPA1<br>(MHC II) | MRPEDRMFHIRAVILRALSLAFLLSLRGAGAIKADHVSTYAAFVQT<br>HRPTGEFMFEFDEDEMFYVDLDKKETVWHLEEFGQAFSFEAQG<br>GLANIAILNNNLNTLIQRSNHTQATNDPPEVTVFPKEPVELGQPNT<br>LICHIDKFFPPVLNVTWLCNGELVTEGVAESLFLPRTDYSFHKFHY<br>LTFVPSAEDFYDCRVEHWGLDQPLLKHWEAQEPIQMPETTETVL<br>CALGLVLGLVGIIVGTVLIIKSLRSGHDPRAQGTL |
| 5 | Uniprot P04440<br>HLA DPB1<br>(MHC II) | MMVLQVSAAPRTVALTALLMVLLTSVVQGRATPENYLFQGRQEC<br>YAFNGTQRFLERYIYNREEFARFDSDVGEFRAVTELGRPAAEYW<br>NSQKDILEEKRAVPDRMCRHNYELGGPMTLQRRVQPRVNVSPS<br>KKGPLQHHNLLVCHVTDFYPGSIQVRWFLNGQEETAGVVSTNLI<br>RNGDWTFQILVMLEMTPQQGDVYTCQVEHTSLDSPVTVEWKAQ<br>SDSARSKTLTGAGGFVLGLIICGVGIFMHRRSKKVQRGSA |
| 6 | Uniprot P01909<br>HLA DQA1<br>(MHC II) | MILNKALMLGALALTTVMSPCGGEDIVADHVASYGVNLYQSYGPS<br>GQYTHEFDGDEQFYVDLGRKETVWCLPVLRQFRFDPQFALTNIA<br>VLKHNLNSLIKRSNSTAATNEVPEVTVFSKSPVTLGQPNILICLVDN<br>IFPPVVNITWLSNGHSVTEGVSETSFLSKSDHSFFKISYLTLLPSA<br>EESYDCKVEHWGLDKPLLKHWEPEIPAPMSELTETVVCALGLSV<br>GLVGIVVGTVFIIRGLRSVGASRHQGPL |
| 7 | Uniprot P01920<br>HLA DQB1<br>(MHC II) | MSWKKALRIPGGLRAATVTLMLAMLSTPVAEGRDSPEDFVYQFK<br>AMCYFTNGTERVRYVTRYIYNREEYARFDSDVEVYRAVTPLGPP<br>DAEYWNSQKEVLERTRAELDTVCRHNYQLELRTTLQRRVEPTVT<br>ISPSRTEALNHHNLLVCSVTDFYPAQIKVRWFRNDQEETTGVVST<br>PLIRNGDWTFQILVMLEMTPQHGDVYTCHVEHPSLQNPITVEWR<br>AQSESAQSKMLSGIGGFVLGLIFLGLGLIIHHRSQKGLLH |
| 8 | Uniprot P01903<br>HLA DRA gene<br>(MHC II) | MAISGVPVLGFFIIAVLMSAQESWAIKEEHVIIQAEFYLNPDQSGEF<br>MFDFDGDEIFHVDMAKKETVWRLEEFGRFASFEAQGALANIAVD<br>KANLEIMTKRSNYTPITNVPPEVTVLTNSPVELREPNVLICFIDKFT<br>PPVVNVTWLRNGKPVTTGVSETVFLPREDHLFRKFHYLPFLPST<br>EDVYDCRVEHWGLDEPLLKHWEFDAPSPLPETTENVVCALGLTV<br>GLVGIIIGTIFIIKGVRKSNAAERRGPL |
| 9 | Uniprot Q30167<br>HLA DRB1 gene<br>(MHC II) | MVCLRLPGGSCMAVLTVTLMVLSSPLALAGDTRPRFLEEVKFEC<br>HFFNGTERVRLLERRVHNQEEYARYDSDVGEYRAVTELGRPDA<br>EYWNSQKDLLERRRAAVDTYCRHNYGVGESFTVQRRVQPKVTV<br>YPSKTQPLQHHNLLVCSVNGFYPGSIEVRWFRNGQEEKTGVVST<br>GLIQNGDWTFQTLVMLETVPQSGEVYTCQVEHPSVMSPLTVEW<br>RARSESAQSKMLSGVGGFVLGLLFLGAGLFIYFRNQKGHSGLPP<br>TGFLS |

TABLE 1.2

| Examples of Mouse MHC Protein Sequences | | |
|---|---|---|
| SEQ ID NO. | Description | Amino Acid Sequence |
| 10 | Uniprot Q91TQ72 MHC II antigen IE alpha (H2-Aa) | RSRALILGVLALTTMLSLCGGEDYIEADHVAFYGISVYQSPGDI GQYTFEFDGDELFYVDLDKKETVWMLPEFGQLTSFDPQGGL QEIATGKYNLEILIKDSNFTPAANEAPQATVFPKSPVLLGQPNT LICFVDNIFPPVINITWLRNSKSVTDGVYETSFLVNRDHSFHKL SYLTFIPSDDDIYDCKVEHWGLEEPVLKHWEPEIPAPMSELTE TVICALGLSVGLVGIVVGTIFIIQGLRSGGTSRH |
| 11 | Uniprot O19440 MHC I antigen (H2-B1) | MAQRTLFLLLAAALTMIETRAGPHSMRYFETAVFRPGLGEPRF ISVGYVVDNTQFVSFDSDAENPRSEPRAPWMEQEGPEYWER ETQIAKDNEQSFGWSLRNLIHYYNQSKGGFHTFQRLSGCDM GLDGRLLRGYLQFAYDGRDYITLNEDLKTWMAADLVALITRRK WEQAGAAELYKFYLEGECVEWLRRYLELGNETLLRTDPPKAH VTHHPRPAGDVTLRCWALGFYPADITLTWQLNGEELTQDMEL VETRPAGDGTFQKWAAVVVPLGKEQNYTCHVYHEGLPEPLTL RWEPPPSTGSNMVNIAVLVVLGAVIIIEAMVAFVLKSSRKIAILP GPAGTKGSSAS |
| 12 | Uniprot Q31191 MHC I H2-K gene (Haplotype d) (H2-K1) | MAPCTLLLLLAAALAPTQTRAARAAARGPVRRSGSHRAPPPG PHSLSDADNPRFEPRAPWMEQEGPEYWEEQTQRAKSDEQ WFRVSLRTAQRYYNQSKGGSHTFQRMFGCDVGSDWRLLRG YQQFAYDGRDYIALNEDLKTWTAADTAALITRRKWEQAGDAE YYRAYLEGECVEWLRRYLELGNETLLRTDSPKAHVTYHPRSQ VDVTLRCWALGFYPADITLTWQLNGEDLTQDMELVETRPAGD GTFQKWAAVVVPLGKEQNYTCHVHHKGLPEPLTLRWKLPPP TVSNTVIIAVLVVLGAAIVTGAVVAFVMKMRRNTGGKGVNYALA PGSQTSDLSLPDGKVMVH |
| 13 | Uniprot P04230 H2 Class II histocompatibility antigen E-B beta chain | MVWLPRVPCVAAVILLLTVLSPPMALVRDSRPWFLEYCKSEC HFYNGTQRVRLLERYFYNLEENLRFDSDVGEFHAVTELGRPD AENWNSQPEFLEQKRAEVDTVCRHNYEISDKFLVRRRVEPTV TVYPTKTQPLEHHNLLVCSVSDFYPGNIEVRWFRNGKEEKTGI VSTGLVRNGDWTFQTLVMLETVPQSGEVYTCQVEHPSLTDP VTVEWKAQSTSAQNKMLSGVGGFVLGLLFLGAGLFIYFRNQK GQSGLQPTGLLS |
| 14 | Uniprot P04224 MHC II E-K alpha chain (underlined portion is portion used in SEQ ID NO: 30) | MATIGALVLRFFFIAVLMSSQKSWAIKEEHTIIQAEFYLLPDKRG EFMFDFDGDEIFHVDIEKSETIWRLEEFAKFASFEAQGALANIA VDKANLDVMKERSNNTPDANVAPEVTVLSRSPVNLGEPNILIC FIDKFSPPVVNVTWLRNGRPVTEGVSETVFLPRDDHLFRKFH YLTFLPSTDDFYDCEVDHWGLEEPLRKHWEFEEKTLLPETKE NVVCALGLFVGLVGIVVGIILIMKGIKKRNVVERRQGAL |
| 15 | GenBank ID: M36939.1 MHC II E-K beta chain (underlined portion is used in SEQ ID NO: 31, 32) | MWLPRVPCVAAVILLLTVLSPPVALVRDSRPWFLEYCKSECHF YNGTQRVRLLVRYFYNLEENLRFDSDVGEFRAVTELGRPDAE NWNSQPEFLEQKRAEVDTVCRHNYEIFDNFLVPRRVEPTVTV YPTKTQPLEHHNLLVCSVSDFYPGNIEVRWFRNGKEEKTGIV STGLVRNGDWTFQTLVMLETVPQSGEVYTCQVEHPSLTDPVT VEWKAQSTSAQNKMLSGVGGFVLGLLFLGAGLFIYFRNQKG QSGLQPTGLLS |

Referring to Table 1.1, the HLA-A (MHC I) sequence (SEQ ID NO: 1) includes the signal peptide (amino acids 1-24); amino acids 25-308 are believed to make up the extracellular region, amino acids 309-332 are believed to make up the transmembrane region, and amino acids 333-365 are believed to make up the cytoplasmic region. The HLA-B (MHC I) sequence (SEQ ID NO: 2) includes the signal peptide (amino acids 1-24); amino acids 25-308 are believed to make up the extracellular region, amino acids 309-332 are believed to make up the transmembrane region, and amino acids 333-362 are believed to make up the cytoplasmic region. The HLA-C(MHC I) sequence (SEQ ID NO: 3) includes the signal peptide (amino acids 1-24); amino acids 25-308 are believed to make up the extracellular region, amino acids 309-333 are believed to make up the transmembrane region, and amino acids 334-366 are believed to make up the cytoplasmic region. The HLA DPA1 (MHC II) sequence (SEQ ID NO: 4) includes the signal peptide (amino acids 1-28); amino acids 29-222 are believed to make up the extracellular region, amino acids 223-245 are believed to make up the transmembrane region, and amino acids 246-260 are believed to make up the cytoplasmic region. The HLA DPB1 (MHC II) sequence (SEQ ID NO: 5) includes the signal peptide (amino acids 1-29); amino acids 30-225 are believed to make up the extracellular region, amino acids 226-246 are believed to make up the transmembrane region, and amino acids 247-258 are believed to make up the cytoplasmic region. The HLA DQA1 (MHC II) sequence (SEQ ID NO: 6) includes the signal peptide (amino acids 1-23); amino acids 24-216 are believed to make up the extracellular region, amino acids 217-239 are believed to make up the transmembrane region, and amino acids 240-254 are believed to make up the cytoplasmic region. The HLA DQB1 (MHC II) sequence (SEQ ID NO: 7) includes the signal peptide (amino acids 1-32); amino acids 33-230 are believed to make up the extracellular region, amino acids 231-251 are believed to make up the transmembrane region, and amino acids 252-261 are believed to make up the cytoplasmic region. The HLA DRA (MHC II) sequence (SEQ ID NO: 8) includes the signal peptide (amino acids 1-25); amino acids 26-216 are believed to make up the extracellular region, amino acids 217-239 are believed to make up the transmembrane region, and amino acids 240-254 are believed to make up the cytoplasmic region. The HLA DRB1 (MHC II) sequence (SEQ ID NO: 9) includes the signal peptide (amino acids 1-29); amino acids 30-227 are believed to make up the extracellular region, amino acids 228-250 are believed to make up the transmembrane region, and amino acids 251-266 are believed to make up the cytoplasmic region. The MHC E-K alpha chain (SEQ ID NO: 14) includes the signal peptide (aa 1-25), the extracellular domain (aa 26-216), the transmembrane domain (aa 217-24), and a cytoplasmic portion (aa 243-255).

As previously discussed, the CRM of the present invention comprises an MHC portion and a TCR portion. In some embodiments, the MHC portion comprises one or more MHC proteins (e.g., HLA-A, HLA-B, HLA-C, HLA-DPA1, HLA-DPB1, HLA-DQA1, HLA-DQB1, HLA-DRA, HLA-DRB1, MHC E-K alpha, MHC E-K beta, etc.), fragments thereof, or combinations thereof. For example, in some embodiments, the MHC portion comprises a fragment of any of SEQ ID NO: 1-15.

In some embodiments, the MHC portion comprises a peptide that is at least 80% identical to an MHC protein or a fragment thereof. In some embodiments, the MHC portion comprises a peptide that is at least 85% identical to an MHC protein or a fragment thereof. In some embodiments, the MHC portion comprises a peptide that is at least 90% identical to an MHC protein or a fragment thereof. In some embodiments, the MHC portion comprises a peptide that is at least 95% identical to an MHC protein or a fragment thereof. In some embodiments, the MHC portion comprises a peptide that is at least 99% identical to an MHC protein or a fragment thereof.

In some embodiments, a fragment of an MHC protein is from 10 to 25 aa in length. In some embodiments, a fragment of an MHC protein is from 10 to 50 aa in length. In some embodiments, a fragment of an MHC protein is from 10 to 100 aa in length. In some embodiments, a fragment of an MHC protein is from 10 to 150 aa in length. In some embodiments, a fragment of an MHC protein is from 10 to 200 aa in length. In some embodiments, a fragment of an MHC protein is from 10 to 250 aa in length. In some embodiments, a fragment of an MHC protein is from 10 to 300 aa in length. In some embodiments, a fragment of an MHC protein is from 10 to 350 aa in length. In some embodiments, a fragment of an MHC protein is from 25 to 50 aa in length. In some embodiments, a fragment of an MHC protein is from 25 to 100 aa in length. In some embodiments, a fragment of an MHC protein is from 25 to 150 aa in length. In some embodiments, a fragment of an MHC protein is from 25 to 200 aa in length. In some embodiments, a fragment of an MHC protein is from 25 to 250 aa in length. In some embodiments, a fragment of an MHC protein is from 25 to 300 aa in length. In some embodiments, a fragment of an MHC protein is from 25 to 350 aa in length. In some embodiments, a fragment of an MHC protein is from 50 to 100 aa in length. In some embodiments, a fragment of an MHC protein is from 50 to 150 aa in length. In some embodiments, a fragment of an MHC protein is from 50 to 200 aa in length. In some embodiments, a fragment of an MHC protein is from 50 to 250 aa in length. In some embodiments, a fragment of an MHC protein is from 50 to 300 aa in length. In some embodiments, a fragment of an MHC protein is from 50 to 350 aa in length. In some embodiments, a fragment of an MHC protein is from 100 to 150 aa in length. In some embodiments, a fragment of an MHC protein is from 100 to 200 aa in length. In some embodiments, a fragment of an MHC protein is from 100 to 250 aa in length. In some embodiments, a fragment of an MHC protein is from 100 to 300 aa in length. In some embodiments, a fragment of an MHC protein is from 100 to 350 aa in length. In some embodiments, a fragment of an MHC protein is from 150 to 200 aa in length. In some embodiments, a fragment of an MHC protein is from 150 to 250 aa in length. In some embodiments, a fragment of an MHC protein is from 150 to 300 aa in length. In some embodiments, a fragment of an MHC protein is from 150 to 350 aa in length. In some embodiments, a fragment of an MHC protein is from 200 to 250 aa in length. In some embodiments, a fragment of an MHC protein is from 200 to 300 aa in length. In some embodiments, a fragment of an MHC protein is from 200 to 350 aa in length. In some embodiments, a fragment of an MHC protein is from 250 to 300 aa in length. In some embodiments, a fragment of an MHC protein is from 250 to 350 aa in length. In some embodiments, a fragment of an MHC protein is more than 350 aa in length.

b. TCR Portion of CRMs

A TCR portion may comprise one or more TCR proteins (e.g., TCRA, TCRB), one or more fragments thereof, or combinations thereof. For reference, non-limiting TCR sequences (human and mouse) are listed below in Table 2.1 and Table 2.2. The present invention is not limited to the TCR sequences in Table 2.1 and Table 2.2.

TABLE 2.1

| Examples of Human TCR Protein Sequences | | |
|---|---|---|
| SEQ ID NO. | Description | Amino Acid Sequence |
| 16 | Uniprot P01848 T cell receptor alpha chain constant region (TRAC, TCRA) | PNIQNPDPAVYQLRDSKSSDKSVCLFTDFDSQTNVSQSKDSDV YITDKTVLDMRSMDFKSNSAVAWSNKSDFACANAFNNSIIPEDT FFPSPESSCDVKLVEKSFETDTNLNFQNLSVIGFRILLLKVAGFN LLMTLRLWSS |
| 17 | Uniprot P01850 T cell receptor beta-1 chain constant region (TRBC1) | EDLNKVFPPEVAVFEPSEAEISHTQKATLVCLATGFFPDHVELS WWVNGKEVHSGVSTDPQPLKEQPALNDSRYCLSSRLRVSATF WQNPRNHFRCQVQFYGLSENDEWTQDRAKPVTQIVSAEAWG RADCGFTSVSYQQGVLSATILYEILLGKATLYAVLVSALVLMAMV KRKDF |

TABLE 2.1-continued

| | Examples of Human TCR Protein Sequences | |
|---|---|---|
| SEQ ID NO. | Description | Amino Acid Sequence |
| 18 | Uniprot A0A5B9 T cell receptor beta-2 chain constant region (TRBC2, TCRBC2) | DLKNVFPPEVAVFEPSEAEISHTQKATLVCLATGFYPDHVELSW WVNGKEVHSGVSTDPQPLKEQPALNDSRYCLSSRLRVSATFW QNPRNHFRCQVQFYGLSENDEWTQDRAKPVTQIVSAEAWGR ADCGFTSESYQQGVLSATILYEILLGKATLYAVLVSALVLMAMVK RKDSRG |
| 19 | Uniprot B7Z8K6 T cell receptor delta chain constant region (TRDC) | SQPHTKPSVFVMKNGTNVACLVKEFYPKDIRINLVSSKKITEFDP AIVISPSGKYNAVKLGKYEDSNSVTCSVQHDNKTVHSTDFEVKT DSTDHVKPKETENTKQPSKSCHKPKAIVHTEKVNMMSLTVLGL RMLFAKTVAVNFLLTAKLFFL |
| 20 | Uniprot P0CF51 T cell receptor gamma-1 chain constant region (TRGC1) | DKQLDADVSPKPTIFLPSIAETKLQKAGTYLCLLEKFFPDVIKIH WQEKKSNTILGSQEGNTMKTNDTYMKFSWLTVPEKSLDKEHR CIVRHENNKNGVDQEIIFPPIKTDVITMDPKDNCSKDANDTLLLQ LTNTSAYYMYLLLLLKSVVYFAIITCCLLRRTAFCCNGEKS |
| 21 | Uniprot P03986 T cell receptor gamma-2 chain constant region (TRGC2, TCRGC2) | DKQLDADVSPKPTIFLPSIAETKLQKAGTYLCLLEKFFPDIIKIHW QEKKSNTILGSQEGNTMKTNDTYMKFSWLTVPEESLDKEHRCI VRHENNKNGIDQEIIFPPIKTDVTTVDPKDSYSKDANDVITMDPK DNWSANDTLLLQLTNTSAYYMYLLLLLKSVVYFAIITCCLLGRTA FCCNGEKS |

TABLE 2.2

| | Examples of Mouse TCR Protein Sequences | |
|---|---|---|
| SEQ ID NO. | Description | Amino Acid Sequence |
| 22 | Uniprot P01849 T cell receptor alpha chain constant region (TCRA-mouse) (underlined portion refers to sequence also used in SEQ ID NO: 30) | PYIQNPEPAVYQLKDPRSQDSTLCLFTDFDSQINVPK TMESGTFITDKTVLDMKAMDSKSNGAIAWSNQTSFT CQDIFKETNATYPSSDVPCDATLTEKSFETDMNLNFQ NLSVMGLRILLLLKVAGFNLLMTLRLWSS |
| 23 | Uniprot P01852 T cell receptor beta-1 chain constant region (TCB1-mouse) | EDLRNVTPPKVSLFEPSKAEIANKQKATLVCLARGFF PDH VELSWWVNGKEVHSGVSTDPQAYKESNYSYCLSSR LRVSATFWHNPRNHFRCQVQFHGLSEEDKWPEGSP KPVTQNISAEAWGRADCGITSASYQQGVLSATILYEIL LGKATLYAVLVSTLVVMAMVKRKNS |
| 24 | Uniprot P01851 T cell receptor beta-2 chain constant region (TCB2-mouse) (underlined portion refers to sequence used in SEQ ID NO: 31, 32) | EDLRNVTPPKVSLFEPSKAEIANKQKATLVCLARGFF PDH VELSWWVNGKEVHSGVSTDPQAYKESNYSYCLSSR LRVSATFWHNPRNHFRCQVQFHGLSEEDKWPEGSP KPVTQNISAEAWGRADCGITSASYHQGVLSATILYEIL LGKATLYAVLVSGLVLMAMVKKKNS |
| 25 | Uniprot P01853 T cell receptor gamma chain constant region C10.5 (TCC1-mouse) | DKRLDADISPKPTIFLPSVAETNLHKTGTYLCLLEKFF PDVIRVYWKEKNGNTILDSQEGDTLKTKGTYMKFSW LTVPERAMGKEHSCIVKHENNKGGADQEIFFPSIKKV ATTCWQDKNDVLQFQFTSTSAYYTYLLLLLKSVIYLAII SFSLLRRTSVCGNEKKS |
| 26 | Uniprot P03985 T cell receptor gamma chain constant region C7.5 (TCC2-mouse) | DKKLDADISPKPTIFLPSVAETNLHKTGTYLCVLEKFF PDVIRVYWKEKKGNTILDSQEGDMLKTNDTYMKFSW LTVPERSMGKEHRCIVKHENNKGGADQEIFFPTIKKV AVSTKPTTCWQDKNDVLQLQFTITSAYYTYLLLLLKS VIYLAIISFSLLRRTSVCCNEKKS |

TABLE 2.2-continued

Examples of Mouse TCR Protein Sequences

| SEQ ID NO. | Description | Amino Acid Sequence |
|---|---|---|
| 27 | Uniprot P06334<br>T cell receptor gamma chain<br>constant region DFL12<br>(TCC3-mouse) | PSDKRLDADISPKPTIFLPSVAETNLHKTGTYLCILEKF<br>FPDVIRVYWKDKNGNTILDSQEGDTLKTKGTYMKFS<br>WLTVPERSMGKEHRCIVKHENNKGGADQEIFFPSIK<br>KVATTCWQDKNDVLQLQFMSTSAYYTYLLLLLKSVIY<br>LAIISFSLLRRTSVCCNEKRS |
| 28 | Uniprot P06335<br>T cell receptor gamma chain<br>constant region 5/10-13<br>(TCC4-mouse) | DKRTDSDFSPKPTIFLPSAAETNLHKAGTYLCLLEKF<br>FPKVIRVYWKEKDGEKILESQEGNTIKTNDRYMKFS<br>WLTVTEDSMAKEHSCIVKHENNKRGVDQEILFPPIGK<br>AFTTINVNPRDSVLRHENVNNATDLEDCMKGRKDML<br>QLQVTTTYAFYTYLILFFKSMVHLAFVVFCLFRRAAM<br>SCDDQRS |

Referring to the TRAC protein (SEQ ID NO: 16) in Table 2.1, amino acids 118-137 are believed to make up the transmembrane domain, and amino acids 138-142 are believed to make up the cytoplasmic domain. Referring to the TRBC1 protein (SEQ ID NO: 17), amino acids 151-171 are believed to make up the transmembrane domain. Referring to the TRBC2 protein (SEQ ID NO: 18), amino acids 145-167 are believed to make up the transmembrane domain. Referring to the TRDC protein (SEQ ID NO: 19), amino acids 130-152 are believed to make up the transmembrane domain. Referring to the TRGC1 protein (SEQ ID NO: 20), amino acids 139-161 are believed to make up the transmembrane domain. Referring to the TRGC2 protein (SEQ ID NO: 21), amino acids 157-177 are believed to make up the transmembrane domain, and amino acids 178-189 are believed to make up the cytoplasmic domain.

As previously discussed, the CRM of the present invention comprises an MHC portion and a TCR portion. In some embodiments, a TCR portion comprises one or more TCR proteins (e.g., TRAC, TRBC1, TRBC2, TRDC, TRCG1, TRCG2, TCRA-mouse, TCB1-mouse, TCB2-mouse, TCC1-mouse, TCC2-mouse, TCC3 mouse, TCC4 mouse, etc.), fragments thereof, or combinations thereof. For example, the TCR portion may comprise a fragment of any of SEQ ID NO: 16-28. In some embodiments, the fragment is from 5 to 10 aa in length. In some embodiments, the fragment is from 10 to 20 aa in length, in some embodiments, the fragment is from 10 to 30 aa in length. In some embodiments, the fragment is from 10 to 40 aa in length. In some embodiments, the fragment is from 10 to 50 aa in length, etc.

In some embodiments, the TCR portion comprises a peptide that is at least 80% identical to a TCR protein (e.g., any of SEQ ID NO: 16-28), or a fragment thereof. In some embodiments, the TCR portion comprises a peptide that is at least 85% identical to a TCR protein (e.g., any of SEQ ID NO: 16-28), or a fragment thereof. In some embodiments, the TCR portion comprises a peptide that is at least 90% identical to a TCR protein (e.g., any of SEQ ID NO: 16-28), or a fragment thereof. In some embodiments, the TCR portion comprises a peptide that is at least 95% identical to a TCR protein (e.g., any of SEQ ID NO: 16-28), or a fragment thereof. In some embodiments, the TCR portion comprises a peptide that is at least 99% identical to a TCR protein (e.g., any of SEQ ID NO: 16-28), or a fragment thereof.

In some embodiments, a fragment of a TCR protein is from 10 to 25 aa in length. In some embodiments, a fragment of a TCR protein is from 10 to 50 aa in length. In some embodiments, a fragment of a TCR protein is from 10 to 100 aa in length. In some embodiments, a fragment of a TCR protein is from 10 to 150 aa in length. In some embodiments, a fragment of a TCR protein is from 25 to 50 aa in length. In some embodiments, a fragment of a TCR protein is from 25 to 100 aa in length. In some embodiments, a fragment of a TCR protein is from 25 to 150 aa in length. In some embodiments, a fragment of a TCR protein is from 50 to 100 aa in length. In some embodiments, a fragment of a TCR protein is from 50 to 150 aa in length. In some embodiments, a fragment of a TCR protein is from 100 to 150 aa in length. In some embodiments, a fragment of a TCR protein is more than 150 aa in length.

In some embodiments, the CRM comprises a peptide antigen. Any appropriate peptide antigen may be used. The peptide antigen in CRM$^{pMHC}$ complex directs the specificity of the CRM$^{pMHC}$ molecule, therefore the CRM$^{pMHC}$ molecule will be specific for T cells with TCRs that are specific for that peptide antigen CRM$^{pMHC}$. A non-limiting example of a peptide antigen that may be used with the CRM is moth cytochrome c peptide (aa 88-103, ANERADLIAYLKQATK (SEQ ID NO: 29)). Any appropriate peptide antigen may be used, and the present invention is not limited to the peptide antigens disclosed herein. For example, in some embodiments, the peptide antigen comprises any immunodominant peptide antigen identified to bind a class I or class II MHC. In some embodiments, the peptide antigen comprises any immunodominant peptide antigen identified to bind a class I or class II MHC and elicit a response. A response may include but is not limited to an autoimmune response, an allergic response, an asthma response, or an inappropriate Treg response. The peptide antigen may be any appropriate length.

In some embodiments, the CRM comprises at least a portion of an MHC molecule that allows for binding to an appropriate TCR. In some embodiments, the CRM comprises at least a portion of an MHC molecule that allows for binding to an appropriate TCR and at least a portion of a TCR molecule (e.g., a portion of a TCR molecule that allows for appropriate signaling and/or complexing subunits such as CD3 subunits). In some embodiments, the CRM comprises a transmembrane domain that is at least partially derived from (i) an MHC molecule, (ii) a TCR molecule, or (iii) both the MHC molecule and TCR molecule. In some embodiments, the CRM comprises a transmembrane domain, wherein a portion (or all) of the transmembrane domain is not derived from an MHC molecule or a TCR molecule. In some embodiments, the CRM comprises an extracellular domain that is at least partially derived from (i) an MHC molecule, (ii) a TCR molecule, or (iii) both the MHC molecule and TCR molecule. In some embodiments, the CRM comprises an extracellular domain, wherein a portion of the extracellular domain is not derived from an MHC molecule or a TCR molecule.

In one embodiment, the CRM comprises at least a portion of the extracellular domain of an MHC molecule (e.g., the extracellular domain of HLA-DRA) and at least a portion of the transmembrane domain of a TCR molecule and at least a portion of the cytoplasmic domain of a TCR molecule. In another embodiment, the CRM comprises at least a portion of the extracellular domain of a TCR molecule.

Surrogate Coreceptors-(SCoR)

In some embodiments, the present invention features surrogate coreceptors (SCoRs), e.g., receptors that recruit signaling molecules (e.g., kinases such as but not limited to Src kinases (e.g., Lck), phosphatases, etc.). The SCoRs may recruit signaling molecules (e.g., kinases) to the CRM and/or CD3 subunits. Without wishing to limit the present invention to any theory or mechanism, it is believed that certain SCoRs may enhance signaling through the $CRM^{pMHC}$-CD3 complex. The present invention is not limited to the aforementioned uses of SCoRs. For example, the SCoRs of the present invention may be used in 5M-CARs that have an Fv-based CRM module ($CRM^{Fv}$) instead of a $CRM^{pMHC}$. The SCoRs of the present invention may be used in any appropriate application. For example, the SCoRs of the present invention may be used in combination with conventional single chain CARs (aka 1 module or 1M-CARs). Without wishing to be bound to a particular theory or mechanism, the SCoRs may enhance the function of the 1M-CARs.

For example, the present invention provides SCoRs comprising a portion of CD8. Referring to FIG. 2 (left side), CD8 forms a dimer, consisting of a CD8α and CD8β chain. The two chains of CD8 each have an immunoglobulin variable-like extracellular domain (ECD), a transmembrane domain (TMD), and an intracellular domain (ICD). Wild type CD8 binds to class I MHCs.

In some embodiments, a single chain of CD8 (e.g., a CD8α chain or a CD8β chain) comprises an extracellular domain (ECD), a transmembrane domain (TMD), and an intracellular domain (ICD). In some embodiments, the extracellular domain (ECD) may comprise a immunoglobulin variable (Ig)-like domain and a mucin-like stalk domain.

The SCoRs of the present invention may comprise: (1) an alpha chain with a binding portion (e.g., antibody fragment, e.g., Fv Ig domain, etc.) linked to a CD8α portion (e.g., the portion of CD8α except for the Ig domain); and (2) a beta chain with a binding portion (e.g., antibody fragment, e.g., Fv Ig domain, etc.) linked to a CD8β portion (e.g., the portion of CD8β except for the Ig domain).

In some embodiments, the binding domains of the SCoR are antibody Fv domains, e.g., the Ig domains of both CD8α and CD8β are each replaced with an antibody Fv domain, e.g., an antibody Fv domain specific for a target TCR. Referring to FIG. 2 (right side), a SCoR was constructed to target an epitope on TCRβ (the FG-loop) that is ubiquitous to all mouse TCRs. The SCoR comprises an Fv region of the anti-mTCRβ mAb H57-597 (H57) fused to the stalks of CD8α and CD8β (referred to as $SCoR^{TCR}$ in FIG. 2). More specifically, the CD8α Ig domain was replaced with the H57 heavy chain (HC) Fv Ig domain, and the CD8β Ig domain was replaced with the light chain (LC) Fv Ig domain.

The present invention also features SCoRs synthesized by tuning the binding kinetics of the particular Fv. Co-receptors do not typically bind their target with high affinity so that they can cycle through various ligands. In some cases, cells expressing the native Fv affinity may bind any T cell, regardless of TCR specificity, and not disengage. Thus, mutations may be introduced to the Fv(s) that affect the binding of the Fv to the TCR of interest. For example, the SCoR described above may be modified by introducing alanine mutations for the large hydrophobic H57 residues that are believed to mediate binding to the TCR (e.g., light chain (LC): L28, F32, Y34; HC: W33, Y35, F98). In some embodiments, mutations in the light chain may include but are not limited to F32A, L28A, Y34, or a combination thereof (FIG. 6). In other embodiments, mutations in the heavy chain may include but are not limited to W298A, W33A, Y35A, F98A, or a combination thereof (FIG. 6). In further embodiments, mutations in the light chain may include but are not limited to mutation at residues L28, F32, Y34, or a combination thereof. In some embodiments, mutations in the heavy chain may include but are not limited to mutation at residues W298, W33, Y35, F98, or a combination thereof.

The present invention is not limited to the aforementioned SCoR nor the specific mutations described herein. Further, the present invention is not limited to SCoRs made based on mouse sequences. The sequences of any of the SCoRs described herein may be tailored to a particular animal or subject (e.g., human, primate, dog, rat, etc.).

As previously discussed, the present invention features methods and compositions for "tuning" the binding kinetics (e.g., via mutagenesis, etc.) as desired, e.g., to tune the binding to mimic the natural binding kinetics of CD8 for MHCI. For example, one of ordinary skill in the art may start with a high affinity Fv and alter said Fv to weaken the binding by introducing mutations to the sequence or reverting the sequence to that of the germline sequence (or a sequence similar to the germline sequence). In some embodiments, the methods feature mutating the antigen binding CDR loops of the Fv to tune its affinity for the target ligand, e.g., to tune the affinity more closely to natural binding kinetics (e.g., tune to natural binding kinetics of CD8 for MHCI).

In some embodiments, a SCoR was constructed comprising a CD8α chain wherein the CD8α Ig domain was replaced with the H57-597 heavy chain (HC) and a CD8β chain wherein the CD8β Ig domain was replaced with the light chain (LC), wherein the LC comprises a F32A mutation ($SCoR^{TCR}$ F32A). Referring to FIG. 3, when expressed with the MCC:I-$E^k$ pMHCIIR on 58α⁻β⁻ cells, the pMHCIIR⁺ $SCoR^{TCR}$ F32A⁺ cells made more IL-2 than pMHCIIR⁺ cells when co-incubated with M12 B cells expressing the 2B4 TCR, CD4, and truncated CD3 subunits (CD3T) that lack ITAMs. The TCR-CD3T complexes cannot signal, and M12 cells do not make IL-2, therefore the pMHCIIR-CD3 complexes signal more with this $SCoR^{TCR}$ F32A than without.

In other embodiments, a SCoR was constructed comprising a CD8α chain wherein the CD8α Ig domain was replaced with the H57-597 heavy chain (HO), wherein the HC comprises aa W33A mutation and a CD8β chain, wherein the CD8β Ig domain was replaced with the H57 light chain (LC). In further embodiments, a SCoR was constructed comprising a CD8α chain wherein the CD8α Ig domain was replaced with the H57-597 heavy chain (HC), wherein the HC comprises aa W33A mutation and a CD8β chain wherein the CD8β Ig domain was replaced with the H57 light chain (LC), wherein the LC comprises a F32A mutation Table 3.1 lists the sequence for CD8α and CD8β and non-limiting examples of SCoRs featuring H57 heavy chain and H57 light chain as the binding portions of the SCoRs, as well as examples of SCoRs featuring portions of the 145-2011 antibody (monoclonal antibody specific for mouse CD3 epsilon).

TABLE 3.1

| | | |
|---|---|---|
| | | Examples of SCoRs |
| SEQ ID NO. | Description | Amino Acid Sequence |
| 30 | CD8α (mouse) (UniProt P01731) | MASPLTRFLSLNLLLLGESIILGSGEAKPQAPELRIFPKKMD AELGQKVDLVCEVLGSVSQGCSWLFQNSSSKLPQPTFVV YMASSHNKITWDEKLNSSKLFSAMRDTNNKYVLTLNKFSK ENEGYYFCSVISNSVMYFSSVVPVLQKVNSTTTKPVLRTP SPVHPTGTSQPQRPEDCRPRGSVKGTGLDFACDIYIWAP LAGICVALLLSLIITLICYHRSRKRVCKCPRPLVRQEGKPRP SEKIV |
| 31 | CD8β (mouse) (UniProt P10300) | MQPWLWLVFSMKLAALWSSSALIQTPSSLLVQTNHTAKM SCEVKSISKLTSIYWLRERQDPKDKYFEFLASWSSSKGVL YGESVDKKRNIILESSDSRRPFLSIMNVKPEDSDFYFCATV GSPKMVFGTGTKLTVVDVLPTTAPTKKTTLKMKKKKQCPF PHPETQKGLTCSLTTLSLLVVCILLLLAFLGVAVYFYCVRRR ARIHFMKQFHK |
| 32 | SCoR$^{TCR}$ (alpha) (SCoR with the CD8α Ig domain replaced with the H57 heavy chain) | MQRNLGAVLGILWVQICWVRGTSEVYLVESGGDLVQPGS SLKVSCAASGFTFSDFWMYWVRQAPGKGLEWVGRIKNIP NNYATEYADSVRGRFTISRDDSRNSIYLQMNRLRVDDTAIY YCTRAGRFDHFDYWGQGTMVTVSGTKVNSTTTKPVLRT PSPVHPTGTSQPQRPEDCRPRGSVKGTGLDFACDIYIWA PLAGICVAPLLSLIITLICYHRSRKRVCKCPRPLVRQEGKPR PSEKIV |
| 33 | SCoR$^{TCR}$ (beta) (SCoR with the CD8β Ig domain replaced with the H57 light chain) | MATRLLCYTVLCLLGARILNSKYPYDVPDYAGGSYELIQPS SASVTVGETVKITCSGDQLPKNFAYWFQQKSDKNILLLIYM DNKRPSGIPERFSGSTSGTTATLTISGAQPEDEAAYYCLSS YGDNNDLVFGSGTQLTVLSGDVLPTTAPTKKTTLKMKKKK QCPFPHPETQKGLTCSLTTLSLLVVCILLLLAFLGVAVYFYC VRRRARIHFMKQFHK |
| 34 | SCoR$^{TCR}$ F32A (beta) (light chain comprises an F32A mutation) | MATRLLCYTVLCLLGARILNSKYPYDVPDYAGGSYELIQPS SASVTVGETVKITCSGDQLPKNAAYWFQQKSDKNILLLIY MDNKRPSGIPERFSGSTSGTTATLTISGAQPEDEAAYYCL SSYGDNNDLVFGSGTQLTVLSGDVLPTTAPTKKTTLKMKK KKQCPFPHPETQKGLTCSLTTLSLLVVCILLLLAFLGVAVYF YCVRRRARIHFMKQFHK |
| 35 | SCoR$^{TCR}$ L28A (beta) (light chain comprises an L28A mutation) | MATRLLCYTVLCLLGARILNSKYPYDVPDYAGGSYELIQPS SASVTVGETVKITCSGDQAPKNFAYWFQQKSDKNILLLIY MDNKRPSGIPERFSGSTSGTTATLTISGAQPEDEAAYYCL SSYGDNNDLVFGSGTQLTVLSGDVLPTTAPTKKTTLKMKK KKQCPFPHPETQKGLTCSLTTLSLLVVCILLLLAFLGVAVYF YCVRRRARIHFMKQFHK |
| 36 | SCoR$^{TCR}$ Y34A (beta) (light chain comprises a Y34A mutation) | MATRLLCYTVLCLLGARILNSKYPYDVPDYAGGSYELIQPS SASVTVGETVKITCSGDQLPKNFAAWFQQKSDKNILLLIY MDNKRPSGIPERFSGSTSGTTATLTISGAQPEDEAAYYCL SSYGDNNDLVFGSGTQLTVLSGDVLPTTAPTKKTTLKMKK KKQCPFPHPETQKGLTCSLTTLSLLVVCILLLLAFLGVAVYF YCVRRRARIHFMKQFHK |
| 37 | SCoR$^{TCR}$ W33A (alpha) (heavy chain comprises a W33A mutation) | MATRLLCYTVLCLLGARILNSKYPYDVPDYAGGSYELIQPS SASVTVGETVKITCSGDQLPKNFAYAFQQKSDKNILLLIYM DNKRPSGIPERFSGSTSGTTATLTISGAQPEDEAAYYCLSS YGDNNDLVFGSGTQLTVLSGDVLPTTAPTKKTTLKMKKKK QCPFPHPETQKGLTCSLTTLSLLVVCILLLLAFLGVAVYFYC VRRRARIHFMKQFHK |
| 38 | SCoR$^{TCR}$ F32V (light chain comprises a F32V mutation) | MATRLLCYTVLCLLGARILNSKYPYDVPDYAGGSYELIQPS SASVTVGETVKITCSGDQLPKNVAYWFQQKSDKNILLLIY MDNKRPSGIPERFSGSTSGTTATLTISGAQPEDEAAYYCL SSYGDNNDLVFGSGTQLTVLSGDVLPTTAPTKKTTLKMKK KKQCPFPHPETQKGLTCSLTTLSLLVVCILLLLAFLGVAVYF YCVRRRARIHFMKQFHK |

TABLE 3.1-continued

Examples of SCoRs

| SEQ ID NO. | Description | Amino Acid Sequence |
|---|---|---|
| 39 | SCoR$^{TCR}$ F32L (light chain comprises a F32L mutation) | MATRLLCYTVLCLLGARILNSKYPYDVPDYAGGSYELIQPS SASVTVGETVKITCSGDQLPKNLAYWFQQKSDKNILLLIYM DNKRPSGIPERFSGSTSGTTATLTISGAQPEDEAAYYCLSS YGDNNDLVFGSGTQLTVLSGDVLPTTAPTKKTTLKMKKKK QCPFPHPETQKGLTCSLTTLSLLVVCILLLLAFLGVAVYFYC VRRRARIHFMKQFHK |
| 40 | SCoR + 2C11 (beta) (SCoR with the CD8beta Ig domain replaced with the 2C11 heavy chain) | MATRLLCYTVLCLLGARILNSKYPYDVPDYAGGSEVQLVE SGGGLVQPGKSLKLSCEASGFTFSGYGMHWVRQAPGR GLESVAYITSSSINIKYADAVKGRFTVSRDNAKNLLFLQMNI LKSEDTAMYYCARFDWDKNYWGQGTMVTVSSGDVLPTT APTKKTTLKMKKKQCPFPHPETQKGLTCSLTTLSLLVVCI LLLLAFLGVAVYFYCVRRRARIHFMKQFHK |
| 41 | SCoR + 2C11 (alpha) (SCoR with the CD8alpha Ig domain replaced with the 2C11 light chain) | MQRNLGAVLGILWVQICWVRGTSDIQMTQSPSSLPASLG DRVTINCQASQDISNYLNWYQQKPGKAPKLLIYYTNKLAD GVPSRFSGSGSGRDSSFTISSLESEDIGSYYCQQYYNYP WTFGPGTKLEIKGTKVNSTTTKPVLRTPSPVHPTGTSQPQ RPEDCRPRGSVKGTGLDFACDIYIWAPLAGICVAPLLSLIIT LICYHRSRKRVCKCPRPLVRQEGKPRPSEKIV |
| 42 | SCoR + 2C11 (beta) (SCoR with the CD8β Ig domain replaced with the 2C11 light chain with W135A mutation) | GSEVQLVESGGGLVQPGKSLKLSCEASGFTFSGYGMHW VRQAPGRGLESVAYITSSSINIKYADAVKGRFTVSRDNAKN LLFLQMNILKSEDTAMYYCARFDADKNYWGQGTMVTVSS GDVLPTTAPTKKTTLKMKKKQCPFPHPETQKGLTCSLTT LSLLVVCILLLLAFLGVAVYFYCVRRRARIHFMKQFHK |

TABLE 3.2

Examples of SCoRs (see FIG. 6):

| SEQ ID NO. | Description | Nucleic Acid Sequence |
|---|---|---|
| 51 | a SCoR comprising a CD8α χηαἱν, ωηερεἱν τηε CD8α Ig domain replaced with the H57 heavy chain and a CD8β chain wherein the CD8β Ig domain is replaced with the H57 light chain comprising a F32V mutation | ATGGCTACAAGGCTCCTCTGTTACACAGTACTTTGTCTCCT GGGTGCAAGAATTTTGAACTCAAAATACCCATACGATGTTC CAGATTACGCTGGAGGATCCTATGAGCTGATCCAGCCCAG TTCTGCCTCTGTGACTGTAGGCGAGACCGTTAAGATAACAT GTAGTGGTGACCAACTACCGAAGAATGCTGCATATTGGTTC CAGCAGAAGTCGGACAAAAACATCCTCTTACTTATTTACATG GATAACAAAAGACCTAGCGGAATCCCCGAACGGTTCTCAG GCAGCACTTCAGGGACGACCGCGACCCTGACAATTTCCG GCGCTCAGCCAGAGGACGAAGCCGCTTATTACTGCTTGTC CAGCTACGGAGATAACAATGATCTGGTCTTTGGGTCCGGTA CACAGCTCACCGTGCTGTCCGGAGATGTCCTTCCTACAAC TGCCCCAACCAAGAAGACTACCCTGAAGATGAAGAAGAAG AAGCAATGCCCGTTCCCCCACCCAGAGACCCAGAAGGGC CTGACATGCAGCCTTACCACCCTCAGCCTGCTGGTAGTCT GCATCCTGCTTCTGCTGGCATTCCTCGGAGTGGCCGTCTA CTTTTACTGTGTGCGGAGGAGAGCCCGCATTCACTTCATG AAACAGTTTCACAAAAGATCTGGCGGAGAGGGCAGAGGAA GTCTGCTAACATGCGGTGACGTCGAGGAGAATCCTGGCCC AATGCAGAGGAACCTGGGAGCTGTGCTGGGGATTCTGTG GGTGCAGATTTGCTGGGTGAGAGGAACTAGTGAGGTCTAC CTCGTGGAATCAGGAGGAGACCTCGTGCAGCCAGGCAGC AGCCTAAAAGTTAGTTGTGCTGCATCTGGCTTCACCTTTAG TGACTTCTGGATGTACTGGGTTCGCCAGGCTCCTGGAAAA GGACTGGAGTGGGTGGGTCGCATCAAGAACATCCCCAATA ACTATGCCACAGAATATGCTGACAGTGTTCGAGGACGCTTC ACTATTTCCAGAGATGACAGCCGAAATTCTATTTATCTGCAG ATGAACCGCCTTCGTGTGGATGATACAGCCATTTACTACTG CACCCGAGCTGGACGATTTGACCACTTTGATTATTGGGGC CAGGGCACAATGGTGACTGTTTCTGGTACCAAAGTGAACT CTACTACTACCAAGCCAGTGCTGCGAACTCCCTCACCTGT GCACCCTACCGGGACATCTCAGCCCCAGAGACCAGAAGAT TGTCGGCCCCGTGGCTCAGTGAAGGGGACCGGATTGGAC TTCGCCTGTGATATTTACATCTGGGCACCCTTGGCCGGAAT CTGCGTGGCCCCTCTGCTGTCCTTGATCATCACTCTCATCT |

TABLE 3.2-continued

Examples of SCoRs (see FIG. 6):

| SEQ ID NO. | Description | Nucleic Acid Sequence |
|---|---|---|
| | | GCTACCACAGGAGCCGAAAGCGTGTTTGCAAATGTCCCAG GCCGCTAGTCAGACAGGAAGGCAAGCCCAGACCTTCAGA GAAAATTGTGGCGGCCGCATGATAATTGAATTCATGAC |
| 52 | a SCoR comprising a CD8α χηαіv, ωηερεіν τηε CD8α Ig domain is replaced with the H57 heavy chain comprising a W33A mutation and a CD8β chain wherein the CD8β Ig domain is replaced with the H57 light chain. | ATGGCTACAAGGCTCCTCTGTTACACAGTACTTTGTCTCCT GGGTGCAAGAATTTTGAACTCAAAATACCCATACGATGTTC CAGATTACGCTGGAGGATCCTATGAGCTGATCCAGCCCAG TTCTGCCTCTGTGACTGTAGGCGAGACCGTTAAGATAACAT GTAGTGGTGACCAACTACCGAAGAATTTTGCATATTGGTTC CAGCAGAAGTCGGACAAAAACATCCTCTTACTTATTTACATG GATAACAAAAGACCTAGCGGAATCCCCGAACGGTTCTCAG GCAGCACTTCAGGGACGACCGCGACCCTGACAATTTCCG GCGCTCAGCCAGAGGACGAAGCCGCTTATTACTGCTTGTC CAGCTACGGAGATAACAATGATCTGGTCTTTGGGTCCGGTA CACAGCTCACCGTGCTGTCCGGAGATGTCCTTCCTACAAC TGCCCCAACCAAGAAGACTACCCTGAAGATGAAGAAGAAG AAGCAATGCCCGTTCCCCCACCCAGAGACCCAGAAGGGC CTGACATGCAGCCTTACCACCCTCAGCCTGCTGGTAGTCT GCATCCTGCTTCTGCTGGCATTCCTCGGAGTGGCCGTCTA CTTTTTACTGTGTGCGGAGGAGAGCCCGCATTCACTTCATG AAACAGTTTCACAAAAGATCTGGCGGAGAGGGCAGAGGAA GTCTGCTAACATGCGGTGACGTCGAGGAGAATCCTGGCCC AATGCAGAGGAACCTGGGAGCTGTGCTGGGGATTCTGTG GGTGCAGATTTGCTGGGTGAGAGGAACTAGTGAGGTCTAC CTCGTGGAATCAGGAGGAGACCTCGTGCAGCCAGGCAGC AGCCTAAAAGTTAGTTGTGCTGCATCTGGCTTCACCTTTAG TGACTTCGCAATGTACTGGGTTCGCCAGGCTCCTGGAAAA GGACTGGAGTGGGTGGGTCGCATCAAGAACATCCCCAATA ACTATGCCACAGAATATGCTGACAGTGTTCGAGGACGCTTC ACTATTTCCAGAGATGACAGCCGAAATTCTATTTATCTGCAG ATGAACCGCCTTCGTGTGGATGATACAGCCATTTACTACTG CACCCGAGCTGGACGATTTGACCACTTTGATTATTGGGGC CAGGGCACAATGGTGACTGTTTCTGGTACCAAAGTGAACT CTACTACTACCAAGCCAGTGCTGCGAACTCCCTCACCTGT GCACCCTACCGGGACATCTCAGCCCCAGAGACCAGAAGAT TGTCGGCCCCGTGGCTCAGTGAAGGGGACCGGATTGGAC TTCGCCTGTGATATTTACATCTGGGCACCCTTGGCCGGAAT CTGCGTGGCCCCTCTGCTGTCCTTGATCATCACTCTCATCT GCTACCACAGGAGCCGAAAGCGTGTTTGCAAATGTCCCAG GCCGCTAGTCAGACAGGAAGGCAAGCCCAGACCTTCAGA GAAAATTGTGGCGGCCGCATGATAATTGAATTCATGAC |
| 53 | a SCoR comprising a CD8a χηαіv, ωηερεіν τηε CD8α Ig domain is replaced with the H57 heavy chain comprising a W33A mutation and a CD8β chain wherein the CD8β Ig domain is replaced with the H57 light chain comprising a F32V mutation | ATGGCTACAAGGCTCCTCTGTTACACAGTACTTTGTCTCCT GGGTGCAAGAATTTTGAACTCAAAATACCCATACGATGTTC CAGATTACGCTGGAGGATCCTATGAGCTGATCCAGCCCAG TTCTGCCTCTGTGACTGTAGGCGAGACCGTTAAGATAACAT GTAGTGGTGACCAACTACCGAAGAATTTTGCATATTGGTTC CAGCAGAAGTCGGACAAAAACATCCTCTTACTTATTTACATG GATAACAAAAGACCTAGCGGAATCCCCGAACGGTTCTCAG GCAGCACTTCAGGGACGACCGCGACCCTGACAATTTCCG GCGCTCAGCCAGAGGACGAAGCCGCTTATTACTGCTTGTC CAGCTACGGAGATAACAATGATCTGGTCTTTGGGTCCGGTA CACAGCTCACCGTGCTGTCCGGAGATGTCCTTCCTACAAC TGCCCCAACCAAGAAGACTACCCTGAAGATGAAGAAGAAG AAGCAATGCCCGTTCCCCCACCCAGAGACCCAGAAGGGC CTGACATGCAGCCTTACCACCCTCAGCCTGCTGGTAGTCT GCATCCTGCTTCTGCTGGCATTCCTCGGAGTGGCCGTCTA CTTTTTACTGTGTGCGGAGGAGAGCCCGCATTCACTTCATG AAACAGTTTCACAAAAGATCTGGCGGAGAGGGCAGAGGAA GTCTGCTAACATGCGGTGACGTCGAGGAGAATCCTGGCCC AATGCAGAGGAACCTGGGAGCTGTGCTGGGGATTCTGTG GGTGCAGATTTGCTGGGTGAGAGGAACTAGTGAGGTCTAC CTCGTGGAATCAGGAGGAGACCTCGTGCAGCCAGGCAGC AGCCTAAAAGTTAGTTGTGCTGCATCTGGCTTCACCTTTAG TGACTTCGCAATGTACTGGGTTCGCCAGGCTCCTGGAAAA GGACTGGAGTGGGTGGGTCGCATCAAGAACATCCCCAATA ACTATGCCACAGAATATGCTGACAGTGTTCGAGGACGCTTC ACTATTTCCAGAGATGACAGCCGAAATTCTATTTATCTGCAG ATGAACCGCCTTCGTGTGGATGATACAGCCATTTACTACTG CACCCGAGCTGGACGATTTGACCACTTTGATTATTGGGGC CAGGGCACAATGGTGACTGTTTCTGGTACCAAAGTGAACT CTACTACTACCAAGCCAGTGCTGCGAACTCCCTCACCTGT GCACCCTACCGGGACATCTCAGCCCCAGAGACCAGAAGAT TGTCGGCCCCGTGGCTCAGTGAAGGGGACCGGATTGGAC |

TABLE 3.2-continued

Examples of SCoRs (see FIG. 6):

| SEQ ID NO. | Description | Nucleic Acid Sequence |
|---|---|---|
| | | TTCGCCTGTGATATTTACATCTGGGCACCCTTGGCCGGAAT CTGCGTGGCCCCTCTGCTGTCCTTGATCATCACTCTCATCT GCTACCACAGGAGCCGAAAGCGTGTTTGCAAATGTCCCAG GCCGCTAGTCAGACAGGAAGGCAAGCCCAGACCTTCAGA GAAAATTGTGGCGGCCGCATGATAATTGAATTCATGAC |

The present invention is not limited to any particular antibody: the present invention includes grafting any appropriate Ig domains onto the CD8 stalks to make a SCoR.

It is also possible to reconstruct the germline sequence of the non-affinity matured antibody (e.g., H57 mAb). The germline sequence may be useful for considering a mutagenesis strategy.

Without wishing to limit the present invention to any theory or mechanism, it is believed that a SCoR that binds the target TCR-CD3 complex with faster kinetics than the CRM$^{pMHC}$ (and approximate the spatial relationship between the TCR-CD3 complex and CD8) would be optimal.

The present invention is not limited to SCoRs comprising a portion of CD8. In some embodiments, the SCoR comprises a portion of CD4. For example, in some embodiments, single-chain Fv antibody fragments are fused to the D2-D4 domains of CD4.

The present invention also features SCoRs synthesized based on tuning signaling intensity by tuning linkage to Lck.

III. Lck Fusions

Other approaches to tuning the SCoR signaling include other modifications to CD8 and Lck fusions. For example, the present invention also features a CD8-Lck fusion and a CD4-Lck fusion.

For example, the present invention provides a fusion molecule wherein Lck is fused to CD4 after its second intracellular residue (see below). This fusion protein has been shown to increase signaling and allow detection of TCR scanning of MHCII.

The fusion proteins may be constructed a number of ways, e.g., connecting the CD4 portion to the Lck portion directly, connecting the CD4 portion to the Lck portion indirectly, connecting amino acids 1-420 of CD4 to amino acids 1-509 of Lck (indirectly or directly), connecting amino acids 1-420 of CD4 to amino acids 4-509 of Lck (indirectly or directly), etc. In some embodiments, the Lck molecule attached to CD4 comprises one or more mutations. In some embodiments, the CD4 attached to Lck comprises one or more mutations. In some embodiments, both the CD4 and the Lck comprise one or more mutations.

In some embodiments, the CD4 intracellular domain (ICD) (e.g., at least a portion of, or all) will be used to replace at least a portion of the native CD8 ICD (e.g., CD8a ICD) in a CD8-based SCoR. In some embodiments, at least a portion of the CD4 ICD and at least a portion of the transmembrane domain (TM) are used to replace at least a portion of the native CD8 ICD and CD8 TM domain (respectively) in a CD8-based SCoR.

Table 4 lists the sequence for wild type CD4, wild type Lck, and non-limiting examples of the linking regions of Lck Fusions (e.g., where the CD4 links to Lck).

TABLE 4

Examples of linkage regions of Lck Fusions

| SEQ ID NO. | Description | Amino Acid Sequence |
|---|---|---|
| 43 | CD4 (mouse) (UniProt P06332) | MCRAISLRRLLLLLLQLSQLLAVTQGKTLVLGKEGESAELPC ESSQKKITVFTWKFSDQRKILGQHGKGVLIRGGSPSQFDRF DSKKGAWEKGSPPLIINKLKMEDSQTYICELENRKEEVELW VFKVTFSPGTSLLQGQSLTLTLDSNSKVSNPLTECKHKKGK VVSGSKVLSMSNLRVQDSDFWNCTVTLDQKKNWFGMTLS VLGFQSTAITAYKSEGESAEFSFPLNFAEENGWGELMWKA EKDSFFQPWISFSIKNKEVSVQKSTKDLKLQLKETLPLTLKIP QVSLQFAGSGNLTLTLDKGTLHQEVNLVVMKVAQLNNTLTC EVMGPTSPKMRLTLKQENQEARVSEEQKVVQVVAPETGz WQCLLSEGDKVKMDSRIQVLSRGVNQTVFLACVLGGSFGF LGFLGLCILCCVRCRHQQRQAARMSQIKRLLSEKKTCQCP HRMQKSHNLI |
| 44 | Lck (mouse) (UniProt P06240) | MGCVCSSNPEDDWMENIDVCENCHYPIVPLDSKISLPIRNG SEVRDPLVTYEGSLPPASPLQDNLVIALHSYEPSHDGDLGF EKGEQLRILEQSGEWWKAQSLTTGQEGFIPFNFVAKANSLE PEPWFFKNLSRKDAERQLLAPGNTHGSFLIRESESTAGSFS LSVRDFDQNQGEVVKHYKIRNLDNGGFYISPRITFPGLHDL VRHYTNASDGLCTKLSRPCQTQKPQKPWWEDEWEVPRE TLKLVERLGAGQFGEVWMGYYNGHTKVAVKSLKQGSMSP DAFLAEANLMKQLQHPRLVRLYAVVTQEPIYIITEYMENGSL VDFLKTPSGIKLNVNKLLDMAAQIAEGMAFIEEQNYIHRDLR AANILVSDTLSCKIADFGLARLIEDNEYTAREGAKFPIKWTAP EAINYGTFTIKSDVWSFGILLTEIVTHGRIPYPGMTNPEVIQN LERGYRMVRPDNCPEELYHLMMLCWKERPEDRPTFDYLR SVLDDFFTATEGQYQPQP |

TABLE 4-continued

Examples of linkage regions of Lck Fusions

| SEQ ID NO. | Description | Amino Acid Sequence |
|---|---|---|
| 45 | CD4 ICD (Intracellu-lar domain of CD4) | VRCRHQQRQAARMSQIKRLLSEKKTC*QC*PH |
| 46 | Lck Unique Domain (N-terminus) | **MGCVCSSNPEDDWMENIDVC*ENC*HYPIVPLDSKISLPIR NGSEVRDPLVTYEGSLPPASPLQDNLV** |
| 47 | CD4-Lck (CD4JM Link) | VRCRHQQRQAARMSQIKRLLSEKKTGTSHY |
| 48 | CD4-Lck (Lck linkage) | VR*AAAS***GCVCSSNPEDDWMENIDVC*ENC*HY** |
| 49 | CD4-Lck (Lck SH3 linkage) | VR*AAAS*DNLVIALHSYEPSHDGDLGFEKGEQLRI |
| 50 | CD4-Lck (Lck Spe linkage) | VRCRHQQRQAARMSQIKRLLSEKKT*GTS*HY |

Key for fusion portions:
Underlined = CD4 originating sequence sequence
Bold = Lck originating
*= CD4 or Lck clasp cysteine
Italicized = Additional linkages (non-CD4 or Lck originating sequences)

FIG. 4 shows IL-2 expression from 58α⁻β⁻ cells expressing the 5c.c7 TCR and indicated CD4-Lck fusions after 16 hours of co-culture with peptide-pulsed APCs.

The present invention is not limited to Lck fusion molecules disclosed herein, e.g., those made based on mouse sequences. The sequences of any of the Lck fusion molecules described herein may be tailored to a particular animal or subject (e.g., human, primate, dog, rat, etc.).

IV. Methods and Applications

The present invention also features applications and methods of use of said CRMs, SCoRs, Lck fusions. For example, the present invention also features cells expressing a SCoR of the present invention. The present invention also features cells expressing a Lck fusion of the present invention. The present invention also features cells expressing a SCoR and/or Lck fusion as part of a $^{5M}$CAR ("redirected" cells). In some embodiments, cells express more than one type of SCoR.

The present invention may feature a method of eliminating or redirecting a target cell. In some embodiments said method comprises introducing a genetically engineered cell as described herein. In some embodiments, the CRM of the genetically engineered cell is specific for a TCR of the target cell, and upon binding of the CRM of the genetically engineered cell to the TCR of the target cell, the genetically engineered cell (a) initiates a signaling cascade that eliminates the target cell, or (b) instructs the target cell to differentiate to a specific effector function.

As an example, in some embodiments, redirected cells may be used to help eliminate autoreactive T cells, regulatory T cells (Tregs) that protect tumor cells by suppressing anti-tumor T cell responses, or any other appropriate T cell. For example, in some embodiments, the CRM is an auto-antigen CRM, and the CRM's target is an autoreactive T cell. The present invention is not limited to the expression of CRMs in T cells.

The present invention is not limited to the MHC portions and TCR portions described herein. For example, the MHC portion may comprise any MHC peptide, e.g., an extracellular domain (or a portion thereof) of any MHC peptide. The TCR portion may comprise any TCR peptide, e.g., a transmembrane domain (or portion thereof) of any TCR peptide. Further, the present invention is not limited to antigens, signaling molecules, and cell surface receptor ligands described herein, e.g., the present invention may be applicable to a wide range of MHC molecules, TCR molecules, antigens, signaling molecules cell surface receptor ligands, etc. In some embodiments, the CRM$^{MHC}$ comprises an MHC portion derived from an extracellular portion of an MHC protein and a TCR portion derived from a transmembrane domain of a TCR protein. In some embodiments, the MHC portion and TCR portion are directly linked. In some embodiments, the MHC portion and TCR portion are separated by a linker. In some embodiments, the linker comprises a glycine-rich linker.

Without wishing to limit the present invention to any theory or mechanism, it is believed that the $^{5M}$CARs of the present invention (e.g., those comprising the SCoRs herein) will be more sensitive and will be under better control as compared to 1 module CARs. Thus, it would be possible to introduce an amount of T cells closer to a physiological level, which may help reduce toxicity and the likelihood of cytokine release syndrome.

The disclosures of the following patents are incorporated in their entirety by reference herein: U.S. Pat. Application No. 2018/0179260, U.S. Pat. Application No. 20140219975; U.S. Pat. Nos. 8,450,112; 7,741,465; 6,319,494; CA 2209300; CA 2104957; EP 0574512; U.S. Pat. Nos. 6,407,221; 6,268,411; U.S. Pat. Application No. 20040258697; EP 1292621; EP 2659893; WO 2011101681; WO 2005054292; EP 1379670: U.S. Pat. Nos. 6,056,952; 6,410,319; 8,524,234; 7,871,817.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures.

In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

EMBODIMENTS

The following embodiments are intended to be illustrative only and not to be limiting in any way.

Embodiment Set 1A

Embodiment 1A: A surrogate co-receptor (SCoR) comprising a first chain comprising: a portion of a T-cell co-receptor linked to a C-terminal of a first binding portion, wherein the portion of the T-cell co-receptor comprises at least a portion of a CD8 chain, a portion of a CD4 chain or a combination thereof, wherein the first binding portion is an Ig domain against a particular target.

Embodiment 2A: The SCoR of embodiment 1A further comprising a second chain comprising a portion of a T-cell co-receptor linked to a C-terminal of a second binding portion, wherein the portion of the T-cell co-receptor comprises at least a portion of a CD8 χηαIV, απOρTIOV Oφ αXΔ4 χηαIV Oρ β χOμβIVαTIOV TηερεOφ, wherein the second binding portion is an Ig domain against a particular target, wherein the second chain of the SCoR is linked to the first chain of the SCoR via a disulfide bond between an extracellular domain (ECD) portion of the T-cell co-receptor of the first chain and an ECD portion of the T-cell co-receptor of the second chain.

Embodiment 3A: The SCoR of embodiment 1A or embodiment 2A, wherein the CD8 chain comprises a CD8α chain, a CD8β chain or a combination thereof.

Embodiment 4A: The SCoR of any one of embodiments 1A-3A, wherein the CD8 chain or the CD4 chain comprise a portion of an extracellular domain (EGO), portion of a transmembrane domain (TMD), portion of an intracellular domain (ICD), or a combination thereof.

Embodiment 5A: The SCoR of embodiment 4A, wherein the ECD of CD4 comprises a D1 domain, a D2 domain, a D3 domain, a D4 domain, or a combination thereof.

Embodiment 6A: The SCoR of embodiment 5A, wherein the binding portion replaces the D1 domain of the ECD.

Embodiment 7A: The SCoR of any one of embodiments 1A-6A, wherein the portion of the CD8 or the portion of the CD4 chain further comprise a Lck protein fused to or replacing an intracellular domain (ICD).

Embodiment 8A: The SCoR of any one of embodiments 1A-7A, wherein the portion of the CD8 or the portion of the CD4 are directly linked or indirectly linked to the respective binding portions.

Embodiment 9A: The SCoR of any one of embodiments 1A-8A, wherein the Ig domains are from a CD80 ligand binding region, a CD86 ligand binding region, or a combination thereof.

Embodiment 10A: The SCoR of any one of embodiments 1A-9A, wherein the Ig domains are antibody fragments.

Embodiment 11A: The SCoR of embodiment 10A, wherein the antibody fragments are antibody Fv fragments.

Embodiment 12A: The SCoR of embodiment 11A, wherein the antibody Fv fragments are heavy chain domains, light chain domains or a combination thereof.

Embodiment 13A: The SCoR of embodiment 10A, wherein the antibody fragments are wild type fragments or from a standard antibody.

Embodiment 14A: The SCoR of embodiment 10A, wherein the antibody fragments have at least one mutation compared to their wild type sequences or standard antibody sequences.

Embodiment 15A: The SCoR of embodiment 14A, wherein the antibody fragments with at least one mutation have a lower binding affinity than their wild type counterparts.

Embodiment 16A: The SCoR of embodiment 10A, wherein the antibody fragments have a germline sequence.

Embodiment 17A: The SCoR of embodiment 10A, wherein the antibody fragments are derived from a sequence obtained by tuning for particular binding kinetics.

Embodiment 18A: An engineered cell expressing on its surface at least one surrogate co-receptor according to any one of embodiments 1A-17A Embodiment 19A: An engineered cell co-expressing on its surface: (a) at least one chimeric receptor (CRM) comprising a major histocompatibility complex (MHC) portion comprised of at least a portion of an extracellular domain of an MHC protein fused to the N-terminal of a T cell receptor (TCR) portion, comprised of at least a portion of a transmembrane domain and at least a portion of a cytoplasmic domain of a TOR protein and (b) at least one SCoR according to any one of embodiments 1A-17A, wherein the SCoR is specific for a second epitope of the TCR.

Embodiments 20A: An engineered cell co-expressing on its surface: (a) a chimeric receptor (CRM) comprising a major histocompatibility complex (MHC) portion comprised of at least a portion of an extracellular domain of an MHC protein fused to the N-terminal of a T cell receptor (TCR) portion, comprised of at least a portion of a transmembrane domain and at least a portion of a cytoplasmic domain of a TCR protein; and (b) a surrogate coreceptor according to any one of embodiments 1A-17A, the SCoR is specific for a second epitope of the TCR.

Embodiment 21A: The engineered cell of embodiment 19A or embodiment 20A, wherein the MHC portion is indirectly or directly fused to the TCR portion.

Embodiment 22A: The engineered cell of embodiment 21A, wherein the MHC portion is indirectly fused to the TCR portion via a linker.

Embodiment 23A: The engineered cell of embodiment 19A or embodiment 20A, wherein the TCR portion further comprises at least a portion of an extracellular domain of the TCR protein.

Embodiment 24A: The engineered cell of embodiment 19A or embodiment 20A, wherein the MHC portion further comprises a targeted peptide, wherein the targeted peptide is integrated into the MHC portion, or directly or indirectly fused to the MHC portion.

Embodiment 25A: The engineered cell of embodiment 19A or embodiment 20A, wherein the MHC protein comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a fragment thereof, or a combination thereof.

Embodiment 26A: The engineered cell of embodiment 19A or embodiment 20A, wherein the MHC molecule comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a peptide that is at least 90% identical to HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, or H2-EK beta, a fragment thereof, or a combination thereof.

Embodiment 27A: The engineered cell of embodiment 19A or embodiment 20A, wherein the TCR protein comprises TRAC, TRBC1, TRBC2, TRDC, TRGC1, TRGC2, TCRA, TCB1, TCB2, TCC1, TCC2, TCC3, TCC4, a fragment thereof, or a combination thereof.

Embodiment 28A: The engineered cell of embodiment 19A or embodiment 20A, wherein the TCR molecule comprises TRAC, TRBC1, TRBC2, TRDC, TRGC1, TRGC2, TCRA, TCB1, TCB2, TCC1, TCC2, TCC3, TCC4, a peptide that is at least 90% identical to TRAC, TRBC1, TRBC2, TRDC, TRGC1, TRGC2, TCRA, TCB1, TCB2, TCC1, TCC2, TCC3, or TCC4, a fragment thereof, or a combination thereof.

Embodiment 29A: The engineered cell of embodiment 19A or embodiment 20A, wherein the CRM can complex with a CD3 subunit.

Embodiment 30A: The engineered cell of embodiment 19A or embodiment 20A further co-expressing a second SCoR.

Embodiment 31A: A vector encoding a surrogate co-receptor according to any one of embodiments 1A-17A.

Embodiment 32A: A DNA sequence encoding a surrogate co-receptor according to any one of embodiments 1A-17A.

Embodiment 33A: A protein sequence encoding a surrogate co-receptor according to any one of embodiments 1A-17A.

Embodiment 34A: A method of eliminating or redirecting a target cell, said method comprising introducing a genetically engineered cell according to any one of embodiments 19A-30A, wherein the CRM of the genetically engineered cell is specific for a TCR of the target cell, wherein upon binding of the CRM of the genetically engineered cell to the TCR of the target cell, the genetically engineered cell (a) initiates a signaling cascade that eliminates the target cell, or (b) instructs the target cell to differentiate to a specific effector function.

Embodiment Set 1B

Embodiment 1B: A surrogate co-receptor (SCoR) comprising: (a) a first chain comprising a portion of a T-cell co-receptor linked to the C-terminal of a first binding portion, wherein the portion of the T-cell co-receptor comprises at least a portion of a CD8 χηαIV, α πOρTIOV OCP α XΔ4 χηαIV Oρ α χOμβIVαTIOV TηεpεOCP, wherein the first binding portion is an Ig domain against a particular target and (b) a second chain comprising a portion of a T-cell co-receptor linked to the C-terminal of a second binding portion, wherein the portion of the T-cell co-receptor comprises at least a portion of a CD8 χηαIV, α πOρTIOV OCP α XΔ4 χηαIV Oρ α χOμβIVαTIOV TηεpεOCP, wherein the second binding portion is an Ig domain against a particular target.

Embodiment 2B: The SCoR of embodiment 1B, wherein the second chain of the SCoR is linked to the first chain of the SCoR via a disulfide bond between an extracellular domain (ECD) portion of the T-cell co-receptor of the first chain and an ECD portion of the T-cell co-receptor of the second chain.

Embodiment 3B: The SCoR of embodiment 1B, wherein the CD8 chain comprises a CD8α chain, a CD8β chain or a combination thereof.

Embodiment 4B: The SCoR of embodiment 1B or embodiment 3B, wherein the CD8 chain or the CD4 chains comprise a portion of an extracellular domain (ECD), portion of a transmembrane domain (TMD), portion of an intracellular domain (ICD), or a combination thereof.

Embodiment 5B: The SCoR of any one of embodiments 1B-4B, wherein the portion of the CD8 chain or the portion of the CD4 chains further comprise a Lck protein fused to or replacing the ICD.

Embodiment 6B: The SCoR of any one of embodiments 1B-5B, wherein the CD8 portions or the CD4 portions are directly linked or indirectly linked to the respective binding portions.

Embodiment 7B: The SCoR of any one of embodiments 1B-6B, wherein the Ig domains are from a CD80 receptor binding region, a CD86 receptor binding region, or a combination thereof.

Embodiment 8B: The SCoR of any one of embodiments 1B-6B, wherein the Ig domains are antibody fragments.

Embodiment 9B: The SCoR of embodiment 8B, wherein the antibody fragments are antibody Fv fragments.

Embodiment 10B: The SCoR of embodiment 9B, wherein the antibody Fv fragments are heavy chain domains, light chain domains or a combination thereof.

Embodiment 11B: The SCoR of embodiment 8B, wherein the antibody fragments are wild type fragments or from a standard antibody.

Embodiment 12B: The SCoR of embodiment 8B, wherein the antibody fragments have at least one mutation compared to their wild type sequences or standard antibody sequences.

Embodiment 13B: The SCoR of embodiment 12B, wherein the antibody fragments with at least one mutation have a lower binding affinity than their wild type counterparts.

Embodiment 14B: The SCoR of embodiment 8B, wherein the antibody fragments have a germline sequence.

Embodiment 15B: The SCoR of embodiment 8B, wherein the antibody fragments are derived from a sequence obtained by tuning for particular binding kinetics Embodiment 16B: An engineered cell expressing on its surface at least one surrogate co-receptor according to any one of embodiments 1B-15B.

Embodiment 17B: An engineered cell co-expressing on its surface: (a) at least one chimeric receptor (CRM) comprising a major histocompatibility complex (MHC) portion comprised of at least a portion of an extracellular domain of an MHC protein fused to the N-terminal of a cell receptor (TCR) portion, comprised of at least a portion of a transmembrane domain and at east a portion of a cytoplasmic domain of a TOR protein and (b) at least one SCoR according to any one of embodiments 1B-15B, wherein the SCoR is specific for a second epitope of the TCR.

Embodiment 18B: An engineered cell co-expressing on its surface: (a) a chimeric receptor (CRM) comprising a major histocompatibility complex (MHC) portion comprised of at least a portion of an extracellular domain of an MHC protein fused to the N-terminal of a T cell receptor (TOR) portion, comprised of at least a portion of a transmembrane domain and at least a portion of a cytoplasmic domain of a TCR protein; and (b) a surrogate coreceptor according to any one of embodiments 1B-15B, the SCoR is specific for a second epitope of the TCR.

Embodiment 19B: The engineered cell of embodiment 17B or embodiment 18B, wherein the MHC portion is indirectly or directly fused to the TCR portion.

Embodiment 20B: The engineered cell of embodiment 19B, wherein the MHC portion is indirectly fused to the TCR portion via a linker.

Embodiment 21B: The engineered cell of embodiment 17B or embodiment 18B, wherein the TCR portion comprises at least a portion of a transmembrane domain of the TCR protein and the MHC portion comprises at least a portion of an extracellular domain of the MHC protein.

Embodiment 22B: The engineered cell of embodiment 17B or embodiment 18B, wherein the TCR portion comprises at least a portion of a transmembrane domain and at least a portion of a cytoplasmic domain of a TCR protein, and the MHC portion comprises at least a portion of an extracellular domain of the MHC protein.

Embodiment 23B: The engineered cell of embodiment 17B or embodiment 18B, wherein the CRM further comprises a peptide antigen integrated into the MHC portion, or directly or indirectly fused to the MHC portion.

Embodiment 24B: The engineered cell of embodiment 17B or embodiment 18B, wherein the MHC protein comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a fragment thereof, or a combination thereof.

Embodiment 25B: The engineered cell of embodiment 17B or embodiment 18B, wherein the MHC molecule comprises HLA-A, HLA-B, HLA-C, HLA-DPA1, HLA-DPB1, HLA-DQA1 HLA-DQB1, HLA-DRA, HLA-DRB, H2-Aa, H2-B1, H2-K1, H2-EB beta, H2-EK alpha, H2-EK beta, a peptide that is at least 90% identical to HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, or H2-EK beta, a fragment thereof, or a combination thereof.

Embodiment 26B: The engineered cell of embodiment 17B or embodiment 18B, wherein the TCR molecule comprises TRAC, TRBC1, TRBC2, TRDC, TRGC1 TRGC2, TCRA, TCB1, TCB2, TCC1, TCC2, TCC3, TCC4, a fragment thereof, or a combination thereof.

Embodiment 27B: The engineered cell of embodiment 17B or embodiment 18B, wherein the TCR molecule comprises TRAC, TRBC1, TRBC2, TRDC, TRGC1, TRGC2, TCRA, TCB1, TCB2, TCC1, TCC2, TCC3, TCC4, a peptide that is at least 90% identical to TRAC, TRBC1, TRBC2, TRDC, TRGC1, TRGC2, TCRA, TCB1 TCB2, TCC1, TCC2 TCC3, or TCC4, a fragment thereof, or a combination thereof.

Embodiment 28B: The engineered cell of embodiment 17B or embodiment 18B, wherein the CRM can complex with a CD3 subunit.

Embodiment 29B: The engineered cell of embodiment 17B or embodiment 18B, further co-expressing a second SCoR.

Embodiment 30B: A vector encoding a surrogate co-receptor according to any one of embodiments 1B-15B.

Embodiment 31B: A DNA sequence encoding a surrogate co-receptor according to any one of embodiments 1B-15B.

Embodiment 32B: A protein sequence encoding a surrogate co-receptor according to any one of embodiments 1B-15B.

Embodiment 33B: A method of eliminating or redirecting a target cell, said method comprising introducing a genetically engineered cell according to any one of embodiments 16B-29B, wherein the CRM of the genetically engineered cell is specific for a TCR of the target cell, wherein upon binding of the CRM of the genetically engineered cell to the TCR of the target cell, the genetically engineered cell (a) initiates a signaling cascade that eliminates the target cell, or (b) instructs the target cell to differentiate to a specific effector function.

Embodiment Set 1C

Embodiment 1C: A surrogate co-receptor (SCoR) comprising: a portion of a T-cell co-receptor linked to the C-terminal of a binding portion, wherein the portion of the T-cell co-receptor comprises at least a portion a of a CD4 chain, wherein the binding portion is an Ig domain against a particular target.

Embodiment 2C: The SCoR of embodiment 1C: wherein portion of the CD4 chain comprise a portion of an extracellular domain (ECD), portion of a transmembrane domain (TMD), portion of an intracellular domain (ICD), or a combination thereof.

Embodiment 3C: The SCoR of embodiment 2C, wherein the ECD comprises a D1 domain, a D2 domain, a D3 domain, a D4 domain, or a combination thereof.

Embodiment 4C: The SCoR of embodiment 3C, wherein the binding portion replaces the D1 domain of the ECD.

Embodiment 5C: The SCoR of embodiment 2C, wherein the portion of the CD4 chain further comprises a Lck protein fused to or replacing the ICD.

Embodiment 6C: The SCoR of any one of embodiments 1C-5C, wherein the CD4 portion is directly linked or indirectly linked to the respective binding portions.

Embodiment 7C: The SCoR of any one of embodiments 1C-6C, wherein the Ig domains are from a CD80 ligand binding region, a CD86 ligand binding region or a combination thereof.

Embodiment 8C: The SCoR of any one of embodiments 1C-7C, wherein the Ig domains are antibody fragments.

Embodiment 9C: The SCoR of embodiment 8C, wherein the antibody fragments are antibody Fv fragments.

Embodiment 10C: The SCoR of embodiment 9C, wherein the antibody Fv fragments are heavy chain domains, light chain domains or a combination thereof.

Embodiment 11C: The SCoR of embodiment 80, wherein the antibody fragments are wild type fragments or from a standard antibody Embodiment 12C: The SCoR of embodiment 8C, wherein the antibody fragments have at least one mutation compared to their wild type sequences or standard antibody sequences.

Embodiment 13C: The SCoR of embodiment 12C, wherein the antibody fragments with at least one mutation have a lower binding affinity than their wild type counterparts.

Embodiment 14C: The SCoR of embodiment 8C, wherein the antibody fragments have a germline sequence.

Embodiment 15C: The SCoR of embodiment 8C, wherein the antibody fragments are derived from a sequence obtained by tuning for particular binding kinetics.

Embodiment 16C: An engineered cell expressing on its surface at least one surrogate co-receptor according to any one of embodiments 1C-15C.

Embodiment 17C: An engineered cell co-expressing on its surface: (a) at least one chimeric receptor (CRM) comprising a major histocompatibility complex (MHC) portion comprised of at least a portion of an extracellular domain of an MHC protein fused to the N-terminal of a T cell receptor (TCR) portion, comprised of at least a portion of a transmembrane domain and at least a portion of a cytoplasmic domain of a TCR protein and (b) at least one SCoR according to any one of embodiments 10-150, wherein the SCoR is specific for a second epitope of the TCR.

Embodiment 18C: An engineered cell co-expressing on its surface: (a) a chimeric receptor (CRM) comprising a major histocompatibility complex (MHC) portion comprised of at least a portion of an extracellular domain of an MHC protein fused to the N-terminal of a T cell receptor (TOR) portion, comprised of at least a portion of a transmembrane domain and at least a portion of a cytoplasmic domain of a TOR protein: and (b) a surrogate coreceptor according to any one of embodiments 10-150, the SCoR is specific for a second epitope of the TCR.

Embodiment 19C: The engineered cell of embodiment 17C or embodiment 18C wherein the MHC portion is indirectly or directly fused to the TCR portion.

Embodiment 20C: The engineered cell of embodiment 19C, wherein the MHC portion is indirectly fused to the TCR portion via a linker.

Embodiment 21C: The engineered cell of embodiment 17C or embodiment 18C, wherein the TCR portion comprises at least a portion of a transmembrane domain of the TCR protein and the MHC portion comprises at least a portion of an extracellular domain of the MHC protein.

Embodiment 22C: The engineered cell of embodiment 17C or embodiment 18C, wherein the TCR portion comprises at least a portion of a transmembrane domain and at least a portion of a cytoplasmic domain of a TCR protein, and the MHC portion comprises at least a portion of an extracellular domain of the MHC protein.

Embodiment 23C: The engineered cell of embodiment 170 or embodiment 18C, wherein the CRM further comprises a peptide antigen integrated into the MHC portion, or directly or indirectly fused to the MHC portion.

Embodiment 24C: The engineered cell of embodiment 17C or embodiment 18C, wherein the MHC protein comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a fragment thereof, or a combination thereof.

Embodiment 25C: The engineered cell of embodiment 17C or embodiment 18C wherein the MHC molecule comprises HLA-A, HLA-B, HLA-C, HLA-DPA1, HLA-DPB1 HLA-DQA1, HLA-DQB1, HLA-DRA, HLA-DRB, H2-Aa, H2-B1, H2-K1, H2-EB beta, H2-EK alpha, H2-EK beta, a peptide that is at least 90% identical to HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, or H2-EK beta, a fragment thereof, or a combination thereof.

Embodiment 26C: The engineered cell of embodiment 17C or embodiment 18C, wherein the TCR molecule comprises TRAC, TRBC1, TRBC2, TRDC, TRGC1, TRGC2, TCRA, TCB1, TCB2, TCC1, TCC2, TCC3, TCC4, a fragment thereof, or a combination thereof.

Embodiment 27C: The engineered cell of embodiment 17C or embodiment 18C, wherein the TCR molecule comprises TRAC, TRBC1, TRBC2, TRDC, TRGC1, TRGC2, TCRA, TCB1, TCB2, TCC1, TCC2, TCC3, TCC4, a peptide that is at least 90% identical to TRAC, TRBC1, TRBC2, TRDC, TRGC1, TRGC2, TCRA, TCB1, TCB2, TCC1, TCC2, TCC3, or TCC4, a fragment thereof, or a combination thereof.

Embodiment 28C: The engineered cell of embodiment 17C or embodiment 18C wherein the CRM can complex with a CD3 subunit.

Embodiment 29C: The engineered cell of embodiment 17C or embodiment 18C, further co-expressing a second SCoR.

Embodiment 30C: A vector encoding a surrogate co-receptor according to any one of embodiments 1C-15C.

Embodiment 31C: A DNA sequence encoding a surrogate co-receptor according to any one of embodiments 1C-15C.

Embodiment 32C: A protein sequence encoding a surrogate co-receptor according to any one of embodiments 1C-15C.

Embodiment 33C: A method of eliminating or redirecting a target cell, said method comprising introducing a genetically engineered cell according to any one of embodiments 17C-29C, wherein the CRM of the genetically engineered cell is specific for a TCR of the target cell, wherein upon binding of the CRM of the genetically engineered cell to the TCR of the target cell, the genetically engineered cell (a) initiates a signaling cascade that eliminates the target cell, or (b) instructs the target cell to differentiate to a specific effector function.

Embodiment Set 1D

Embodiment 1D: A surrogate co-receptor (SCoR) comprising: (a) an a chain comprising a first binding portion and a CD8α portion, wherein the first binding portion is an Ig domain against a particular target and the CD8α portion is at least a portion of a CD8α χηαιν and (b) a β chain comprising a second binding portion and a CD8β portion, wherein the second binding portion comprises an Ig domain against a particular target and the CD8β portion is at least a portion of a CD8β chain; wherein the CD8 portions are linked C-terminal to the respective binding portions.

Embodiment 2D: The SCoR of embodiment 1D, wherein the β chain of the SCoR is linked to the α chain of the SCoR via a disulfide bond between an extracellular domain (ECD) portion of the CD8α chain and an ECD portion of the CD8β chain.

Embodiment 3D: The SCoR of embodiment 1D or embodiment 2D, wherein the CD8 portion comprises a portion of an extracellular domain (ECD), portion of a transmembrane domain (TMD), portion of an intracellular domain (ICD), or a combination thereof.

Embodiment 4D: The SCoR of embodiment 3D, wherein the CD8 portion further comprises a Lck protein fused to or replacing the ICD.

Embodiment 5D: The SCoR of embodiment 3D, wherein the portion of the ICD of CD8 is replaced with at least a portion of a CD4 intracellular domain.

Embodiment 6D: The SCoR of embodiment 3D, wherein the portion of the TMD of CD8 is replaced with at least a portion of a CD4 transmembrane domain.

Embodiment 7D: The SCoR of embodiment 3D, wherein the portion of the ICD of CD8 is replaced with at least a portion of a CD4 ICD and the portion of the TMD of CD8 is replaced with at least a portion of a CD4 TMD.

Embodiment 8D: The SCoR of embodiment 5D or embodiment 7D, wherein the ICD of CD4 is fused to a Lck protein.

Embodiment 9D: The SCoR of any one of embodiments 1D-8D, wherein the CD8 portions are directly linked or indirectly linked to the respective binding portions.

Embodiment 10D: The SCoR of any one of embodiments 1D-90, wherein the Ig domains are from a CD80 ligand binding region, a CD86 ligand binding region, or a combination thereof.

Embodiment 11D: The SCoR of any one of embodiments 1D-9D, wherein the Ig domains are antibody fragments.

Embodiment 12D: The SCoR of embodiment 11D, wherein the antibody fragments are antibody Fv fragments Embodiment 13D: The SCoR of embodiment 12D, wherein the antibody Fv fragments are heavy chain domains, light chain domains or a combination thereof Embodiment 14D: The SCoR of embodiment 11D, wherein the antibody fragments are wild type fragments or from a standard antibody.

Embodiment 15D: The SCoR of embodiment 11D, wherein the antibody fragments have at least one mutation compared to their wild type sequences or standard antibody sequences.

Embodiment 16D: The SCoR of embodiment 15D, wherein the antibody fragments with at least one mutation have a lower binding affinity than their wild type counterparts.

Embodiment 17D: The SCoR of embodiment 11D, wherein the antibody fragments have a germline sequence.

Embodiment 18D: The SCoR of embodiment 11D, wherein the antibody fragments are derived from a sequence obtained by tuning for particular binding kinetics Embodiment 19D: An engineered cell expressing on its surface at least one surrogate co-receptor according to any one of embodiments 1D-18D.

Embodiment 20D: An engineered cell co-expressing on its surface: (a) at least one chimeric receptor (CRM) comprising a major histocompatibility complex (MHC) portion comprised of at least a portion of an extracellular domain of an MHC protein fused to the N-terminal of a T cell receptor (TCR) portion, comprised of at least a portion of a transmembrane domain and at least a portion of a cytoplasmic domain of a TCR protein and (b) at least one SCoR according to any one of embodiments 1D-18D, wherein the SCoR is specific for a second epitope of the TCR.

Embodiment 21D: An engineered cell co-expressing on its surface: (a) a chimeric receptor (CRM) comprising a major histocompatibility complex (MHC) portion comprised of at least a portion of an extracellular domain of an MHC protein fused to the N-terminal of a T cell receptor (TOR) portion, comprised of at least a portion of a transmembrane domain and at least a portion of a cytoplasmic domain of a TOR protein; and (b) a surrogate coreceptor according to any one of embodiments 1D-18D, the SCoR is specific for a second epitope of the TCR.

Embodiment 22D: The engineered cell of embodiment 20D or embodiment 21D, wherein the MHC portion is indirectly or directly fused to the TCR portion.

Embodiment 23D: The engineered cell of embodiment 22D, wherein the MHC portion is indirectly fused to the TCR portion via a linker.

Embodiment 24D: The engineered cell of embodiment 20D or embodiment 21D, wherein the TCR portion comprises at least a portion of a transmembrane domain of the TCR protein and the MHC portion comprises at least a portion of an extracellular domain of the MHC protein.

Embodiment 25D: The engineered cell of embodiment 20D or embodiment 21D, wherein the TCR portion comprises at least a portion of a transmembrane domain and at least a portion of a cytoplasmic domain of a TCR protein, and the MHC portion comprises at least a portion of an extracellular domain of the MHC protein.

Embodiment 26D: The engineered cell of embodiment 20D or embodiment 21D, wherein the CRM further comprises a peptide antigen integrated into the MHC portion, or directly or indirectly fused to the MHC portion.

Embodiment 27D: The engineered cell of embodiment 20D or embodiment 21D, wherein the MHC protein comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a fragment thereof, or a combination thereof.

Embodiment 28D: The engineered cell of embodiment 20D or embodiment 21D, wherein the MHC molecule comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a peptide that is at least 90% identical to HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, or H2-EK beta, a fragment thereof, or a combination thereof.

Embodiment 29D: The engineered cell of embodiment 20D or embodiment 21D, wherein the TCR molecule comprises TRAC, TRBC1, TRBC2, TRDC, TRGC1, TRGC2, TCRA, TCB1, TCB2, TCC1, TCC2, TCC3, TCC4, a fragment thereof, or a combination thereof.

Embodiment 30D: The engineered cell of embodiment 20D or embodiment 21D, wherein the TCR molecule comprises TRAC, TRBC1, TRBC2, TRDC, TRGC1, TRGC2, TCRA, TCB1, TCB2, TCC1, TCC2, TCC3. TCC4, a peptide that is at least 90% identical to TRAC, TRBC1, TRBC2, TRDC, TRGC1, TRGC2, TCRA, TCB1, TCB2, TCC1, TCC2, TCC3, or TCC4, a fragment thereof, or a combination thereof.

Embodiment 31D: The engineered cell of embodiment 20D or embodiment 21D wherein the CRM can complex with a CD3 subunit.

Embodiment 32D: The engineered cell of embodiment 20D or embodiment 21D further co-expressing a second SCoR.

Embodiment 33D: A vector encoding a surrogate co-receptor according to any one of embodiments 1D-18D.

Embodiment 34D: A DNA sequence encoding a surrogate co-receptor according to any one of embodiments 1D-18D.

Embodiment 35D: A protein sequence encoding a surrogate co-receptor according to any one of embodiments 1D-18D.

Embodiment 36D: A method of eliminating or redirecting a target cell, said method comprising introducing a genetically engineered cell according to any one of embodiments 20D-32D, wherein the CRM of the genetically engineered cell is specific for a TCR of the target cell, wherein upon binding of the CRM of the genetically engineered cell to the TCR of the target cell, the genetically engineered cell (a) initiates a signaling cascade that eliminates the target cell, or (b) instructs the target cell to differentiate to a specific effector function.

---

What is claimed is:

1. A surrogate co-receptor (SCoR) comprising a first chain comprising: a portion of a T-cell co-receptor linked to a C-terminal of a first binding portion, wherein the portion of the T-cell co-receptor comprises at least a portion of a CD8 chain, a portion of a CD4 chain or a combination thereof, wherein the first binding portion is an Ig domain against a particular target expressed on a surface of a target cell.

2. The SCoR of claim 1 further comprising a second chain comprising a portion of a T-cell co-receptor linked to a C-terminal of a second binding portion, wherein the portion of the T-cell co-receptor comprises at least a portion of a CD8 chain, a portion of a CD4 chain or a combination thereof, wherein the second binding portion is an Ig domain against a particular target expressed on a surface of a target cell, wherein the second chain of the SCoR is linked to the first chain of the SCoR via a disulfide bond between an extracellular domain (ECD) portion of the T-cell co-receptor of the first chain and an ECD portion of the T-cell co-receptor of the second chain.

3. The SCoR of claim 1, wherein the CD8 chain comprises a CD8α chain, a CD8β chain or a combination thereof.

4. The SCoR of claim 1, wherein the CD8 chain or the CD4 chain comprises a portion of an extracellular domain (ECD), a portion of a transmembrane domain (TMD), a portion of an intracellular domain (ICD), or a combination thereof.

5. The SCoR of claim 4, wherein the ECD of CD4 comprises a D1 domain, a D2 domain, a D3 domain, a D4 domain, or a combination thereof.

6. The SCoR of claim 5, wherein the first binding portion replaces the D1 domain of the ECD.

7. The SCoR of claim 1, wherein the portion of the CD8 or the portion of the CD4 chain further comprise a Lck protein fused to or replacing an intracellular domain (ICD).

8. The SCoR of claim 1, wherein the portion of the CD8 or the portion of the CD4 are directly linked or indirectly linked to the respective binding portions.

9. The SCoR of claim 1, wherein the Ig domains are from a CD80 ligand binding region, a CD86 ligand binding region, or a combination thereof.

10. The SCoR of claim 1, wherein the Ig domains are antibody fragments.

11. The SCoR of claim 10, wherein the antibody fragments are antibody Fv fragments, wherein the antibody Fv fragments are heavy chain domains, light chain domains, or a combination thereof.

12. An engineered cell expressing on its surface at least one surrogate co-receptor according to claim 1.

13. An engineered cell co-expressing on its surface:
a. at least one chimeric receptor (CRM) comprising (i) a class I major histocompatibility complex (MHC) portion comprised of at least a portion of an extracellular domain of a class I MHC protein, a beta2 microglobulin and a targeted peptide fused to the N-terminal of a T cell receptor (TCR) portion, comprised of at least a portion of a transmembrane domain and at least a portion of a cytoplasmic domain of a TCR protein; or (ii) a class II MHC portion comprised of at least a portion of an extracellular domain of a class II MHC protein and a targeted peptide fused to the N-terminal of a TCR portion comprises of at least portion of a transmembrane domain and at least a portion of a cytoplasmic domain of a TCR protein;
wherein in (i) and (ii), first the targeted peptide of the MHC portion is presented in the MHC (pMHC), second the pMHC is specific for a first epitope of a TCR, third the pMHC can complex with said TCR; and
b. at least one SCoR according to claim 1, wherein the SCoR is specific for a second epitope of the TCR.

14. The engineered cell of claim 13, wherein the MHC portion is indirectly or directly fused to the TCR portion.

15. The engineered cell of claim 13, wherein the TCR portion further comprises at least a portion of an extracellular domain of the TCR protein.

16. The engineered cell of claim 13, wherein the targeted peptide is integrated into the MHC portion, or directly or indirectly fused to the MHC portion.

17. The engineered cell of claim 13, wherein the MHC protein comprises HLA-A, HLA-B, HLA-C, HLA-DPA1, HLA-DPB1, HLA-DQA1, HLA-DQB1, HLA-DRA, HLA-DRB, H2-Aa, H2-B1, H2-K1, H2-EB beta, H2-EK alpha, H2-EK beta, a fragment thereof, or a combination thereof.

18. The engineered cell of claim 13, wherein the TCR protein comprises TRAC, TRBC1, TRBC2, TRDC, TRGC1, TRGC2, TCRA, TCB1, TCB2, TCC1, TCC2, TCC3, TCC4, a fragment thereof, or a combination thereof.

19. A method of eliminating or redirecting a target cell, said method comprising introducing a genetically engineered cell according to claim 13, wherein the CRM of the genetically engineered cell is specific for a TCR of the target cell, wherein upon binding of the CRM of the genetically engineered cell to the TCR of the target cell, the genetically engineered cell (a) initiates a signaling cascade that eliminates the target cell, or (b) instructs the target cell to differentiate to a specific effector function.

20. A surrogate co-receptor (SCoR) comprising a first chain comprising: a portion of a T-cell co-receptor linked to a C-terminal of a first binding portion, wherein the portion of the T-cell co-receptor comprises at least a portion of a CD8 chain, a portion of a CD4 chain or a combination thereof, wherein the first binding portion is an Ig domain against a particular target, wherein the portion of the CD8 or the portion of the CD4 chain further comprise a Lck protein fused to or replacing an intracellular domain (ICD).

* * * * *

SEQUENCE LISTING

<160> NUMBER OF SEQ ID NOS: 53

<210> SEQ ID NO 1
<211> LENGTH: 365
<212> TYPE: PRT
<213> ORGANISM: Homo sapiens

<400> SEQUENCE: 1

```
Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Tyr Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Arg Asn Thr Arg Asn Val Lys Ala Gln Ser Gln
                85                  90                  95

Thr Asp Arg Val Asp Leu Gly Thr Leu Arg Gly Tyr Tyr Asn Gln Ser
                100                 105                 110

Glu Ala Gly Ser His Thr Ile Gln Met Met Tyr Gly Cys Asp Val Gly
            115                 120                 125

Ser Asp Gly Arg Phe Leu Arg Gly Tyr Arg Gln Asp Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Trp Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255
```

-continued

Thr Arg Pro Ala Gly Asp Gly Thr Phe Gln Lys Trp Val Ala Val Val
            260                 265                 270

Val Pro Ser Gly Gln Glu Gln Arg Tyr Thr Cys His Val Gln His Glu
            275                 280                 285

Gly Leu Pro Lys Pro Leu Thr Leu Arg Trp Glu Pro Ser Ser Gln Pro
            290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
            325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
            355                 360                 365

<210> SEQ ID NO 2
<211> LENGTH: 362
<212> TYPE: PRT
<213> ORGANISM: Homo sapiens

<400> SEQUENCE: 2

Met Arg Val Thr Ala Pro Arg Thr Val Leu Leu Leu Leu Trp Gly Ala
1               5                   10                  15

Val Ala Leu Thr Glu Thr Trp Ala Gly Ser His Ser Met Arg Tyr Phe
            20                  25                  30

Tyr Thr Ala Met Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
            50                  55                  60

Ala Ser Pro Arg Thr Glu Pro Arg Ala Pro Trp Ile Glu Gln Glu Gly
65                  70                  75                  80

Pro Glu Tyr Trp Asp Arg Asn Thr Gln Ile Phe Lys Thr Asn Thr Gln
                85                  90                  95

Thr Tyr Arg Glu Asn Leu Arg Ile Ala Leu Arg Tyr Tyr Asn Gln Ser
            100                 105                 110

Glu Ala Gly Ser His Thr Trp Gln Thr Met Tyr Gly Cys Asp Val Gly
            115                 120                 125

Pro Asp Gly Arg Leu Leu Arg Gly His Asn Gln Tyr Ala Tyr Asp Gly
            130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Leu Arg Ala Tyr Leu Glu Gly Leu Cys Val Glu Trp Leu
            180                 185                 190

Arg Arg His Leu Glu Asn Gly Lys Glu Thr Leu Gln Arg Ala Asp Pro
            195                 200                 205

Pro Lys Thr His Val Thr His His Pro Val Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val

```
                    260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
        290                 295                 300

Thr Ile Pro Ile Val Gly Ile Val Ala Gly Leu Ala Val Leu Ala Val
305                 310                 315                 320

Val Val Ile Gly Ala Val Val Ala Thr Val Met Cys Arg Arg Lys Ser
                325                 330                 335

Ser Gly Gly Lys Gly Gly Ser Tyr Ser Gln Ala Ala Ser Ser Asp Ser
                340                 345                 350

Ala Gln Gly Ser Asp Val Ser Leu Thr Ala
                355                 360

<210> SEQ ID NO 3
<211> LENGTH: 366
<212> TYPE: PRT
<213> ORGANISM: Homo sapiens

<400> SEQUENCE: 3

Met Arg Val Met Ala Pro Arg Thr Leu Ile Leu Leu Leu Ser Gly Ala
1               5                   10                  15

Leu Ala Leu Thr Glu Thr Trp Ala Cys Ser His Ser Met Arg Tyr Phe
                20                  25                  30

Asp Thr Ala Val Ser Arg Pro Gly Arg Gly Glu Pro Arg Phe Ile Ser
            35                  40                  45

Val Gly Tyr Val Asp Asp Thr Gln Phe Val Arg Phe Asp Ser Asp Ala
        50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Ala Asp Arg Val Asn Leu Arg Lys Leu Arg Gly Tyr Tyr Asn Gln Ser
            100                 105                 110

Glu Asp Gly Ser His Thr Leu Gln Trp Met Tyr Gly Cys Asp Leu Gly
        115                 120                 125

Pro Asp Gly Arg Leu Leu Arg Gly Tyr Asp Gln Ser Ala Tyr Asp Gly
        130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu His
        195                 200                 205

Pro Lys Thr His Val Thr His His Pro Val Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
                260                 265                 270
```

```
Val Pro Ser Gly Glu Glu Gln Arg Tyr Thr Cys His Val Gln His Glu
    275                 280                 285

Gly Leu Pro Glu Pro Leu Thr Leu Arg Trp Glu Pro Ser Ser Gln Pro
    290                 295                 300

Thr Ile Pro Ile Val Gly Ile Val Ala Gly Leu Ala Val Leu Ala Val
305                 310                 315                 320

Leu Ala Val Leu Gly Ala Val Met Ala Val Val Met Cys Arg Arg Lys
                325                 330                 335

Ser Ser Gly Gly Lys Gly Gly Ser Cys Ser Gln Ala Ala Ser Ser Asn
            340                 345                 350

Ser Ala Gln Gly Ser Asp Glu Ser Leu Ile Ala Cys Lys Ala
        355                 360                 365

<210> SEQ ID NO 4
<211> LENGTH: 260
<212> TYPE: PRT
<213> ORGANISM: Homo sapiens

<400> SEQUENCE: 4

Met Arg Pro Glu Asp Arg Met Phe His Ile Arg Ala Val Ile Leu Arg
1               5                   10                  15

Ala Leu Ser Leu Ala Phe Leu Leu Ser Leu Arg Gly Ala Gly Ala Ile
            20                  25                  30

Lys Ala Asp His Val Ser Thr Tyr Ala Ala Phe Val Gln Thr His Arg
        35                  40                  45

Pro Thr Gly Glu Phe Met Phe Glu Phe Asp Glu Asp Glu Met Phe Tyr
    50                  55                  60

Val Asp Leu Asp Lys Lys Glu Thr Val Trp His Leu Glu Glu Phe Gly
65                  70                  75                  80

Gln Ala Phe Ser Phe Glu Ala Gln Gly Gly Leu Ala Asn Ile Ala Ile
                85                  90                  95

Leu Asn Asn Asn Leu Asn Thr Leu Ile Gln Arg Ser Asn His Thr Gln
            100                 105                 110

Ala Thr Asn Asp Pro Pro Glu Val Thr Val Phe Pro Lys Glu Pro Val
        115                 120                 125

Glu Leu Gly Gln Pro Asn Thr Leu Ile Cys His Ile Asp Lys Phe Phe
    130                 135                 140

Pro Pro Val Leu Asn Val Thr Trp Leu Cys Asn Gly Glu Leu Val Thr
145                 150                 155                 160

Glu Gly Val Ala Glu Ser Leu Phe Leu Pro Arg Thr Asp Tyr Ser Phe
                165                 170                 175

His Lys Phe His Tyr Leu Thr Phe Val Pro Ser Ala Glu Asp Phe Tyr
            180                 185                 190

Asp Cys Arg Val Glu His Trp Gly Leu Asp Gln Pro Leu Leu Lys His
        195                 200                 205

Trp Glu Ala Gln Glu Pro Ile Gln Met Pro Glu Thr Thr Glu Thr Val
    210                 215                 220

Leu Cys Ala Leu Gly Leu Val Leu Gly Leu Val Gly Ile Ile Val Gly
225                 230                 235                 240

Thr Val Leu Ile Ile Lys Ser Leu Arg Ser Gly His Asp Pro Arg Ala
                245                 250                 255

Gln Gly Thr Leu
            260

<210> SEQ ID NO 5
```

-continued

```
<211> LENGTH: 258
<212> TYPE: PRT
<213> ORGANISM: Homo sapiens

<400> SEQUENCE: 5

Met Met Val Leu Gln Val Ser Ala Ala Pro Arg Thr Val Ala Leu Thr
1               5                   10                  15

Ala Leu Leu Met Val Leu Leu Thr Ser Val Val Gln Gly Arg Ala Thr
                20                  25                  30

Pro Glu Asn Tyr Leu Phe Gln Gly Arg Gln Glu Cys Tyr Ala Phe Asn
            35                  40                  45

Gly Thr Gln Arg Phe Leu Glu Arg Tyr Ile Tyr Asn Arg Glu Glu Phe
        50                  55                  60

Ala Arg Phe Asp Ser Asp Val Gly Glu Phe Arg Ala Val Thr Glu Leu
65                  70                  75                  80

Gly Arg Pro Ala Ala Glu Tyr Trp Asn Ser Gln Lys Asp Ile Leu Glu
                85                  90                  95

Glu Lys Arg Ala Val Pro Asp Arg Met Cys Arg His Asn Tyr Glu Leu
            100                 105                 110

Gly Gly Pro Met Thr Leu Gln Arg Arg Val Gln Pro Arg Val Asn Val
        115                 120                 125

Ser Pro Ser Lys Lys Gly Pro Leu Gln His His Asn Leu Leu Val Cys
    130                 135                 140

His Val Thr Asp Phe Tyr Pro Gly Ser Ile Gln Val Arg Trp Phe Leu
145                 150                 155                 160

Asn Gly Gln Glu Glu Thr Ala Gly Val Val Ser Thr Asn Leu Ile Arg
                165                 170                 175

Asn Gly Asp Trp Thr Phe Gln Ile Leu Val Met Leu Glu Met Thr Pro
                180                 185                 190

Gln Gln Gly Asp Val Tyr Thr Cys Gln Val Glu His Thr Ser Leu Asp
            195                 200                 205

Ser Pro Val Thr Val Glu Trp Lys Ala Gln Ser Asp Ser Ala Arg Ser
    210                 215                 220

Lys Thr Leu Thr Gly Ala Gly Gly Phe Val Leu Gly Leu Ile Ile Cys
225                 230                 235                 240

Gly Val Gly Ile Phe Met His Arg Arg Ser Lys Lys Val Gln Arg Gly
                245                 250                 255

Ser Ala

<210> SEQ ID NO 6
<211> LENGTH: 254
<212> TYPE: PRT
<213> ORGANISM: Homo sapiens

<400> SEQUENCE: 6

Met Ile Leu Asn Lys Ala Leu Met Leu Gly Ala Leu Ala Leu Thr Thr
1               5                   10                  15

Val Met Ser Pro Cys Gly Gly Glu Asp Ile Val Ala Asp His Val Ala
                20                  25                  30

Ser Tyr Gly Val Asn Leu Tyr Gln Ser Tyr Gly Pro Ser Gly Gln Tyr
            35                  40                  45

Thr His Glu Phe Asp Gly Asp Glu Gln Phe Tyr Val Asp Leu Gly Arg
        50                  55                  60

Lys Glu Thr Val Trp Cys Leu Pro Val Leu Arg Gln Phe Arg Phe Asp
65                  70                  75                  80
```

-continued

```
Pro Gln Phe Ala Leu Thr Asn Ile Ala Val Leu Lys His Asn Leu Asn
                85                  90                  95

Ser Leu Ile Lys Arg Ser Asn Ser Thr Ala Ala Thr Asn Glu Val Pro
            100                 105                 110

Glu Val Thr Val Phe Ser Lys Ser Pro Val Thr Leu Gly Gln Pro Asn
            115                 120                 125

Ile Leu Ile Cys Leu Val Asp Asn Ile Phe Pro Pro Val Val Asn Ile
    130                 135                 140

Thr Trp Leu Ser Asn Gly His Ser Val Thr Glu Gly Val Ser Glu Thr
145                 150                 155                 160

Ser Phe Leu Ser Lys Ser Asp His Ser Phe Phe Lys Ile Ser Tyr Leu
                165                 170                 175

Thr Leu Leu Pro Ser Ala Glu Glu Ser Tyr Asp Cys Lys Val Glu His
            180                 185                 190

Trp Gly Leu Asp Lys Pro Leu Leu Lys His Trp Glu Pro Glu Ile Pro
            195                 200                 205

Ala Pro Met Ser Glu Leu Thr Glu Thr Val Val Cys Ala Leu Gly Leu
    210                 215                 220

Ser Val Gly Leu Val Gly Ile Val Val Gly Thr Val Phe Ile Ile Arg
225                 230                 235                 240

Gly Leu Arg Ser Val Gly Ala Ser Arg His Gln Gly Pro Leu
                245                 250

<210> SEQ ID NO 7
<211> LENGTH: 261
<212> TYPE: PRT
<213> ORGANISM: Homo sapiens

<400> SEQUENCE: 7

Met Ser Trp Lys Lys Ala Leu Arg Ile Pro Gly Gly Leu Arg Ala Ala
1               5                   10                  15

Thr Val Thr Leu Met Leu Ala Met Leu Ser Thr Pro Val Ala Glu Gly
            20                  25                  30

Arg Asp Ser Pro Glu Asp Phe Val Tyr Gln Phe Lys Ala Met Cys Tyr
            35                  40                  45

Phe Thr Asn Gly Thr Glu Arg Val Arg Tyr Val Thr Arg Tyr Ile Tyr
    50                  55                  60

Asn Arg Glu Glu Tyr Ala Arg Phe Asp Ser Asp Val Glu Val Tyr Arg
65                  70                  75                  80

Ala Val Thr Pro Leu Gly Pro Pro Asp Ala Glu Tyr Trp Asn Ser Gln
                85                  90                  95

Lys Glu Val Leu Glu Arg Thr Arg Ala Glu Leu Asp Thr Val Cys Arg
            100                 105                 110

His Asn Tyr Gln Leu Glu Leu Arg Thr Thr Leu Gln Arg Arg Val Glu
            115                 120                 125

Pro Thr Val Thr Ile Ser Pro Ser Arg Thr Glu Ala Leu Asn His His
    130                 135                 140

Asn Leu Leu Val Cys Ser Val Thr Asp Phe Tyr Pro Ala Gln Ile Lys
145                 150                 155                 160

Val Arg Trp Phe Arg Asn Asp Gln Glu Glu Thr Thr Gly Val Val Ser
                165                 170                 175

Thr Pro Leu Ile Arg Asn Gly Asp Trp Thr Phe Gln Ile Leu Val Met
            180                 185                 190

Leu Glu Met Thr Pro Gln His Gly Asp Val Tyr Thr Cys His Val Glu
            195                 200                 205
```

-continued

```
His Pro Ser Leu Gln Asn Pro Ile Thr Val Glu Trp Arg Ala Gln Ser
    210                 215                 220

Glu Ser Ala Gln Ser Lys Met Leu Ser Gly Ile Gly Gly Phe Val Leu
225                 230                 235                 240

Gly Leu Ile Phe Leu Gly Leu Gly Leu Ile Ile His His Arg Ser Gln
                245                 250                 255

Lys Gly Leu Leu His
            260
```

```
<210> SEQ ID NO 8
<211> LENGTH: 254
<212> TYPE: PRT
<213> ORGANISM: Homo sapiens

<400> SEQUENCE: 8
```

```
Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
            20                  25                  30

Ile Gln Ala Glu Phe Tyr Leu Asn Pro Asp Gln Ser Gly Glu Phe Met
        35                  40                  45

Phe Asp Phe Asp Gly Asp Glu Ile Phe His Val Asp Met Ala Lys Lys
    50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
        115                 120                 125

Val Leu Ile Cys Phe Ile Asp Lys Phe Thr Pro Pro Val Val Asn Val
    130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
        195                 200                 205

Ser Pro Leu Pro Glu Thr Thr Glu Asn Val Val Cys Ala Leu Gly Leu
    210                 215                 220

Thr Val Gly Leu Val Gly Ile Ile Ile Gly Thr Ile Phe Ile Ile Lys
225                 230                 235                 240

Gly Val Arg Lys Ser Asn Ala Ala Glu Arg Arg Gly Pro Leu
                245                 250
```

```
<210> SEQ ID NO 9
<211> LENGTH: 266
<212> TYPE: PRT
<213> ORGANISM: Homo sapiens

<400> SEQUENCE: 9
```

```
Met Val Cys Leu Arg Leu Pro Gly Gly Ser Cys Met Ala Val Leu Thr
1               5                   10                  15
```

-continued

```
Val Thr Leu Met Val Leu Ser Ser Pro Leu Ala Leu Ala Gly Asp Thr
            20                  25                  30

Arg Pro Arg Phe Leu Glu Glu Val Lys Phe Glu Cys His Phe Phe Asn
            35                  40                  45

Gly Thr Glu Arg Val Arg Leu Leu Glu Arg Arg Val His Asn Gln Glu
    50                  55                  60

Glu Tyr Ala Arg Tyr Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
                85                  90                  95

Leu Glu Arg Arg Arg Ala Ala Val Asp Thr Tyr Cys Arg His Asn Tyr
            100                 105                 110

Gly Val Gly Glu Ser Phe Thr Val Gln Arg Arg Val Gln Pro Lys Val
            115                 120                 125

Thr Val Tyr Pro Ser Lys Thr Gln Pro Leu Gln His His Asn Leu Leu
    130                 135                 140

Val Cys Ser Val Asn Gly Phe Tyr Pro Gly Ser Ile Glu Val Arg Trp
145                 150                 155                 160

Phe Arg Asn Gly Gln Glu Glu Lys Thr Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Gln Ser Gly Glu Val Tyr Thr Cys Gln Val Glu His Pro Ser
            195                 200                 205

Val Met Ser Pro Leu Thr Val Glu Trp Arg Ala Arg Ser Glu Ser Ala
    210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Pro Pro Thr Gly Phe Leu Ser
            260                 265
```

```
<210> SEQ ID NO 10
<211> LENGTH: 250
<212> TYPE: PRT
<213> ORGANISM: Mus musculus

<400> SEQUENCE: 10
```

```
Arg Ser Arg Ala Leu Ile Leu Gly Val Leu Ala Leu Thr Thr Met Leu
1               5                   10                  15

Ser Leu Cys Gly Gly Glu Asp Tyr Ile Glu Ala Asp His Val Ala Phe
            20                  25                  30

Tyr Gly Ile Ser Val Tyr Gln Ser Pro Gly Asp Ile Gly Gln Tyr Thr
            35                  40                  45

Phe Glu Phe Asp Gly Asp Glu Leu Phe Tyr Val Asp Leu Asp Lys Lys
    50                  55                  60

Glu Thr Val Trp Met Leu Pro Glu Phe Gly Gln Leu Thr Ser Phe Asp
65                  70                  75                  80

Pro Gln Gly Gly Leu Gln Glu Ile Ala Thr Gly Lys Tyr Asn Leu Glu
                85                  90                  95

Ile Leu Ile Lys Asp Ser Asn Phe Thr Pro Ala Ala Asn Glu Ala Pro
            100                 105                 110

Gln Ala Thr Val Phe Pro Lys Ser Pro Val Leu Leu Gly Gln Pro Asn
```

```
                115                  120                  125

Thr Leu Ile Cys Phe Val Asp Asn Ile Phe Pro Pro Val Ile Asn Ile
    130                  135                  140

Thr Trp Leu Arg Asn Ser Lys Ser Val Thr Asp Gly Val Tyr Glu Thr
145                  150                  155                  160

Ser Phe Leu Val Asn Arg Asp His Ser Phe His Lys Leu Ser Tyr Leu
                165                  170                  175

Thr Phe Ile Pro Ser Asp Asp Asp Ile Tyr Asp Cys Lys Val Glu His
                180                  185                  190

Trp Gly Leu Glu Glu Pro Val Leu Lys His Trp Glu Pro Glu Ile Pro
                195                  200                  205

Ala Pro Met Ser Glu Leu Thr Glu Thr Val Ile Cys Ala Leu Gly Leu
    210                  215                  220

Ser Val Gly Leu Val Gly Ile Val Val Gly Thr Ile Phe Ile Ile Gln
225                  230                  235                  240

Gly Leu Arg Ser Gly Gly Thr Ser Arg His
                245                  250

<210> SEQ ID NO 11
<211> LENGTH: 349
<212> TYPE: PRT
<213> ORGANISM: Mus musculus

<400> SEQUENCE: 11

Met Ala Gln Arg Thr Leu Phe Leu Leu Leu Ala Ala Ala Leu Thr Met
1               5                   10                  15

Ile Glu Thr Arg Ala Gly Pro His Ser Met Arg Tyr Phe Glu Thr Ala
                20                  25                  30

Val Phe Arg Pro Gly Leu Gly Glu Pro Arg Phe Ile Ser Val Gly Tyr
            35                  40                  45

Val Asp Asn Thr Gln Phe Val Ser Phe Asp Ser Asp Ala Glu Asn Pro
    50                  55                  60

Arg Ser Glu Pro Arg Ala Pro Trp Met Glu Gln Glu Gly Pro Glu Tyr
65                  70                  75                  80

Trp Glu Arg Glu Thr Gln Ile Ala Lys Asp Asn Glu Gln Ser Phe Gly
                85                  90                  95

Trp Ser Leu Arg Asn Leu Ile His Tyr Tyr Asn Gln Ser Lys Gly Gly
                100                 105                 110

Phe His Thr Phe Gln Arg Leu Ser Gly Cys Asp Met Gly Leu Asp Gly
    115                 120                 125

Arg Leu Leu Arg Gly Tyr Leu Gln Phe Ala Tyr Asp Gly Arg Asp Tyr
    130                 135                 140

Ile Thr Leu Asn Glu Asp Leu Lys Thr Trp Met Ala Ala Asp Leu Val
145                 150                 155                 160

Ala Leu Ile Thr Arg Arg Lys Trp Glu Gln Ala Gly Ala Ala Glu Leu
                165                 170                 175

Tyr Lys Phe Tyr Leu Glu Gly Glu Cys Val Glu Trp Leu Arg Arg Tyr
                180                 185                 190

Leu Glu Leu Gly Asn Glu Thr Leu Leu Arg Thr Asp Pro Pro Lys Ala
                195                 200                 205

His Val Thr His His Pro Arg Pro Ala Gly Asp Val Thr Leu Arg Cys
    210                 215                 220

Trp Ala Leu Gly Phe Tyr Pro Ala Asp Ile Thr Leu Thr Trp Gln Leu
225                 230                 235                 240
```

-continued

```
Asn Gly Glu Glu Leu Thr Gln Asp Met Glu Leu Val Glu Thr Arg Pro
                245             250             255

Ala Gly Asp Gly Thr Phe Gln Lys Trp Ala Ala Val Val Val Pro Leu
            260             265             270

Gly Lys Glu Gln Asn Tyr Thr Cys His Val Tyr His Glu Gly Leu Pro
        275             280             285

Glu Pro Leu Thr Leu Arg Trp Glu Pro Pro Ser Thr Gly Ser Asn
    290             295             300

Met Val Asn Ile Ala Val Leu Val Val Leu Gly Ala Val Ile Ile Ile
305             310             315             320

Glu Ala Met Val Ala Phe Val Leu Lys Ser Ser Arg Lys Ile Ala Ile
            325             330             335

Leu Pro Gly Pro Ala Gly Thr Lys Gly Ser Ser Ala Ser
            340             345
```

```
<210> SEQ ID NO 12
<211> LENGTH: 350
<212> TYPE: PRT
<213> ORGANISM: Mus musculus

<400> SEQUENCE: 12

Met Ala Pro Cys Thr Leu Leu Leu Leu Leu Ala Ala Ala Leu Ala Pro
1               5                   10                  15

Thr Gln Thr Arg Ala Ala Arg Ala Ala Ala Arg Gly Pro Val Arg Arg
            20                  25                  30

Ser Gly Ser His Arg Ala Pro Pro Pro Gly Pro His Ser Leu Ser Asp
        35                  40                  45

Ala Asp Asn Pro Arg Phe Glu Pro Arg Ala Pro Trp Met Glu Gln Glu
    50                  55                  60

Gly Pro Glu Tyr Trp Glu Glu Gln Thr Gln Arg Ala Lys Ser Asp Glu
65                  70                  75                  80

Gln Trp Phe Arg Val Ser Leu Arg Thr Ala Gln Arg Tyr Tyr Asn Gln
                85                  90                  95

Ser Lys Gly Gly Ser His Thr Phe Gln Arg Met Phe Gly Cys Asp Val
            100                 105                 110

Gly Ser Asp Trp Arg Leu Leu Arg Gly Tyr Gln Gln Phe Ala Tyr Asp
        115                 120                 125

Gly Arg Asp Tyr Ile Ala Leu Asn Glu Asp Leu Lys Thr Trp Thr Ala
    130                 135                 140

Ala Asp Thr Ala Ala Leu Ile Thr Arg Arg Lys Trp Glu Gln Ala Gly
145                 150                 155                 160

Asp Ala Glu Tyr Tyr Arg Ala Tyr Leu Glu Gly Glu Cys Val Glu Trp
                165                 170                 175

Leu Arg Arg Tyr Leu Glu Leu Gly Asn Glu Thr Leu Leu Arg Thr Asp
            180                 185                 190

Ser Pro Lys Ala His Val Thr Tyr His Pro Arg Ser Gln Val Asp Val
        195                 200                 205

Thr Leu Arg Cys Trp Ala Leu Gly Phe Tyr Pro Ala Asp Ile Thr Leu
    210                 215                 220

Thr Trp Gln Leu Asn Gly Glu Asp Leu Thr Gln Asp Met Glu Leu Val
225                 230                 235                 240

Glu Thr Arg Pro Ala Gly Asp Gly Thr Phe Gln Lys Trp Ala Ala Val
                245                 250                 255

Val Val Pro Leu Gly Lys Glu Gln Asn Tyr Thr Cys His Val His His
            260                 265                 270
```

-continued

```
Lys Gly Leu Pro Glu Pro Leu Thr Leu Arg Trp Lys Leu Pro Pro Pro
        275               280               285

Thr Val Ser Asn Thr Val Ile Ile Ala Val Leu Val Val Leu Gly Ala
        290               295               300

Ala Ile Val Thr Gly Ala Val Val Ala Phe Val Met Lys Met Arg Arg
305               310               315               320

Asn Thr Gly Gly Lys Gly Val Asn Tyr Ala Leu Ala Pro Gly Ser Gln
                325               330               335

Thr Ser Asp Leu Ser Leu Pro Asp Gly Lys Val Met Val His
                340               345               350
```

```
<210> SEQ ID NO 13
<211> LENGTH: 264
<212> TYPE: PRT
<213> ORGANISM: Mus musculus

<400> SEQUENCE: 13
```

```
Met Val Trp Leu Pro Arg Val Pro Cys Val Ala Ala Val Ile Leu Leu
1               5               10               15

Leu Thr Val Leu Ser Pro Pro Met Ala Leu Val Arg Asp Ser Arg Pro
                20               25               30

Trp Phe Leu Glu Tyr Cys Lys Ser Glu Cys His Phe Tyr Asn Gly Thr
        35               40               45

Gln Arg Val Arg Leu Leu Glu Arg Tyr Phe Tyr Asn Leu Glu Glu Asn
        50               55               60

Leu Arg Phe Asp Ser Asp Val Gly Glu Phe His Ala Val Thr Glu Leu
65               70               75               80

Gly Arg Pro Asp Ala Glu Asn Trp Asn Ser Gln Pro Glu Phe Leu Glu
                85               90               95

Gln Lys Arg Ala Glu Val Asp Thr Val Cys Arg His Asn Tyr Glu Ile
                100               105               110

Ser Asp Lys Phe Leu Val Arg Arg Arg Val Glu Pro Thr Val Thr Val
                115               120               125

Tyr Pro Thr Lys Thr Gln Pro Leu Glu His His Asn Leu Leu Val Cys
        130               135               140

Ser Val Ser Asp Phe Tyr Pro Gly Asn Ile Glu Val Arg Trp Phe Arg
145               150               155               160

Asn Gly Lys Glu Glu Lys Thr Gly Ile Val Ser Thr Gly Leu Val Arg
                165               170               175

Asn Gly Asp Trp Thr Phe Gln Thr Leu Val Met Leu Glu Thr Val Pro
                180               185               190

Gln Ser Gly Glu Val Tyr Thr Cys Gln Val Glu His Pro Ser Leu Thr
        195               200               205

Asp Pro Val Thr Val Glu Trp Lys Ala Gln Ser Thr Ser Ala Gln Asn
        210               215               220

Lys Met Leu Ser Gly Val Gly Gly Phe Val Leu Gly Leu Leu Phe Leu
225               230               235               240

Gly Ala Gly Leu Phe Ile Tyr Phe Arg Asn Gln Lys Gly Gln Ser Gly
                245               250               255

Leu Gln Pro Thr Gly Leu Leu Ser
                260
```

```
<210> SEQ ID NO 14
<211> LENGTH: 255
<212> TYPE: PRT
```

<213> ORGANISM: Mus musculus

<400> SEQUENCE: 14

```
Met Ala Thr Ile Gly Ala Leu Val Leu Arg Phe Phe Phe Ile Ala Val
1               5                   10                  15

Leu Met Ser Ser Gln Lys Ser Trp Ala Ile Lys Glu Glu His Thr Ile
            20                  25                  30

Ile Gln Ala Glu Phe Tyr Leu Leu Pro Asp Lys Arg Gly Glu Phe Met
        35                  40                  45

Phe Asp Phe Asp Gly Asp Glu Ile Phe His Val Asp Ile Glu Lys Ser
    50                  55                  60

Glu Thr Ile Trp Arg Leu Glu Glu Phe Ala Lys Phe Ala Ser Phe Glu
65                  70                  75                  80

Ala Gln Gly Ala Leu Ala Asn Ile Ala Val Asp Lys Ala Asn Leu Asp
                85                  90                  95

Val Met Lys Glu Arg Ser Asn Asn Thr Pro Asp Ala Asn Val Ala Pro
                100                 105                 110

Glu Val Thr Val Leu Ser Arg Ser Pro Val Asn Leu Gly Glu Pro Asn
            115                 120                 125

Ile Leu Ile Cys Phe Ile Asp Lys Phe Ser Pro Pro Val Val Asn Val
        130                 135                 140

Thr Trp Leu Arg Asn Gly Arg Pro Val Thr Glu Gly Val Ser Glu Thr
145                 150                 155                 160

Val Phe Leu Pro Arg Asp Asp His Leu Phe Arg Lys Phe His Tyr Leu
                165                 170                 175

Thr Phe Leu Pro Ser Thr Asp Asp Phe Tyr Asp Cys Glu Val Asp His
                180                 185                 190

Trp Gly Leu Glu Glu Pro Leu Arg Lys His Trp Glu Phe Glu Glu Lys
            195                 200                 205

Thr Leu Leu Pro Glu Thr Lys Glu Asn Val Val Cys Ala Leu Gly Leu
        210                 215                 220

Phe Val Gly Leu Val Gly Ile Val Val Gly Ile Ile Leu Ile Met Lys
225                 230                 235                 240

Gly Ile Lys Lys Arg Asn Val Val Glu Arg Arg Gln Gly Ala Leu
                245                 250                 255
```

<210> SEQ ID NO 15
<211> LENGTH: 263
<212> TYPE: PRT
<213> ORGANISM: Mus musculus

<400> SEQUENCE: 15

```
Met Trp Leu Pro Arg Val Pro Cys Val Ala Ala Val Ile Leu Leu Leu
1               5                   10                  15

Thr Val Leu Ser Pro Pro Val Ala Leu Val Arg Asp Ser Arg Pro Trp
            20                  25                  30

Phe Leu Glu Tyr Cys Lys Ser Glu Cys His Phe Tyr Asn Gly Thr Gln
        35                  40                  45

Arg Val Arg Leu Leu Val Arg Tyr Phe Tyr Asn Leu Glu Glu Asn Leu
    50                  55                  60

Arg Phe Asp Ser Asp Val Gly Glu Phe Arg Ala Val Thr Glu Leu Gly
65                  70                  75                  80

Arg Pro Asp Ala Glu Asn Trp Asn Ser Gln Pro Glu Phe Leu Glu Gln
                85                  90                  95

Lys Arg Ala Glu Val Asp Thr Val Cys Arg His Asn Tyr Glu Ile Phe
```

-continued

```
               100               105               110

Asp Asn Phe Leu Val Pro Arg Arg Val Glu Pro Thr Val Thr Val Tyr
        115               120               125

Pro Thr Lys Thr Gln Pro Leu Glu His His Asn Leu Leu Val Cys Ser
    130               135               140

Val Ser Asp Phe Tyr Pro Gly Asn Ile Glu Val Arg Trp Phe Arg Asn
145               150               155               160

Gly Lys Glu Glu Lys Thr Gly Ile Val Ser Thr Gly Leu Val Arg Asn
                165               170               175

Gly Asp Trp Thr Phe Gln Thr Leu Val Met Leu Glu Thr Val Pro Gln
            180               185               190

Ser Gly Glu Val Tyr Thr Cys Gln Val Glu His Pro Ser Leu Thr Asp
            195               200               205

Pro Val Thr Val Glu Trp Lys Ala Gln Ser Thr Ser Ala Gln Asn Lys
        210               215               220

Met Leu Ser Gly Val Gly Gly Phe Val Leu Gly Leu Leu Phe Leu Gly
225               230               235               240

Ala Gly Leu Phe Ile Tyr Phe Arg Asn Gln Lys Gly Gln Ser Gly Leu
                245               250               255

Gln Pro Thr Gly Leu Leu Ser
            260

<210> SEQ ID NO 16
<211> LENGTH: 142
<212> TYPE: PRT
<213> ORGANISM: Homo sapiens

<400> SEQUENCE: 16

Pro Asn Ile Gln Asn Pro Asp Pro Ala Val Tyr Gln Leu Arg Asp Ser
1                 5                 10                15

Lys Ser Ser Asp Lys Ser Val Cys Leu Phe Thr Asp Phe Asp Ser Gln
            20                25                30

Thr Asn Val Ser Gln Ser Lys Asp Ser Asp Val Tyr Ile Thr Asp Lys
        35                40                45

Thr Val Leu Asp Met Arg Ser Met Asp Phe Lys Ser Asn Ser Ala Val
    50                55                60

Ala Trp Ser Asn Lys Ser Asp Phe Ala Cys Ala Asn Ala Phe Asn Asn
65                70                75                80

Ser Ile Ile Pro Glu Asp Thr Phe Phe Pro Ser Pro Glu Ser Ser Cys
                85                90                95

Asp Val Lys Leu Val Glu Lys Ser Phe Glu Thr Asp Thr Asn Leu Asn
                100               105               110

Phe Gln Asn Leu Ser Val Ile Gly Phe Arg Ile Leu Leu Leu Lys Val
            115               120               125

Ala Gly Phe Asn Leu Leu Met Thr Leu Arg Leu Trp Ser Ser
        130               135               140

<210> SEQ ID NO 17
<211> LENGTH: 177
<212> TYPE: PRT
<213> ORGANISM: Homo sapiens

<400> SEQUENCE: 17

Glu Asp Leu Asn Lys Val Phe Pro Pro Glu Val Ala Val Phe Glu Pro
1                 5                 10                15

Ser Glu Ala Glu Ile Ser His Thr Gln Lys Ala Thr Leu Val Cys Leu
```

-continued

```
              20              25              30

Ala Thr Gly Phe Phe Pro Asp His Val Glu Leu Ser Trp Trp Val Asn
         35              40              45

Gly Lys Glu Val His Ser Gly Val Ser Thr Asp Pro Gln Pro Leu Lys
     50              55              60

Glu Gln Pro Ala Leu Asn Asp Ser Arg Tyr Cys Leu Ser Ser Arg Leu
65              70              75              80

Arg Val Ser Ala Thr Phe Trp Gln Asn Pro Arg Asn His Phe Arg Cys
             85              90              95

Gln Val Gln Phe Tyr Gly Leu Ser Glu Asn Asp Glu Trp Thr Gln Asp
             100             105             110

Arg Ala Lys Pro Val Thr Gln Ile Val Ser Ala Glu Ala Trp Gly Arg
         115             120             125

Ala Asp Cys Gly Phe Thr Ser Val Ser Tyr Gln Gln Gly Val Leu Ser
         130             135             140

Ala Thr Ile Leu Tyr Glu Ile Leu Leu Gly Lys Ala Thr Leu Tyr Ala
145             150             155             160

Val Leu Val Ser Ala Leu Val Leu Met Ala Met Val Lys Arg Lys Asp
             165             170             175

Phe
```

```
<210> SEQ ID NO 18
<211> LENGTH: 178
<212> TYPE: PRT
<213> ORGANISM: Homo sapiens

<400> SEQUENCE: 18

Asp Leu Lys Asn Val Phe Pro Pro Glu Val Ala Val Phe Glu Pro Ser
1               5               10              15

Glu Ala Glu Ile Ser His Thr Gln Lys Ala Thr Leu Val Cys Leu Ala
             20              25              30

Thr Gly Phe Tyr Pro Asp His Val Glu Leu Ser Trp Trp Val Asn Gly
         35              40              45

Lys Glu Val His Ser Gly Val Ser Thr Asp Pro Gln Pro Leu Lys Glu
     50              55              60

Gln Pro Ala Leu Asn Asp Ser Arg Tyr Cys Leu Ser Ser Arg Leu Arg
65              70              75              80

Val Ser Ala Thr Phe Trp Gln Asn Pro Arg Asn His Phe Arg Cys Gln
             85              90              95

Val Gln Phe Tyr Gly Leu Ser Glu Asn Asp Glu Trp Thr Gln Asp Arg
             100             105             110

Ala Lys Pro Val Thr Gln Ile Val Ser Ala Glu Ala Trp Gly Arg Ala
         115             120             125

Asp Cys Gly Phe Thr Ser Glu Ser Tyr Gln Gln Gly Val Leu Ser Ala
         130             135             140

Thr Ile Leu Tyr Glu Ile Leu Leu Gly Lys Ala Thr Leu Tyr Ala Val
145             150             155             160

Leu Val Ser Ala Leu Val Leu Met Ala Met Val Lys Arg Lys Asp Ser
             165             170             175

Arg Gly
```

```
<210> SEQ ID NO 19
<211> LENGTH: 153
<212> TYPE: PRT
<213> ORGANISM: Homo sapiens
```

<400> SEQUENCE: 19

```
Ser Gln Pro His Thr Lys Pro Ser Val Phe Val Met Lys Asn Gly Thr
1               5                   10                  15

Asn Val Ala Cys Leu Val Lys Glu Phe Tyr Pro Lys Asp Ile Arg Ile
            20                  25                  30

Asn Leu Val Ser Ser Lys Lys Ile Thr Glu Phe Asp Pro Ala Ile Val
        35                  40                  45

Ile Ser Pro Ser Gly Lys Tyr Asn Ala Val Lys Leu Gly Lys Tyr Glu
    50                  55                  60

Asp Ser Asn Ser Val Thr Cys Ser Val Gln His Asp Asn Lys Thr Val
65                  70                  75                  80

His Ser Thr Asp Phe Glu Val Lys Thr Asp Ser Thr Asp His Val Lys
            85                  90                  95

Pro Lys Glu Thr Glu Asn Thr Lys Gln Pro Ser Lys Ser Cys His Lys
            100                 105                 110

Pro Lys Ala Ile Val His Thr Glu Lys Val Asn Met Met Ser Leu Thr
        115                 120                 125

Val Leu Gly Leu Arg Met Leu Phe Ala Lys Thr Val Ala Val Asn Phe
    130                 135                 140

Leu Leu Thr Ala Lys Leu Phe Phe Leu
145                 150
```

<210> SEQ ID NO 20
<211> LENGTH: 173
<212> TYPE: PRT
<213> ORGANISM: Homo sapiens

<400> SEQUENCE: 20

```
Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Val Ile Lys Ile His Trp Gln Glu
        35                  40                  45

Lys Lys Ser Asn Thr Ile Leu Gly Ser Gln Glu Gly Asn Thr Met Lys
    50                  55                  60

Thr Asn Asp Thr Tyr Met Lys Phe Ser Trp Leu Thr Val Pro Glu Lys
65                  70                  75                  80

Ser Leu Asp Lys Glu His Arg Cys Ile Val Arg His Glu Asn Asn Lys
            85                  90                  95

Asn Gly Val Asp Gln Glu Ile Ile Phe Pro Pro Ile Lys Thr Asp Val
            100                 105                 110

Ile Thr Met Asp Pro Lys Asp Asn Cys Ser Lys Asp Ala Asn Asp Thr
        115                 120                 125

Leu Leu Leu Gln Leu Thr Asn Thr Ser Ala Tyr Tyr Met Tyr Leu Leu
    130                 135                 140

Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
            165                 170
```

<210> SEQ ID NO 21
<211> LENGTH: 189
<212> TYPE: PRT
<213> ORGANISM: Homo sapiens -continued

<400> SEQUENCE: 21

```
Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Ile Ile Lys Ile His Trp Gln Glu
        35                  40                  45

Lys Lys Ser Asn Thr Ile Leu Gly Ser Gln Glu Gly Asn Thr Met Lys
    50                  55                  60

Thr Asn Asp Thr Tyr Met Lys Phe Ser Trp Leu Thr Val Pro Glu Glu
65                  70                  75                  80

Ser Leu Asp Lys Glu His Arg Cys Ile Val Arg His Glu Asn Asn Lys
                85                  90                  95

Asn Gly Ile Asp Gln Glu Ile Ile Phe Pro Pro Ile Lys Thr Asp Val
                100                 105                 110

Thr Thr Val Asp Pro Lys Asp Ser Tyr Ser Lys Asp Ala Asn Asp Val
            115                 120                 125

Ile Thr Met Asp Pro Lys Asp Asn Trp Ser Lys Asp Ala Asn Asp Thr
    130                 135                 140

Leu Leu Leu Gln Leu Thr Asn Thr Ser Ala Tyr Tyr Met Tyr Leu Leu
145                 150                 155                 160

Leu Leu Leu Lys Ser Val Val Tyr Phe Ala Ile Ile Thr Cys Cys Leu
                165                 170                 175

Leu Gly Arg Thr Ala Phe Cys Cys Asn Gly Glu Lys Ser
            180                 185
```

```
<210> SEQ ID NO 22
<211> LENGTH: 138
<212> TYPE: PRT
<213> ORGANISM: Mus musculus
```

<400> SEQUENCE: 22

```
Pro Tyr Ile Gln Asn Pro Glu Pro Ala Val Tyr Gln Leu Lys Asp Pro
1               5                   10                  15

Arg Ser Gln Asp Ser Thr Leu Cys Leu Phe Thr Asp Phe Asp Ser Gln
            20                  25                  30

Ile Asn Val Pro Lys Thr Met Glu Ser Gly Thr Phe Ile Thr Asp Lys
        35                  40                  45

Thr Val Leu Asp Met Lys Ala Met Asp Ser Lys Ser Asn Gly Ala Ile
    50                  55                  60

Ala Trp Ser Asn Gln Thr Ser Phe Thr Cys Gln Asp Ile Phe Lys Glu
65                  70                  75                  80

Thr Asn Ala Thr Tyr Pro Ser Ser Asp Val Pro Cys Asp Ala Thr Leu
                85                  90                  95

Thr Glu Lys Ser Phe Glu Thr Asp Met Asn Leu Asn Phe Gln Asn Leu
                100                 105                 110

Ser Val Met Gly Leu Arg Ile Leu Leu Leu Lys Val Ala Gly Phe Asn
            115                 120                 125

Leu Leu Met Thr Leu Arg Leu Trp Ser Ser
    130                 135
```

```
<210> SEQ ID NO 23
<211> LENGTH: 173
<212> TYPE: PRT
<213> ORGANISM: Mus musculus
```

-continued

```
<400> SEQUENCE: 23

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 24
<211> LENGTH: 173
<212> TYPE: PRT
<213> ORGANISM: Mus musculus

<400> SEQUENCE: 24

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
            115                 120                 125

Ile Thr Ser Ala Ser Tyr His Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Lys Asn Ser
                165                 170

<210> SEQ ID NO 25
```

```
<211> LENGTH: 167
<212> TYPE: PRT
<213> ORGANISM: Mus musculus

<400> SEQUENCE: 25

Asp Lys Arg Leu Asp Ala Asp Ile Ser Pro Lys Pro Thr Ile Phe Leu
1               5                   10                  15

Pro Ser Val Ala Glu Thr Asn Leu His Lys Thr Gly Thr Tyr Leu Cys
            20                  25                  30

Leu Leu Glu Lys Phe Phe Pro Asp Val Ile Arg Val Tyr Trp Lys Glu
            35                  40                  45

Lys Asn Gly Asn Thr Ile Leu Asp Ser Gln Glu Gly Asp Thr Leu Lys
        50                  55                  60

Thr Lys Gly Thr Tyr Met Lys Phe Ser Trp Leu Thr Val Pro Glu Arg
65                  70                  75                  80

Ala Met Gly Lys Glu His Ser Cys Ile Val Lys His Glu Asn Asn Lys
                85                  90                  95

Gly Gly Ala Asp Gln Glu Ile Phe Phe Pro Ser Ile Lys Lys Val Ala
            100                 105                 110

Thr Thr Cys Trp Gln Asp Lys Asn Asp Val Leu Gln Phe Gln Phe Thr
            115                 120                 125

Ser Thr Ser Ala Tyr Tyr Thr Tyr Leu Leu Leu Leu Lys Ser Val
        130                 135                 140

Ile Tyr Leu Ala Ile Ile Ser Phe Ser Leu Leu Arg Arg Thr Ser Val
145                 150                 155                 160

Cys Gly Asn Glu Lys Lys Ser
                165

<210> SEQ ID NO 26
<211> LENGTH: 172
<212> TYPE: PRT
<213> ORGANISM: Mus musculus

<400> SEQUENCE: 26

Asp Lys Lys Leu Asp Ala Asp Ile Ser Pro Lys Pro Thr Ile Phe Leu
1               5                   10                  15

Pro Ser Val Ala Glu Thr Asn Leu His Lys Thr Gly Thr Tyr Leu Cys
            20                  25                  30

Val Leu Glu Lys Phe Phe Pro Asp Val Ile Arg Val Tyr Trp Lys Glu
            35                  40                  45

Lys Lys Gly Asn Thr Ile Leu Asp Ser Gln Glu Gly Asp Met Leu Lys
        50                  55                  60

Thr Asn Asp Thr Tyr Met Lys Phe Ser Trp Leu Thr Val Pro Glu Arg
65                  70                  75                  80

Ser Met Gly Lys Glu His Arg Cys Ile Val Lys His Glu Asn Asn Lys
                85                  90                  95

Gly Gly Ala Asp Gln Glu Ile Phe Phe Pro Thr Ile Lys Lys Val Ala
            100                 105                 110

Val Ser Thr Lys Pro Thr Thr Cys Trp Gln Asp Lys Asn Asp Val Leu
            115                 120                 125

Gln Leu Gln Phe Thr Ile Thr Ser Ala Tyr Tyr Thr Tyr Leu Leu Leu
        130                 135                 140

Leu Leu Lys Ser Val Ile Tyr Leu Ala Ile Ile Ser Phe Ser Leu Leu
145                 150                 155                 160

Arg Arg Thr Ser Val Cys Cys Asn Glu Lys Lys Ser
                165                 170
```

-continued

```
<210> SEQ ID NO 27
<211> LENGTH: 169
<212> TYPE: PRT
<213> ORGANISM: Mus musculus

<400> SEQUENCE: 27

Pro Ser Asp Lys Arg Leu Asp Ala Asp Ile Ser Pro Lys Pro Thr Ile
1               5                   10                  15

Phe Leu Pro Ser Val Ala Glu Thr Asn Leu His Lys Thr Gly Thr Tyr
            20                  25                  30

Leu Cys Ile Leu Glu Lys Phe Phe Pro Asp Val Ile Arg Val Tyr Trp
        35                  40                  45

Lys Asp Lys Asn Gly Asn Thr Ile Leu Asp Ser Gln Glu Gly Asp Thr
    50                  55                  60

Leu Lys Thr Lys Gly Thr Tyr Met Lys Phe Ser Trp Leu Thr Val Pro
65                  70                  75                  80

Glu Arg Ser Met Gly Lys Glu His Arg Cys Ile Val Lys His Glu Asn
                85                  90                  95

Asn Lys Gly Gly Ala Asp Gln Glu Ile Phe Phe Pro Ser Ile Lys Lys
            100                 105                 110

Val Ala Thr Thr Cys Trp Gln Asp Lys Asn Asp Val Leu Gln Leu Gln
            115                 120                 125

Phe Met Ser Thr Ser Ala Tyr Tyr Thr Tyr Leu Leu Leu Leu Leu Lys
        130                 135                 140

Ser Val Ile Tyr Leu Ala Ile Ile Ser Phe Ser Leu Leu Arg Arg Thr
145                 150                 155                 160

Ser Val Cys Cys Asn Glu Lys Arg Ser
                165

<210> SEQ ID NO 28
<211> LENGTH: 190
<212> TYPE: PRT
<213> ORGANISM: Mus musculus

<400> SEQUENCE: 28

Asp Lys Arg Thr Asp Ser Asp Phe Ser Pro Lys Pro Thr Ile Phe Leu
1               5                   10                  15

Pro Ser Ala Ala Glu Thr Asn Leu His Lys Ala Gly Thr Tyr Leu Cys
            20                  25                  30

Leu Leu Glu Lys Phe Phe Pro Lys Val Ile Arg Val Tyr Trp Lys Glu
        35                  40                  45

Lys Asp Gly Glu Lys Ile Leu Glu Ser Gln Glu Gly Asn Thr Ile Lys
    50                  55                  60

Thr Asn Asp Arg Tyr Met Lys Phe Ser Trp Leu Thr Val Thr Glu Asp
65                  70                  75                  80

Ser Met Ala Lys Glu His Ser Cys Ile Val Lys His Glu Asn Asn Lys
                85                  90                  95

Arg Gly Val Asp Gln Glu Ile Leu Phe Pro Pro Ile Gly Lys Ala Phe
            100                 105                 110

Thr Thr Ile Asn Val Asn Pro Arg Asp Ser Val Leu Arg His Glu Asn
            115                 120                 125

Val Asn Asn Ala Thr Asp Leu Glu Asp Cys Met Lys Gly Arg Lys Asp
        130                 135                 140

Met Leu Gln Leu Gln Val Thr Thr Thr Tyr Ala Phe Tyr Thr Tyr Leu
145                 150                 155                 160
```

-continued

```
Ile Leu Phe Phe Lys Ser Met Val His Leu Ala Phe Val Val Phe Cys
                165                 170                 175

Leu Phe Arg Arg Ala Ala Met Ser Cys Asp Asp Gln Arg Ser
            180                 185                 190

<210> SEQ ID NO 29
<211> LENGTH: 16
<212> TYPE: PRT
<213> ORGANISM: Mus musculus

<400> SEQUENCE: 29

Ala Asn Glu Arg Ala Asp Leu Ile Ala Tyr Leu Lys Gln Ala Thr Lys
1               5                   10                  15

<210> SEQ ID NO 30
<211> LENGTH: 247
<212> TYPE: PRT
<213> ORGANISM: Mus musculus

<400> SEQUENCE: 30

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Lys Pro Gln Ala Pro
                20                  25                  30

Glu Leu Arg Ile Phe Pro Lys Lys Met Asp Ala Glu Leu Gly Gln Lys
            35                  40                  45

Val Asp Leu Val Cys Glu Val Leu Gly Ser Val Ser Gln Gly Cys Ser
        50                  55                  60

Trp Leu Phe Gln Asn Ser Ser Ser Lys Leu Pro Gln Pro Thr Phe Val
65                  70                  75                  80

Val Tyr Met Ala Ser Ser His Asn Lys Ile Thr Trp Asp Glu Lys Leu
                85                  90                  95

Asn Ser Ser Lys Leu Phe Ser Ala Met Arg Asp Thr Asn Asn Lys Tyr
                100                 105                 110

Val Leu Thr Leu Asn Lys Phe Ser Lys Glu Asn Glu Gly Tyr Tyr Phe
            115                 120                 125

Cys Ser Val Ile Ser Asn Ser Val Met Tyr Phe Ser Ser Val Val Pro
        130                 135                 140

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
                165                 170                 175

Asp Cys Arg Pro Arg Gly Ser Val Lys Gly Thr Gly Leu Asp Phe Ala
            180                 185                 190

Cys Asp Ile Tyr Ile Trp Ala Pro Leu Ala Gly Ile Cys Val Ala Leu
            195                 200                 205

Leu Leu Ser Leu Ile Ile Thr Leu Ile Cys Tyr His Arg Ser Arg Lys
        210                 215                 220

Arg Val Cys Lys Cys Pro Arg Pro Leu Val Arg Gln Glu Gly Lys Pro
225                 230                 235                 240

Arg Pro Ser Glu Lys Ile Val
                245

<210> SEQ ID NO 31
<211> LENGTH: 213
<212> TYPE: PRT
<213> ORGANISM: Mus musculus
```

-continued

<400> SEQUENCE: 31

```
Met Gln Pro Trp Leu Trp Leu Val Phe Ser Met Lys Leu Ala Ala Leu
1               5                   10                  15

Trp Ser Ser Ser Ala Leu Ile Gln Thr Pro Ser Ser Leu Leu Val Gln
            20                  25                  30

Thr Asn His Thr Ala Lys Met Ser Cys Glu Val Lys Ser Ile Ser Lys
        35                  40                  45

Leu Thr Ser Ile Tyr Trp Leu Arg Glu Arg Gln Asp Pro Lys Asp Lys
        50                  55                  60

Tyr Phe Glu Phe Leu Ala Ser Trp Ser Ser Ser Lys Gly Val Leu Tyr
65                  70                  75                  80

Gly Glu Ser Val Asp Lys Lys Arg Asn Ile Ile Leu Glu Ser Ser Asp
                85                  90                  95

Ser Arg Arg Pro Phe Leu Ser Ile Met Asn Val Lys Pro Glu Asp Ser
                100                 105                 110

Asp Phe Tyr Phe Cys Ala Thr Val Gly Ser Pro Lys Met Val Phe Gly
                115                 120                 125

Thr Gly Thr Lys Leu Thr Val Val Asp Val Leu Pro Thr Thr Ala Pro
        130                 135                 140

Thr Lys Lys Thr Thr Leu Lys Met Lys Lys Lys Gln Cys Pro Phe
145                 150                 155                 160

Pro His Pro Glu Thr Gln Lys Gly Leu Thr Cys Ser Leu Thr Thr Leu
                165                 170                 175

Ser Leu Leu Val Val Cys Ile Leu Leu Leu Leu Ala Phe Leu Gly Val
        180                 185                 190

Ala Val Tyr Phe Tyr Cys Val Arg Arg Arg Ala Arg Ile His Phe Met
        195                 200                 205

Lys Gln Phe His Lys
        210
```

<210> SEQ ID NO 32
<211> LENGTH: 244
<212> TYPE: PRT
<213> ORGANISM: Artificial Sequence
<220> FEATURE:
<223> OTHER INFORMATION: Surrogate Co-Receptor (SCoR) with the CD8 Ig
      domain replaced with the H57 heavy chain

<400> SEQUENCE: 32

```
Met Gln Arg Asn Leu Gly Ala Val Leu Gly Ile Leu Trp Val Gln Ile
1               5                   10                  15

Cys Trp Val Arg Gly Thr Ser Glu Val Tyr Leu Val Glu Ser Gly Gly
            20                  25                  30

Asp Leu Val Gln Pro Gly Ser Ser Leu Lys Val Ser Cys Ala Ala Ser
        35                  40                  45

Gly Phe Thr Phe Ser Asp Phe Trp Met Tyr Trp Val Arg Gln Ala Pro
        50                  55                  60

Gly Lys Gly Leu Glu Trp Val Gly Arg Ile Lys Asn Ile Pro Asn Asn
65                  70                  75                  80

Tyr Ala Thr Glu Tyr Ala Asp Ser Val Arg Gly Arg Phe Thr Ile Ser
                85                  90                  95

Arg Asp Asp Ser Arg Asn Ser Ile Tyr Leu Gln Met Asn Arg Leu Arg
                100                 105                 110

Val Asp Asp Thr Ala Ile Tyr Tyr Cys Thr Arg Ala Gly Arg Phe Asp
        115                 120                 125
```

-continued

```
His Phe Asp Tyr Trp Gly Gln Gly Thr Met Val Thr Val Ser Gly Thr
    130             135             140

Lys Val Asn Ser Thr Thr Thr Lys Pro Val Leu Arg Thr Pro Ser Pro
145             150             155             160

Val His Pro Thr Gly Thr Ser Gln Pro Gln Arg Pro Glu Asp Cys Arg
                165             170             175

Pro Arg Gly Ser Val Lys Gly Thr Gly Leu Asp Phe Ala Cys Asp Ile
            180             185             190

Tyr Ile Trp Ala Pro Leu Ala Gly Ile Cys Val Ala Pro Leu Leu Ser
        195             200             205

Leu Ile Ile Thr Leu Ile Cys Tyr His Arg Ser Arg Lys Arg Val Cys
    210             215             220

Lys Cys Pro Arg Pro Leu Val Arg Gln Glu Gly Lys Pro Arg Pro Ser
225             230             235             240

Glu Lys Ile Val
```

<210> SEQ ID NO 33
<211> LENGTH: 220
<212> TYPE: PRT
<213> ORGANISM: Artificial Sequence
<220> FEATURE:
<223> OTHER INFORMATION: Surrogate Co-Receptor (SCoR) with the CD8 Ig
      domain replaced with the H57 light chain

<400> SEQUENCE: 33

```
Met Ala Thr Arg Leu Leu Cys Tyr Thr Val Leu Cys Leu Leu Gly Ala
1               5               10              15

Arg Ile Leu Asn Ser Lys Tyr Pro Tyr Asp Val Pro Asp Tyr Ala Gly
            20              25              30

Gly Ser Tyr Glu Leu Ile Gln Pro Ser Ser Ala Ser Val Thr Val Gly
        35              40              45

Glu Thr Val Lys Ile Thr Cys Ser Gly Asp Gln Leu Pro Lys Asn Phe
    50              55              60

Ala Tyr Trp Phe Gln Gln Lys Ser Asp Lys Asn Ile Leu Leu Leu Ile
65              70              75              80

Tyr Met Asp Asn Lys Arg Pro Ser Gly Ile Pro Glu Arg Phe Ser Gly
            85              90              95

Ser Thr Ser Gly Thr Thr Ala Thr Leu Thr Ile Ser Gly Ala Gln Pro
            100             105             110

Glu Asp Glu Ala Ala Tyr Tyr Cys Leu Ser Ser Tyr Gly Asp Asn Asn
        115             120             125

Asp Leu Val Phe Gly Ser Gly Thr Gln Leu Thr Val Leu Ser Gly Asp
    130             135             140

Val Leu Pro Thr Thr Ala Pro Thr Lys Lys Thr Thr Leu Lys Met Lys
145             150             155             160

Lys Lys Lys Gln Cys Pro Phe Pro His Pro Glu Thr Gln Lys Gly Leu
                165             170             175

Thr Cys Ser Leu Thr Thr Leu Ser Leu Leu Val Val Cys Ile Leu Leu
            180             185             190

Leu Leu Ala Phe Leu Gly Val Ala Val Tyr Phe Tyr Cys Val Arg Arg
        195             200             205

Arg Ala Arg Ile His Phe Met Lys Gln Phe His Lys
    210             215             220
```

<210> SEQ ID NO 34

<211> LENGTH: 220
<212> TYPE: PRT
<213> ORGANISM: Artificial Sequence
<220> FEATURE:
<223> OTHER INFORMATION: Surrogate Co-Receptor with the CD8 Ig domain
      replaced with the H57 light chain, where the light chain comprises
      an F32A mutation

<400> SEQUENCE: 34

Met Ala Thr Arg Leu Leu Cys Tyr Thr Val Leu Cys Leu Leu Gly Ala
1               5                   10                  15

Arg Ile Leu Asn Ser Lys Tyr Pro Tyr Asp Val Pro Asp Tyr Ala Gly
            20                  25                  30

Gly Ser Tyr Glu Leu Ile Gln Pro Ser Ser Ala Ser Val Thr Val Gly
        35                  40                  45

Glu Thr Val Lys Ile Thr Cys Ser Gly Asp Gln Leu Pro Lys Asn Ala
    50                  55                  60

Ala Tyr Trp Phe Gln Gln Lys Ser Asp Lys Asn Ile Leu Leu Leu Ile
65                  70                  75                  80

Tyr Met Asp Asn Lys Arg Pro Ser Gly Ile Pro Glu Arg Phe Ser Gly
                85                  90                  95

Ser Thr Ser Gly Thr Thr Ala Thr Leu Thr Ile Ser Gly Ala Gln Pro
            100                 105                 110

Glu Asp Glu Ala Ala Tyr Tyr Cys Leu Ser Ser Tyr Gly Asp Asn Asn
        115                 120                 125

Asp Leu Val Phe Gly Ser Gly Thr Gln Leu Thr Val Leu Ser Gly Asp
    130                 135                 140

Val Leu Pro Thr Thr Ala Pro Thr Lys Lys Thr Thr Leu Lys Met Lys
145                 150                 155                 160

Lys Lys Lys Gln Cys Pro Phe Pro His Pro Glu Thr Gln Lys Gly Leu
                165                 170                 175

Thr Cys Ser Leu Thr Thr Leu Ser Leu Leu Val Val Cys Ile Leu Leu
            180                 185                 190

Leu Leu Ala Phe Leu Gly Val Ala Val Tyr Phe Tyr Cys Val Arg Arg
        195                 200                 205

Arg Ala Arg Ile His Phe Met Lys Gln Phe His Lys
    210                 215                 220

<210> SEQ ID NO 35
<211> LENGTH: 220
<212> TYPE: PRT
<213> ORGANISM: Artificial Sequence
<220> FEATURE:
<223> OTHER INFORMATION: Surrogate Co-Receptor (SCoR) with the CD8 Ig
      domain replaced with the H57 light chain, where the light chain
      comprises an L28A mutation

<400> SEQUENCE: 35

Met Ala Thr Arg Leu Leu Cys Tyr Thr Val Leu Cys Leu Leu Gly Ala
1               5                   10                  15

Arg Ile Leu Asn Ser Lys Tyr Pro Tyr Asp Val Pro Asp Tyr Ala Gly
            20                  25                  30

Gly Ser Tyr Glu Leu Ile Gln Pro Ser Ser Ala Ser Val Thr Val Gly
        35                  40                  45

Glu Thr Val Lys Ile Thr Cys Ser Gly Asp Gln Ala Pro Lys Asn Phe
    50                  55                  60

Ala Tyr Trp Phe Gln Gln Lys Ser Asp Lys Asn Ile Leu Leu Leu Ile
65                  70                  75                  80

-continued

```
Tyr Met Asp Asn Lys Arg Pro Ser Gly Ile Pro Glu Arg Phe Ser Gly
                85              90              95

Ser Thr Ser Gly Thr Thr Ala Thr Leu Thr Ile Ser Gly Ala Gln Pro
            100             105             110

Glu Asp Glu Ala Ala Tyr Tyr Cys Leu Ser Ser Tyr Gly Asp Asn Asn
            115             120             125

Asp Leu Val Phe Gly Ser Gly Thr Gln Leu Thr Val Leu Ser Gly Asp
    130             135             140

Val Leu Pro Thr Thr Ala Pro Thr Lys Lys Thr Thr Leu Lys Met Lys
145             150             155             160

Lys Lys Lys Gln Cys Pro Phe Pro His Pro Glu Thr Gln Lys Gly Leu
            165             170             175

Thr Cys Ser Leu Thr Thr Leu Ser Leu Leu Val Val Cys Ile Leu Leu
            180             185             190

Leu Leu Ala Phe Leu Gly Val Ala Val Tyr Phe Tyr Cys Val Arg Arg
            195             200             205

Arg Ala Arg Ile His Phe Met Lys Gln Phe His Lys
    210             215             220
```

<210> SEQ ID NO 36
<211> LENGTH: 220
<212> TYPE: PRT
<213> ORGANISM: Artificial Sequence
<220> FEATURE:
<223> OTHER INFORMATION: Surrogate Co-Receptor with the CD8 Ig domain
      replaced with the H57 light chain, where the light chain comprises
      a Y34A mutation

<400> SEQUENCE: 36

```
Met Ala Thr Arg Leu Leu Cys Tyr Thr Val Leu Cys Leu Leu Gly Ala
1               5               10              15

Arg Ile Leu Asn Ser Lys Tyr Pro Tyr Asp Val Pro Asp Tyr Ala Gly
                20              25              30

Gly Ser Tyr Glu Leu Ile Gln Pro Ser Ser Ala Ser Val Thr Val Gly
            35              40              45

Glu Thr Val Lys Ile Thr Cys Ser Gly Asp Gln Leu Pro Lys Asn Phe
    50              55              60

Ala Ala Trp Phe Gln Gln Lys Ser Asp Lys Asn Ile Leu Leu Leu Ile
65              70              75              80

Tyr Met Asp Asn Lys Arg Pro Ser Gly Ile Pro Glu Arg Phe Ser Gly
                85              90              95

Ser Thr Ser Gly Thr Thr Ala Thr Leu Thr Ile Ser Gly Ala Gln Pro
            100             105             110

Glu Asp Glu Ala Ala Tyr Tyr Cys Leu Ser Ser Tyr Gly Asp Asn Asn
            115             120             125

Asp Leu Val Phe Gly Ser Gly Thr Gln Leu Thr Val Leu Ser Gly Asp
    130             135             140

Val Leu Pro Thr Thr Ala Pro Thr Lys Lys Thr Thr Leu Lys Met Lys
145             150             155             160

Lys Lys Lys Gln Cys Pro Phe Pro His Pro Glu Thr Gln Lys Gly Leu
            165             170             175

Thr Cys Ser Leu Thr Thr Leu Ser Leu Leu Val Val Cys Ile Leu Leu
            180             185             190

Leu Leu Ala Phe Leu Gly Val Ala Val Tyr Phe Tyr Cys Val Arg Arg
            195             200             205

Arg Ala Arg Ile His Phe Met Lys Gln Phe His Lys
```

-continued

```
                210              215              220
```

<210> SEQ ID NO 37
<211> LENGTH: 220
<212> TYPE: PRT
<213> ORGANISM: Artificial Sequence
<220> FEATURE:
<223> OTHER INFORMATION: Surrogate Co-Receptor SCoR with the CD8 Ig
      domain replaced with the H57 heavy chain, where the heavy chain
      comprises a W33A mutation

<400> SEQUENCE: 37

```
Met Ala Thr Arg Leu Leu Cys Tyr Thr Val Leu Cys Leu Leu Gly Ala
1               5                   10                  15

Arg Ile Leu Asn Ser Lys Tyr Pro Tyr Asp Val Pro Asp Tyr Ala Gly
            20                  25                  30

Gly Ser Tyr Glu Leu Ile Gln Pro Ser Ser Ala Ser Val Thr Val Gly
            35                  40                  45

Glu Thr Val Lys Ile Thr Cys Ser Gly Asp Gln Leu Pro Lys Asn Phe
        50                  55                  60

Ala Tyr Ala Phe Gln Gln Lys Ser Asp Lys Asn Ile Leu Leu Leu Ile
65                  70                  75                  80

Tyr Met Asp Asn Lys Arg Pro Ser Gly Ile Pro Glu Arg Phe Ser Gly
                85                  90                  95

Ser Thr Ser Gly Thr Thr Ala Thr Leu Thr Ile Ser Gly Ala Gln Pro
                100                 105                 110

Glu Asp Glu Ala Ala Tyr Tyr Cys Leu Ser Ser Tyr Gly Asp Asn Asn
            115                 120                 125

Asp Leu Val Phe Gly Ser Gly Thr Gln Leu Thr Val Leu Ser Gly Asp
        130                 135                 140

Val Leu Pro Thr Thr Ala Pro Thr Lys Lys Thr Thr Leu Lys Met Lys
145                 150                 155                 160

Lys Lys Lys Gln Cys Pro Phe Pro His Pro Glu Thr Gln Lys Gly Leu
                165                 170                 175

Thr Cys Ser Leu Thr Thr Leu Ser Leu Leu Val Val Cys Ile Leu Leu
                180                 185                 190

Leu Leu Ala Phe Leu Gly Val Ala Val Tyr Phe Tyr Cys Val Arg Arg
            195                 200                 205

Arg Ala Arg Ile His Phe Met Lys Gln Phe His Lys
        210                 215                 220
```

<210> SEQ ID NO 38
<211> LENGTH: 220
<212> TYPE: PRT
<213> ORGANISM: Artificial Sequence
<220> FEATURE:
<223> OTHER INFORMATION: Surrogate Co-Receptor (SCoR) with the CD8 Ig
      domain replaced with the H57 light chain where the light chain
      comprises a F32V mutation

<400> SEQUENCE: 38

```
Met Ala Thr Arg Leu Leu Cys Tyr Thr Val Leu Cys Leu Leu Gly Ala
1               5                   10                  15

Arg Ile Leu Asn Ser Lys Tyr Pro Tyr Asp Val Pro Asp Tyr Ala Gly
            20                  25                  30

Gly Ser Tyr Glu Leu Ile Gln Pro Ser Ser Ala Ser Val Thr Val Gly
            35                  40                  45

Glu Thr Val Lys Ile Thr Cys Ser Gly Asp Gln Leu Pro Lys Asn Val
        50                  55                  60
```

-continued

```
Ala Tyr Trp Phe Gln Gln Lys Ser Asp Lys Asn Ile Leu Leu Leu Ile
65                  70              75                  80

Tyr Met Asp Asn Lys Arg Pro Ser Gly Ile Pro Glu Arg Phe Ser Gly
                85                  90                  95

Ser Thr Ser Gly Thr Thr Ala Thr Leu Thr Ile Ser Gly Ala Gln Pro
            100                 105                 110

Glu Asp Glu Ala Ala Tyr Tyr Cys Leu Ser Ser Tyr Gly Asp Asn Asn
            115                 120                 125

Asp Leu Val Phe Gly Ser Gly Thr Gln Leu Thr Val Leu Ser Gly Asp
        130                 135                 140

Val Leu Pro Thr Thr Ala Pro Thr Lys Lys Thr Thr Leu Lys Met Lys
145                 150                 155                 160

Lys Lys Lys Gln Cys Pro Phe Pro His Pro Glu Thr Gln Lys Gly Leu
                165                 170                 175

Thr Cys Ser Leu Thr Thr Leu Ser Leu Leu Val Val Cys Ile Leu Leu
            180                 185                 190

Leu Leu Ala Phe Leu Gly Val Ala Val Tyr Phe Tyr Cys Val Arg Arg
            195                 200                 205

Arg Ala Arg Ile His Phe Met Lys Gln Phe His Lys
        210                 215                 220
```

<210> SEQ ID NO 39
<211> LENGTH: 220
<212> TYPE: PRT
<213> ORGANISM: Artificial Sequence
<220> FEATURE:
<223> OTHER INFORMATION: Surrogate Co-Receptor (SCoR) with the CD8 Ig
      domain replaced with the H57 light chain, where the light chain
      comprises a F32L mutation

<400> SEQUENCE: 39

```
Met Ala Thr Arg Leu Leu Cys Tyr Thr Val Leu Cys Leu Leu Gly Ala
1               5                   10                  15

Arg Ile Leu Asn Ser Lys Tyr Pro Tyr Asp Val Pro Asp Tyr Ala Gly
                20                  25                  30

Gly Ser Tyr Glu Leu Ile Gln Pro Ser Ser Ala Ser Val Thr Val Gly
            35                  40                  45

Glu Thr Val Lys Ile Thr Cys Ser Gly Asp Gln Leu Pro Lys Asn Leu
        50                  55                  60

Ala Tyr Trp Phe Gln Gln Lys Ser Asp Lys Asn Ile Leu Leu Leu Ile
65                  70              75                  80

Tyr Met Asp Asn Lys Arg Pro Ser Gly Ile Pro Glu Arg Phe Ser Gly
                85                  90                  95

Ser Thr Ser Gly Thr Thr Ala Thr Leu Thr Ile Ser Gly Ala Gln Pro
            100                 105                 110

Glu Asp Glu Ala Ala Tyr Tyr Cys Leu Ser Ser Tyr Gly Asp Asn Asn
            115                 120                 125

Asp Leu Val Phe Gly Ser Gly Thr Gln Leu Thr Val Leu Ser Gly Asp
        130                 135                 140

Val Leu Pro Thr Thr Ala Pro Thr Lys Lys Thr Thr Leu Lys Met Lys
145                 150                 155                 160

Lys Lys Lys Gln Cys Pro Phe Pro His Pro Glu Thr Gln Lys Gly Leu
                165                 170                 175

Thr Cys Ser Leu Thr Thr Leu Ser Leu Leu Val Val Cys Ile Leu Leu
            180                 185                 190
```

-continued

```
Leu Leu Ala Phe Leu Gly Val Ala Val Tyr Phe Tyr Cys Val Arg Arg
        195             200             205

Arg Ala Arg Ile His Phe Met Lys Gln Phe His Lys
        210             215             220

<210> SEQ ID NO 40
<211> LENGTH: 228
<212> TYPE: PRT
<213> ORGANISM: Artificial Sequence
<220> FEATURE:
<223> OTHER INFORMATION: Surrogate Co-Recptor (SCoR) with the CD8beta Ig
      domain replaced with the 2C11 heavy chain

<400> SEQUENCE: 40

Met Ala Thr Arg Leu Leu Cys Tyr Thr Val Leu Cys Leu Leu Gly Ala
1               5               10              15

Arg Ile Leu Asn Ser Lys Tyr Pro Tyr Asp Val Pro Asp Tyr Ala Gly
        20              25              30

Gly Ser Glu Val Gln Leu Val Glu Ser Gly Gly Gly Leu Val Gln Pro
        35              40              45

Gly Lys Ser Leu Lys Leu Ser Cys Glu Ala Ser Gly Phe Thr Phe Ser
    50              55              60

Gly Tyr Gly Met His Trp Val Arg Gln Ala Pro Gly Arg Gly Leu Glu
65              70              75              80

Ser Val Ala Tyr Ile Thr Ser Ser Ser Ile Asn Ile Lys Tyr Ala Asp
                85              90              95

Ala Val Lys Gly Arg Phe Thr Val Ser Arg Asp Asn Ala Lys Asn Leu
        100             105             110

Leu Phe Leu Gln Met Asn Ile Leu Lys Ser Glu Asp Thr Ala Met Tyr
        115             120             125

Tyr Cys Ala Arg Phe Asp Trp Asp Lys Asn Tyr Trp Gly Gln Gly Thr
        130             135             140

Met Val Thr Val Ser Ser Gly Asp Val Leu Pro Thr Thr Ala Pro Thr
145             150             155             160

Lys Lys Thr Thr Leu Lys Met Lys Lys Lys Gln Cys Pro Phe Pro
        165             170             175

His Pro Glu Thr Gln Lys Gly Leu Thr Cys Ser Leu Thr Thr Leu Ser
        180             185             190

Leu Leu Val Val Cys Ile Leu Leu Leu Ala Phe Leu Gly Val Ala
        195             200             205

Val Tyr Phe Tyr Cys Val Arg Arg Arg Ala Arg Ile His Phe Met Lys
        210             215             220

Gln Phe His Lys
225

<210> SEQ ID NO 41
<211> LENGTH: 232
<212> TYPE: PRT
<213> ORGANISM: Artificial Sequence
<220> FEATURE:
<223> OTHER INFORMATION: urrogate Co-Receptor (SCoR) with the CD8alpha
      Ig domain replaced with the 2C11 light chain

<400> SEQUENCE: 41

Met Gln Arg Asn Leu Gly Ala Val Leu Gly Ile Leu Trp Val Gln Ile
1               5               10              15

Cys Trp Val Arg Gly Thr Ser Asp Ile Gln Met Thr Gln Ser Pro Ser
        20              25              30
```

-continued

```
Ser Leu Pro Ala Ser Leu Gly Asp Arg Val Thr Ile Asn Cys Gln Ala
        35                  40                  45

Ser Gln Asp Ile Ser Asn Tyr Leu Asn Trp Tyr Gln Gln Lys Pro Gly
    50                  55                  60

Lys Ala Pro Lys Leu Leu Ile Tyr Tyr Thr Asn Lys Leu Ala Asp Gly
65              70                  75                  80

Val Pro Ser Arg Phe Ser Gly Ser Gly Ser Gly Arg Asp Ser Ser Phe
                85                  90                  95

Thr Ile Ser Ser Leu Glu Ser Glu Asp Ile Gly Ser Tyr Tyr Cys Gln
            100                 105                 110

Gln Tyr Tyr Asn Tyr Pro Trp Thr Phe Gly Pro Gly Thr Lys Leu Glu
        115                 120                 125

Ile Lys Gly Thr Lys Val Asn Ser Thr Thr Thr Lys Pro Val Leu Arg
    130                 135                 140

Thr Pro Ser Pro Val His Pro Thr Gly Thr Ser Gln Pro Gln Arg Pro
145                 150                 155                 160

Glu Asp Cys Arg Pro Arg Gly Ser Val Lys Gly Thr Gly Leu Asp Phe
                165                 170                 175

Ala Cys Asp Ile Tyr Ile Trp Ala Pro Leu Ala Gly Ile Cys Val Ala
            180                 185                 190

Pro Leu Leu Ser Leu Ile Ile Thr Leu Ile Cys Tyr His Arg Ser Arg
        195                 200                 205

Lys Arg Val Cys Lys Cys Pro Arg Pro Leu Val Arg Gln Glu Gly Lys
    210                 215                 220

Pro Arg Pro Ser Glu Lys Ile Val
225                 230

<210> SEQ ID NO 42
<211> LENGTH: 196
<212> TYPE: PRT
<213> ORGANISM: Artificial Sequence
<220> FEATURE:
<223> OTHER INFORMATION: Surrogate Co-Receptor (SCoR) with the CD8 Ig
      domain replaced with the 2C11 light chain with W135A mutation

<400> SEQUENCE: 42

Gly Ser Glu Val Gln Leu Val Glu Ser Gly Gly Gly Leu Val Gln Pro
1               5                   10                  15

Gly Lys Ser Leu Lys Leu Ser Cys Glu Ala Ser Gly Phe Thr Phe Ser
        20                  25                  30

Gly Tyr Gly Met His Trp Val Arg Gln Ala Pro Gly Arg Gly Leu Glu
        35                  40                  45

Ser Val Ala Tyr Ile Thr Ser Ser Ser Ile Asn Ile Lys Tyr Ala Asp
    50                  55                  60

Ala Val Lys Gly Arg Phe Thr Val Ser Arg Asp Asn Ala Lys Asn Leu
65              70                  75                  80

Leu Phe Leu Gln Met Asn Ile Leu Lys Ser Glu Asp Thr Ala Met Tyr
                85                  90                  95

Tyr Cys Ala Arg Phe Asp Ala Asp Lys Asn Tyr Trp Gly Gln Gly Thr
            100                 105                 110

Met Val Thr Val Ser Ser Gly Asp Val Leu Pro Thr Thr Ala Pro Thr
        115                 120                 125

Lys Lys Thr Thr Leu Lys Met Lys Lys Lys Gln Cys Pro Phe Pro
        130                 135                 140

His Pro Glu Thr Gln Lys Gly Leu Thr Cys Ser Leu Thr Thr Leu Ser
145                 150                 155                 160
```

-continued

```
Leu Leu Val Val Cys Ile Leu Leu Leu Ala Phe Leu Gly Val Ala
                165                 170                 175

Val Tyr Phe Tyr Cys Val Arg Arg Arg Ala Arg Ile His Phe Met Lys
            180                 185                 190

Gln Phe His Lys
        195

<210> SEQ ID NO 43
<211> LENGTH: 457
<212> TYPE: PRT
<213> ORGANISM: Mus musculus

<400> SEQUENCE: 43

Met Cys Arg Ala Ile Ser Leu Arg Arg Leu Leu Leu Leu Leu Gln
1               5                   10                  15

Leu Ser Gln Leu Leu Ala Val Thr Gln Gly Lys Thr Leu Val Leu Gly
            20                  25                  30

Lys Glu Gly Glu Ser Ala Glu Leu Pro Cys Glu Ser Ser Gln Lys Lys
        35                  40                  45

Ile Thr Val Phe Thr Trp Lys Phe Ser Asp Gln Arg Lys Ile Leu Gly
        50                  55                  60

Gln His Gly Lys Gly Val Leu Ile Arg Gly Gly Ser Pro Ser Gln Phe
65                  70                  75                  80

Asp Arg Phe Asp Ser Lys Lys Gly Ala Trp Glu Lys Gly Ser Phe Pro
                85                  90                  95

Leu Ile Ile Asn Lys Leu Lys Met Glu Asp Ser Gln Thr Tyr Ile Cys
                100                 105                 110

Glu Leu Glu Asn Arg Lys Glu Glu Val Glu Leu Trp Val Phe Lys Val
            115                 120                 125

Thr Phe Ser Pro Gly Thr Ser Leu Leu Gln Gly Gln Ser Leu Thr Leu
        130                 135                 140

Thr Leu Asp Ser Asn Ser Lys Val Ser Asn Pro Leu Thr Glu Cys Lys
145                 150                 155                 160

His Lys Lys Gly Lys Val Val Ser Gly Ser Lys Val Leu Ser Met Ser
                165                 170                 175

Asn Leu Arg Val Gln Asp Ser Asp Phe Trp Asn Cys Thr Val Thr Leu
            180                 185                 190

Asp Gln Lys Lys Asn Trp Phe Gly Met Thr Leu Ser Val Leu Gly Phe
        195                 200                 205

Gln Ser Thr Ala Ile Thr Ala Tyr Lys Ser Glu Gly Glu Ser Ala Glu
    210                 215                 220

Phe Ser Phe Pro Leu Asn Phe Ala Glu Glu Asn Gly Trp Gly Glu Leu
225                 230                 235                 240

Met Trp Lys Ala Glu Lys Asp Ser Phe Phe Gln Pro Trp Ile Ser Phe
                245                 250                 255

Ser Ile Lys Asn Lys Glu Val Ser Val Gln Lys Ser Thr Lys Asp Leu
                260                 265                 270

Lys Leu Gln Leu Lys Glu Thr Leu Pro Leu Thr Leu Lys Ile Pro Gln
            275                 280                 285

Val Ser Leu Gln Phe Ala Gly Ser Gly Asn Leu Thr Leu Thr Leu Asp
    290                 295                 300

Lys Gly Thr Leu His Gln Glu Val Asn Leu Val Val Met Lys Val Ala
305                 310                 315                 320

Gln Leu Asn Asn Thr Leu Thr Cys Glu Val Met Gly Pro Thr Ser Pro
```

-continued
_____

```
                325                 330                 335

Lys Met Arg Leu Thr Leu Lys Gln Glu Asn Gln Glu Ala Arg Val Ser
            340                 345                 350

Glu Glu Gln Lys Val Val Gln Val Val Ala Pro Glu Thr Gly Leu Trp
            355                 360                 365

Gln Cys Leu Leu Ser Glu Gly Asp Lys Val Lys Met Asp Ser Arg Ile
            370                 375                 380

Gln Val Leu Ser Arg Gly Val Asn Gln Thr Val Phe Leu Ala Cys Val
385                 390                 395                 400

Leu Gly Gly Ser Phe Gly Phe Leu Gly Phe Leu Gly Leu Cys Ile Leu
                405                 410                 415

Cys Cys Val Arg Cys Arg His Gln Gln Arg Gln Ala Ala Arg Met Ser
            420                 425                 430

Gln Ile Lys Arg Leu Leu Ser Glu Lys Lys Thr Cys Gln Cys Pro His
            435                 440                 445

Arg Met Gln Lys Ser His Asn Leu Ile
    450                 455
```

```
<210> SEQ ID NO 44
<211> LENGTH: 509
<212> TYPE: PRT
<213> ORGANISM: Mus musculus

<400> SEQUENCE: 44

Met Gly Cys Val Cys Ser Ser Asn Pro Glu Asp Asp Trp Met Glu Asn
1               5                   10                  15

Ile Asp Val Cys Glu Asn Cys His Tyr Pro Ile Val Pro Leu Asp Ser
            20                  25                  30

Lys Ile Ser Leu Pro Ile Arg Asn Gly Ser Glu Val Arg Asp Pro Leu
            35                  40                  45

Val Thr Tyr Glu Gly Ser Leu Pro Pro Ala Ser Pro Leu Gln Asp Asn
    50                  55                  60

Leu Val Ile Ala Leu His Ser Tyr Glu Pro Ser His Asp Gly Asp Leu
65                  70                  75                  80

Gly Phe Glu Lys Gly Glu Gln Leu Arg Ile Leu Glu Gln Ser Gly Glu
                85                  90                  95

Trp Trp Lys Ala Gln Ser Leu Thr Thr Gly Gln Glu Gly Phe Ile Pro
            100                 105                 110

Phe Asn Phe Val Ala Lys Ala Asn Ser Leu Glu Pro Glu Pro Trp Phe
            115                 120                 125

Phe Lys Asn Leu Ser Arg Lys Asp Ala Glu Arg Gln Leu Leu Ala Pro
            130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
            180                 185                 190

Ile Ser Pro Arg Ile Thr Phe Pro Gly Leu His Asp Leu Val Arg His
            195                 200                 205

Tyr Thr Asn Ala Ser Asp Gly Leu Cys Thr Lys Leu Ser Arg Pro Cys
    210                 215                 220

Gln Thr Gln Lys Pro Gln Lys Pro Trp Trp Glu Asp Glu Trp Glu Val
225                 230                 235                 240
```

-continued

```
Pro Arg Glu Thr Leu Lys Leu Val Glu Arg Leu Gly Ala Gly Gln Phe
            245                 250                 255

Gly Glu Val Trp Met Gly Tyr Tyr Asn Gly His Thr Lys Val Ala Val
            260                 265                 270

Lys Ser Leu Lys Gln Gly Ser Met Ser Pro Asp Ala Phe Leu Ala Glu
            275                 280                 285

Ala Asn Leu Met Lys Gln Leu Gln His Pro Arg Leu Val Arg Leu Tyr
    290                 295                 300

Ala Val Val Thr Gln Glu Pro Ile Tyr Ile Ile Thr Glu Tyr Met Glu
305                 310                 315                 320

Asn Gly Ser Leu Val Asp Phe Leu Lys Thr Pro Ser Gly Ile Lys Leu
            325                 330                 335

Asn Val Asn Lys Leu Leu Asp Met Ala Ala Gln Ile Ala Glu Gly Met
            340                 345                 350

Ala Phe Ile Glu Glu Gln Asn Tyr Ile His Arg Asp Leu Arg Ala Ala
            355                 360                 365

Asn Ile Leu Val Ser Asp Thr Leu Ser Cys Lys Ile Ala Asp Phe Gly
    370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
            405                 410                 415

Phe Thr Ile Lys Ser Asp Val Trp Ser Phe Gly Ile Leu Leu Thr Glu
            420                 425                 430

Ile Val Thr His Gly Arg Ile Pro Tyr Pro Gly Met Thr Asn Pro Glu
            435                 440                 445

Val Ile Gln Asn Leu Glu Arg Gly Tyr Arg Met Val Arg Pro Asp Asn
    450                 455                 460

Cys Pro Glu Glu Leu Tyr His Leu Met Met Leu Cys Trp Lys Glu Arg
465                 470                 475                 480

Pro Glu Asp Arg Pro Thr Phe Asp Tyr Leu Arg Ser Val Leu Asp Asp
            485                 490                 495

Phe Phe Thr Ala Thr Glu Gly Gln Tyr Gln Pro Gln Pro
            500                 505
```

```
<210> SEQ ID NO 45
<211> LENGTH: 30
<212> TYPE: PRT
<213> ORGANISM: Mus musculus
<220> FEATURE:
<221> NAME/KEY: MISC_FEATURE
<222> LOCATION: (26)..(26)
<223> OTHER INFORMATION: CD4 clasp cysteine
<220> FEATURE:
<221> NAME/KEY: MISC_FEATURE
<222> LOCATION: (28)..(28)
<223> OTHER INFORMATION: CD4 clasp cysteine

<400> SEQUENCE: 45

Val Arg Cys Arg His Gln Gln Arg Gln Ala Ala Arg Met Ser Gln Ile
1               5                   10                  15

Lys Arg Leu Leu Ser Glu Lys Lys Thr Cys Gln Cys Pro His
            20                  25                  30
```

```
<210> SEQ ID NO 46
<211> LENGTH: 66
<212> TYPE: PRT
<213> ORGANISM: Mus musculus
<220> FEATURE:
```

-continued

```
<221> NAME/KEY: MISC_FEATURE
<222> LOCATION: (20)..(20)
<223> OTHER INFORMATION: Lck clasp cysteines
<220> FEATURE:
<221> NAME/KEY: MISC_FEATURE
<222> LOCATION: (23)..(23)
<223> OTHER INFORMATION: Lck clasp cysteines

<400> SEQUENCE: 46

Met Gly Cys Val Cys Ser Ser Asn Pro Glu Asp Asp Trp Met Glu Asn
1               5                   10                  15

Ile Asp Val Cys Glu Asn Cys His Tyr Pro Ile Val Pro Leu Asp Ser
            20                  25                  30

Lys Ile Ser Leu Pro Ile Arg Asn Gly Ser Glu Val Arg Asp Pro Leu
        35                  40                  45

Val Thr Tyr Glu Gly Ser Leu Pro Pro Ala Ser Pro Leu Gln Asp Asn
    50                  55                  60

Leu Val
65

<210> SEQ ID NO 47
<211> LENGTH: 30
<212> TYPE: PRT
<213> ORGANISM: Artificial Sequence
<220> FEATURE:
<223> OTHER INFORMATION: CD4-Lck (CD4JM Link)

<400> SEQUENCE: 47

Val Arg Cys Arg His Gln Gln Arg Gln Ala Ala Arg Met Ser Gln Ile
1               5                   10                  15

Lys Arg Leu Leu Ser Glu Lys Lys Thr Gly Thr Ser His Tyr
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: CD4-Lck (Lck linkage)
<220> FEATURE:
<221> NAME/KEY: MISC_FEATURE
<222> LOCATION: (1)..(2)
<223> OTHER INFORMATION: CD4 originating sequence
<220> FEATURE:
<221> NAME/KEY: MISC_FEATURE
<222> LOCATION: (3)..(6)
<223> OTHER INFORMATION: Linakge sequence
<220> FEATURE:
<221> NAME/KEY: MISC_FEATURE
<222> LOCATION: (7)..(34)
<223> OTHER INFORMATION: Lck originating sequence
<220> FEATURE:
<221> NAME/KEY: MISC_FEATURE
<222> LOCATION: (7)..(30)
<223> OTHER INFORMATION: Lck originating sequence
<220> FEATURE:
<221> NAME/KEY: MISC_FEATURE
<222> LOCATION: (25)..(25)
<223> OTHER INFORMATION: Lck clasp cysteines
<220> FEATURE:
<221> NAME/KEY: MISC_FEATURE
<222> LOCATION: (28)..(28)
<223> OTHER INFORMATION: Lck clasp cysteines

<400> SEQUENCE: 48

Val Arg Ala Ala Ala Ser Gly Cys Val Cys Ser Ser Asn Pro Glu Asp
1               5                   10                  15

Asp Trp Met Glu Asn Ile Asp Val Cys Glu Asn Cys His Tyr
```

-continued

```
        20              25              30
```

<210> SEQ ID NO 49
<211> LENGTH: 34
<212> TYPE: PRT
<213> ORGANISM: Artificial Sequence
<220> FEATURE:
<223> OTHER INFORMATION: CD4-Lck (Lck SH3 linkage)
<220> FEATURE:
<221> NAME/KEY: MISC_FEATURE
<222> LOCATION: (1)..(2)
<223> OTHER INFORMATION: CD4 originating sequence
<220> FEATURE:
<221> NAME/KEY: MISC_FEATURE
<222> LOCATION: (3)..(6)
<223> OTHER INFORMATION: Linkage sequence
<220> FEATURE:
<221> NAME/KEY: MISC_FEATURE
<222> LOCATION: (7)..(34)
<223> OTHER INFORMATION: Lck originating sequence

<400> SEQUENCE: 49

Val Arg Ala Ala Ala Ser Asp Asn Leu Val Ile Ala Leu His Ser Tyr
1               5                   10                  15

Glu Pro Ser His Asp Gly Asp Leu Gly Phe Glu Lys Gly Glu Gln Leu
            20                  25                  30

Arg Ile

<210> SEQ ID NO 50
<211> LENGTH: 30
<212> TYPE: PRT
<213> ORGANISM: Artificial Sequence
<220> FEATURE:
<223> OTHER INFORMATION: CD4-Lck (Lck Spe linkage)
<220> FEATURE:
<221> NAME/KEY: MISC_FEATURE
<222> LOCATION: (1)..(25)
<223> OTHER INFORMATION: CD4 originating sequence
<220> FEATURE:
<221> NAME/KEY: MISC_FEATURE
<222> LOCATION: (26)..(28)
<223> OTHER INFORMATION: Linkage sequence
<220> FEATURE:
<221> NAME/KEY: MISC_FEATURE
<222> LOCATION: (29)..(30)
<223> OTHER INFORMATION: Lck originating sequence

<400> SEQUENCE: 50

Val Arg Cys Arg His Gln Gln Arg Gln Ala Ala Arg Met Ser Gln Ile
1               5                   10                  15

Lys Arg Leu Leu Ser Glu Lys Lys Thr Gly Thr Ser His Tyr
            20                  25                  30

<210> SEQ ID NO 51
<211> LENGTH: 1486
<212> TYPE: DNA
<213> ORGANISM: Artificial Sequence
<220> FEATURE:
<223> OTHER INFORMATION: SCoR with a CD8? Ig domain replaced with the
      H57 light chain comprising a F32V mutation and a CD8a Ig domain
      replaced with the H57 heavy chain

<400> SEQUENCE: 51
atggctacaa ggctcctctg ttacacagta ctttgtctcc tgggtgcaag aattttgaac      60
tcaaaatacc catacgatgt tccagattac gctggaggat cctatgagct gatccagccc     120
agttctgcct ctgtgactgt aggcgagacc gttaagataa catgtagtgg tgaccaacta     180
ccgaagaatg ctgcatattg gttccagcag aagtcggaca aaaacatcct cttacttatt     240
```

```
tacatggata acaaaagacc tagcggaatc cccgaacggt tctcaggcag cacttcaggg      300
acgaccgcga ccctgacaat ttccggcgct cagccagagg acgaagccgc ttattactgc      360
ttgtccagct acggagataa caatgatctg gtctttgggt ccggtacaca gctcaccgtg      420
ctgtccggag atgtccttcc tacaactgcc ccaaccaaga agactaccct gaagatgaag      480
aagaagaagc aatgcccgtt cccccaccca gagacccaga agggcctgac atgcagcctt      540
accaccctca gctgctggt agtctgcatc ctgcttctgc tggcattcct cggagtggcc       600 gtctacttt actgtgtgcg gaggagagcc cgcattcact tcatgaaaca gtttcacaaa       660
agatctggcg gagagggcag aggaagtctg ctaacatgcg gtgacgtcga ggagaatcct      720
ggcccaatgc agaggaacct gggagctgtg ctggggattc tgtgggtgca gatttgctgg      780
gtgagaggaa ctagtgaggt ctacctcgtg gaatcaggag gagacctcgt gcagccaggc      840
agcagcctaa aagttagttg tgctgcatct ggcttcacct ttagtgactt ctggatgtac      900
tgggttcgcc aggctcctgg aaaaggactg gagtgggtgg tcgcatcaa gaacatcccc       960 aataactatg ccacagaata tgctgacagt gttcgaggac gcttcactat ttccagagat     1020
gacagccgaa attctattta tctgcagatg aaccgccttc gtgtggatga tacagccatt     1080
tactactgca cccgagctgg acgatttgac cactttgatt attggggcca gggcacaatg     1140
gtgactgttt ctggtaccaa agtgaactct actactacca agccagtgct gcgaactccc     1200
tcacctgtgc accctaccgg gacatctcag ccccagagac cagaagattg tcggcccgt      1260 ggctcagtga aggggaccgg attggacttc gcctgtgata tttacatctg ggcacccttg     1320
gccggaatct gcgtggcccc tctgctgtcc ttgatcatca ctctcatctg ctaccacagg     1380
agccgaaagc gtgtttgcaa atgtcccagg ccgctagtca gacaggaagg caagcccaga     1440
ccttcagaga aaattgtggc ggccgcatga taattgaatt catgac                    1486
```

<210> SEQ ID NO 52
<211> LENGTH: 1486
<212> TYPE: DNA
<213> ORGANISM: Artificial Sequence
<220> FEATURE:
<223> OTHER INFORMATION: SCoR with a CD8β Ig domain replaced with the
      H57 light chain and a CD8a Ig domain replaced with the H57 heavy
      chain comprising a W33A mutation.

<400> SEQUENCE: 52

```
atggctacaa ggctcctctg ttacacagta ctttgtctcc tgggtgcaag aattttgaac       60
tcaaaatacc catacgatgt tccagattac gctggaggat cctatgagct gatccagccc      120
agttctgcct ctgtgactgt aggcgagacc gttaagataa catgtagtgg tgaccaacta      180
ccgaagaatt ttgcatattg gttccagcag aagtcggaca aaaacatcct cttacttatt      240
tacatggata acaaaagacc tagcggaatc cccgaacggt tctcaggcag cacttcaggg      300
acgaccgcga ccctgacaat ttccggcgct cagccagagg acgaagccgc ttattactgc      360
ttgtccagct acggagataa caatgatctg gtctttgggt ccggtacaca gctcaccgtg      420
ctgtccggag atgtccttcc tacaactgcc ccaaccaaga agactaccct gaagatgaag      480
aagaagaagc aatgcccgtt cccccaccca gagacccaga agggcctgac atgcagcctt      540
accaccctca gctgctggt agtctgcatc ctgcttctgc tggcattcct cggagtggcc       600 gtctacttt actgtgtgcg gaggagagcc cgcattcact tcatgaaaca gtttcacaaa       660
agatctggcg gagagggcag aggaagtctg ctaacatgcg gtgacgtcga ggagaatcct      720
```

-continued

```
ggcccaatgc agaggaacct gggagctgtg ctggggattc tgtgggtgca gatttgctgg      780
gtgagaggaa ctagtgaggt ctacctcgtg gaatcaggag gagacctcgt gcagccaggc      840
agcagcctaa aagttagttg tgctgcatct ggcttcacct ttagtgactt cgcaatgtac      900
tgggttcgcc aggctcctgg aaaaggactg gagtgggtgg gtcgcatcaa gaacatcccc      960
aataactatg ccacagaata tgctgacagt gttcgaggac gcttcactat ttccagagat     1020
gacagccgaa attctattta tctgcagatg aaccgccttc gtgtggatga tacagccatt     1080
tactactgca cccgagctgg acgatttgac cactttgatt attggggcca gggcacaatg     1140
gtgactgttt ctggtaccaa agtgaactct actactacca agccagtgct gcgaactccc     1200
tcacctgtgc accctaccgg gacatctcag ccccagagac cagaagattg tcggccccgt     1260
ggctcagtga aggggaccgg attggacttc gcctgtgata tttacatctg ggcacccttg     1320
gccggaatct gcgtggcccc tctgctgtcc ttgatcatca ctctcatctg ctaccacagg     1380
agccgaaagc gtgtttgcaa atgtcccagg ccgctagtca gacaggaagg caagcccaga     1440
ccttcagaga aaattgtggc ggccgcatga taattgaatt catgac                    1486
```

```
<210> SEQ ID NO 53
<211> LENGTH: 1486
<212> TYPE: DNA
<213> ORGANISM: Artificial Sequence
<220> FEATURE:
<223> OTHER INFORMATION: SCoR with a CD8? Ig domain replaced with the
      H57 light chain comprising a F32V mutation and a CD8a Ig domain
      replaced with the H57 heavy chain comprising a W33A mutation

<400> SEQUENCE: 53
```

```
atggctacaa ggctcctctg ttacacagta ctttgtctcc tgggtgcaag aattttgaac       60
tcaaaatacc catacgatgt tccagattac gctggaggat cctatgagct gatccagccc      120
agttctgcct ctgtgactgt aggcgagacc gttaagataa catgtagtgg tgaccaacta      180
ccgaagaatt ttgcatattg gttccagcag aagtcggaca aaaacatcct cttacttatt      240
tacatggata caaaagacc tagcggaatc cccgaacggt tctcaggcag cacttcaggg      300
acgaccgcga ccctgacaat ttccggcgct cagccagagg acgaagccgc ttattactgc      360
ttgtccagct acggagataa caatgatctg gtctttgggt ccggtacaca gctcaccgtg      420
ctgtccggag atgtccttcc tacaactgcc ccaaccaaga agactaccct gaagatgaag      480
aagaagaagc aatgcccgtt cccccaccca gagacccaga agggcctgac atgcagcctt      540
accaccctca gcctgctggt agtctgcatc ctgcttctgc tggcattcct cggagtggcc      600
gtctactttt actgtgtgcg gaggagagcc cgcattcact tcatgaaaca gtttcacaaa      660
agatctggcg gagagggcag aggaagtctg ctaacatgcg tgacgtcga ggagaatcct      720 ggcccaatgc agaggaacct gggagctgtg ctggggattc tgtgggtgca gatttgctgg      780
gtgagaggaa ctagtgaggt ctacctcgtg gaatcaggag gagacctcgt gcagccaggc      840
agcagcctaa aagttagttg tgctgcatct ggcttcacct ttagtgactt cgcaatgtac      900
tgggttcgcc aggctcctgg aaaaggactg gagtgggtgg gtcgcatcaa gaacatcccc      960
aataactatg ccacagaata tgctgacagt gttcgaggac gcttcactat ttccagagat     1020
gacagccgaa attctattta tctgcagatg aaccgccttc gtgtggatga tacagccatt     1080
tactactgca cccgagctgg acgatttgac cactttgatt attggggcca gggcacaatg     1140
gtgactgttt ctggtaccaa agtgaactct actactacca agccagtgct gcgaactccc     1200
tcacctgtgc accctaccgg gacatctcag ccccagagac cagaagattg tcggccccgt     1260
```

-continued

```
ggctcagtga aggggaccgg attggacttc gcctgtgata tttacatctg ggcacccttg    1320
gccggaatct gcgtggcccc tctgctgtcc ttgatcatca ctctcatctg ctaccacagg    1380
agccgaaagc gtgtttgcaa atgtcccagg ccgctagtca gacaggaagg caagcccaga    1440
ccttcagaga aaattgtggc ggccgcatga taattgaatt catgac                   1486
```